US010123805B2

(12) United States Patent
Ayres et al.

(10) Patent No.: US 10,123,805 B2
(45) Date of Patent: Nov. 13, 2018

(54) SPACE FILLING DEVICES

(71) Applicant: W. L. Gore & Associates, Inc., Newark, DE (US)

(72) Inventors: Bridget B. Ayres, Flagstaff, AZ (US); Nathan C. Korey, Flagstaff, AZ (US); Steven J. Masters, Flagstaff, AZ (US); Thomas R. McDaniel, Flagstaff, AZ (US); Aaron L. Paris, Flagstaff, AZ (US); Kenneth M. Schipper, Flagstaff, AZ (US); Nicholas S. Webster, Flagstaff, AZ (US); Roark N. Wolfe, Flagstaff, AZ (US); Peter J. Zeller, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 584 days.

(21) Appl. No.: 14/315,237

(22) Filed: Jun. 25, 2014

(65) Prior Publication Data
US 2015/0005809 A1 Jan. 1, 2015

Related U.S. Application Data

(60) Provisional application No. 61/839,843, filed on Jun. 26, 2013, provisional application No. 61/907,288, filed on Nov. 21, 2013.

(51) Int. Cl.
*A61B 17/12* (2006.01)
*A61F 2/01* (2006.01)
*A61B 17/00* (2006.01)

(52) U.S. Cl.
CPC .. *A61B 17/12122* (2013.01); *A61B 17/12172* (2013.01); *A61B 17/12177* (2013.01);
(Continued)

(58) Field of Classification Search
CPC ............... A61F 2/01; A61B 17/12177; A61B 2017/00867; A61B 2017/00526;
(Continued)

(56) References Cited

U.S. PATENT DOCUMENTS 4,425,908 A 1/1984 Simon
5,601,595 A * 2/1997 Smith ..................... A61F 2/01
606/200

(Continued)

FOREIGN PATENT DOCUMENTS

WO 2013/040431 3/2013

OTHER PUBLICATIONS

Annex Form PCT/ISA/206 Communication Relating to the Results of the Partial International Search for PCT/US2014/044358 dated Feb. 16, 2015, corresponding to U.S. Appl. No. 14/315,237, 2 pgs.
(Continued)

*Primary Examiner* — Jing Ou

(57) ABSTRACT

A device frame includes a plurality of elongate frame members, first and second hub members substantially aligned along a longitudinal axis of the device frame, and a coupling element that couples the first hub member to the second hub member. The device frame includes a face section, a laterally facing skirt section, and an inverted section. First portions of the elongate members define the face section and extend radially from the first hub member. Second portions of the elongate members define the laterally facing skirt section and extend in a distal, axial, and helical direction along a first rotational direction from the face section. Third portions of the elongate members define the inverted section and extend in a generally proximal direction from a distal portion of the laterally facing skirt section to the second hub member along a rotational direction opposite the first rotational direction.

9 Claims, 54 Drawing Sheets

(52) U.S. Cl.
CPC .......... *A61F 2/01* (2013.01); *A61B 17/12109* (2013.01); *A61B 2017/00004* (2013.01); *A61B 2017/00526* (2013.01); *A61B 2017/00575* (2013.01); *A61B 2017/00579* (2013.01); *A61B 2017/00592* (2013.01); *A61B 2017/00597* (2013.01); *A61B 2017/00615* (2013.01); *A61B 2017/00632* (2013.01); *A61B 2017/00867* (2013.01); *A61B 2017/00986* (2013.01)

(58) Field of Classification Search
CPC .......... A61B 2017/00579; A61B 2017/00615; A61B 2017/00986; A61B 2017/00597; A61B 17/12172; A61B 17/12122; A61B 17/12109; A61B 2017/00575; A61B 2017/00592; A61B 2017/00632; A61B 2017/00004
See application file for complete search history.

(56) References Cited

U.S. PATENT DOCUMENTS

| | | | |
|---|---|---|---|
| 5,669,933 A * | 9/1997 | Simon | A61F 2/01 600/191 |
| 6,712,835 B2 | 3/2004 | Mazzocchi et al. | |
| 2001/0000799 A1 | 5/2001 | Wessman et al. | |
| 2003/0181942 A1 | 9/2003 | Sutton et al. | |
| 2004/0122467 A1 | 6/2004 | Vantassel et al. | |
| 2004/0220610 A1 | 11/2004 | Kreidler | |
| 2005/0234503 A1 * | 10/2005 | Ravenscroft | A61F 2/01 606/200 |
| 2006/0069406 A1 * | 3/2006 | Hendriksen | A61F 2/01 606/200 |
| 2007/0066993 A1 | 3/2007 | Kreidler | |
| 2007/0162048 A1 | 7/2007 | Quinn et al. | |
| 2010/0063533 A1 | 3/2010 | Sokolov | |
| 2011/0054515 A1 | 3/2011 | Bridgeman et al. | |
| 2012/0143242 A1 | 6/2012 | Masters | |
| 2012/0172927 A1 | 7/2012 | Campbell et al. | |
| 2013/0178889 A1 | 7/2013 | Miles et al. | |

OTHER PUBLICATIONS

International Search Report and Written Opinion for PCT/US2014/044358 dated May 6, 2015, corresponding to U.S. Appl. No. 14/315,237, 6 pgs.

\* cited by examiner

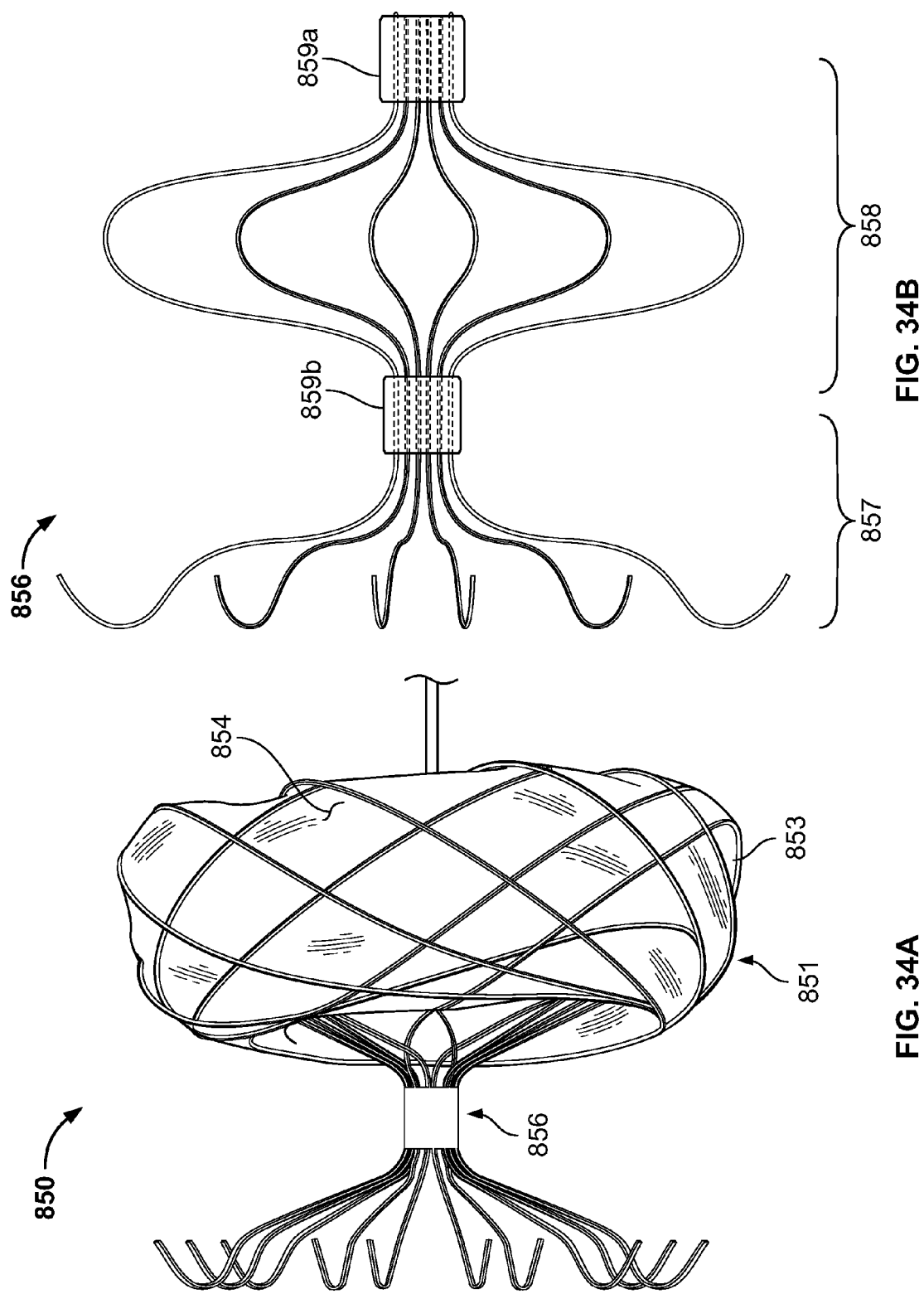

SPACE FILLING DEVICES

TECHNICAL FIELD

The present disclosure relates to implantable medical devices that may be used to occlude apertures, conduits, or structures within a patient.

BACKGROUND

Cardiac features such as atrial appendages can contribute to cardiac blood flow disturbance, which is associated with a number of cardiac-related pathologies. For example, complications caused by blood flow disturbance within the left atrial appendage (LAA) and associated with atrial fibrillation can contribute to embolic stroke. The LAA is a muscular pouch extending from the anterolateral wall of the left atrium of the heart and serves as a reservoir for the left atrium. During a normal cardiac cycle, the LAA contracts with the left atrium to pump blood from the LAA, which generally prevents blood from stagnating within the LAA. However, during cardiac cycles characterized by arrhythmias (e.g., atrial fibrillation), the LAA often fails to sufficiently contract, which can allow blood to stagnate within the LAA. Stagnant blood within the LAA is susceptible to coagulating and forming a thrombus, which can dislodge from the LAA and ultimately result in an embolic stroke.

SUMMARY

In a first general aspect, a medical device includes a device frame that includes a plurality of elongate frame members, where each of the elongate frame members includes a first end and a second end. The medical device also includes a first hub member that aggregates the first ends of the plurality of elongate members, and a second hub member that aggregates the second ends of the plurality of elongate members. The medical device further includes a coupling element that couples the first hub member to the second hub member, where the first hub member and the second hub member are substantially aligned along a longitudinal axis of the device frame. The device frame includes a face section, a laterally facing skirt section, and an inverted section, and first portions of the elongate members define the face section and extend radially from the first hub member, second portions of the elongate members define the laterally facing skirt section and extend in a distal, axial, and helical direction along a first rotational direction from the face section, and third portions of the elongate members define the inverted section and extend in a generally proximal direction from a distal portion of the laterally facing skirt section to the second hub member along a rotational direction opposite the first rotational direction.

Various implementations may include one or more of the following. The coupling element may be an adhesive, a weld, a rivet, or a mechanical component. For each of the elongate frame members, an angle defined between an exit location from the first hub member and an entry location to the second hub member may be in the range of about 140° to about 360°, or in the range of about 225° to about 315°, or in the range of about 255° to about 285°, or about 270°. The medical device may also include at least one anchor component attached to the device frame. Each of the elongate frame members may include one or more wires. The elongate frame members may include portions of a tube. The first rotational direction may be clockwise, or counter-clockwise. The face section of the device frame may be substantially flat, or may have a generally convex shape or a generally concave shape. The first hub member may be an eyelet and the second hub member may be an eyelet. The first hub member may be a ring member and the second hub member may be an eyelet. The first hub member may be a ring member and the second hub member may be a ring member. The second hub member may be disposed concentrically within the first hub member. The medical device may also include a covering component attached to the face section and to the laterally facing skirt section. The covering component may not be attached to the inverted section. The covering component may be configured to inhibit passage of blood through the covering component. The covering component may be configured filter by allowing blood to pass through the covering component but not allowing emboli to pass through the covering component. A first portion of the inverted section may oppose at least a portion of the laterally facing skirt section, and a second portion of the inverted section may oppose at least a portion of the face section. The medical device may also include a covering component attached to the face section, the laterally facing skirt section, and the second portion of the inverted section, where the covering component may not be attached to the first portion of the inverted section.

In a second general aspect, a medical device includes a device frame that includes a plurality of elongate frame members, where each of the elongate frame members includes a first end and a second end. The medical device also includes a first hub member that aggregates the first ends of the plurality of elongate members, and a second hub member that aggregates the second ends of the plurality of elongate members. The medical device also includes a coupling element that couples the first hub member to the second hub member, and the first hub member and the second hub member are substantially aligned along a longitudinal axis of the device frame. The device frame includes a face section, a laterally facing skirt section, and an inverted section. First portions of the elongate members define the face section and extend radially from the first hub member, second portions of the elongate members define the laterally facing skirt section and extend in a distal, axial, and helical direction along a first rotational direction from the face section, and third portions of the elongate members define the inverted section and extend in a generally proximal direction from a distal portion of the laterally facing skirt section to the second hub member along a rotational direction opposite the first rotational direction. The medical device further includes a covering component attached to the face section and to the laterally facing skirt section.

Various implementations can include one or more of the following. The covering component may not be attached to the inverted section. The covering component may be configured to inhibit passage of blood through the covering component. The covering component may be configured to filter by allowing blood to pass through the covering component but not allowing emboli to pass through the covering component. A first portion of the inverted section may oppose at least a portion of the laterally facing skirt section, and a second portion of the inverted section may oppose at least a portion of the face section. The covering component may be attached to the second portion of the inverted section and may not be attached to the first portion of the inverted section.

The details of one or more embodiments are set forth in the accompanying drawings and the description below. Other features, objects, and advantages will be apparent from the description and drawings, and from the claims.

BRIEF DESCRIPTION OF THE DRAWINGS

FIG. 34A shows a perspective view of another example occlusive device embodiment.

FIG. 34B depicts a distal anchoring member that can be used with the occlusive device of FIG. 34A.

Like reference symbols in the various drawings indicate like elements.

DETAILED DESCRIPTION

Figure 1A:
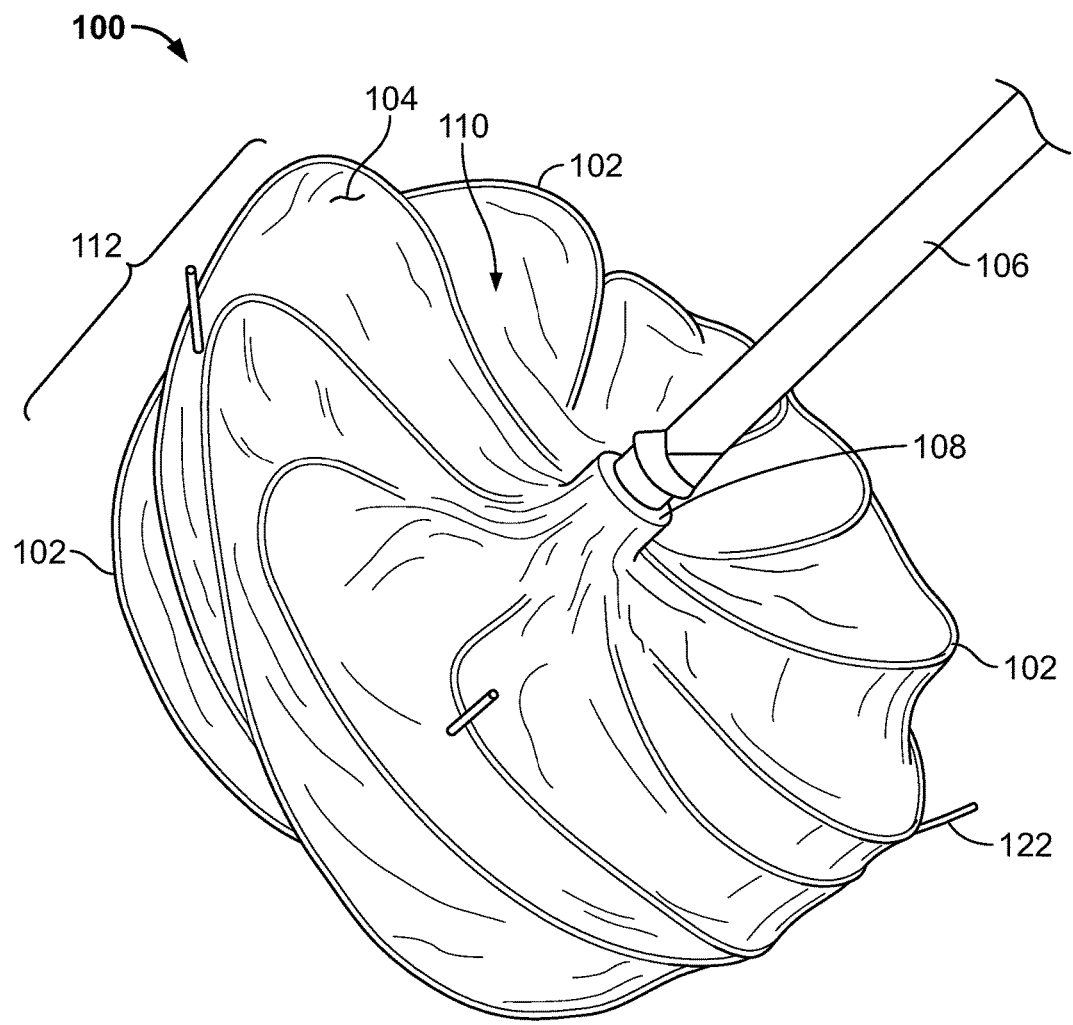
FIGS. 1A, 1B, and 1C are perspective views of an example occlusive device that can be used to occlude a hole, defect, aperture, appendage, vessel or conduit within a body of a patient.

This document describes devices, systems and methods that are useful, for example, for fully, partially, or substantially occluding spaces, holes, defects, apertures, appendages, vessels or conduits within a body of a patient. An additional use, in some implementations, can include filtering. Several implantable medical devices are described herein, and in general any of the features described with respect to a particular device may also be used with any of the other devices described herein. In some examples, one or more features described with respect to a particular device may replace or be substituted for one or more features of another device. In some examples, one or more features described with respect to a particular device may be added to or included with another device. Also, various combinations or sub-combinations of any of the features described herein may generally be used with any of the devices described herein.

In general, any of the implantable medical devices described herein can be delivered to, and deployed at, an in vivo deployment site within a body of a patient using various minimally invasive transcatheter deployment techniques. For example, any of the implantable medical devices described herein may be releasably attached to a delivery catheter, and the device and delivery catheter may be loaded into a delivery sheath. The delivery sheath may be introduced to the vasculature of the patient and advanced through the vasculature, until a distal end of the delivery sheath is located at or near the target in vivo deployment site. The implantable medical device may be deployed at the deployment site, for example by pushing the device out the distal end of the delivery sheath using the delivery catheter and detaching the device from the delivery catheter. In some examples, the device can be deployed by retracting the delivery sheath while maintaining (or advancing) a position of the delivery catheter and the implantable medical device, and detaching the device from the delivery catheter. In some implementations, a first portion of the device is released from the delivery sheath while a second portion of the device remains constrained by the delivery sheath, a positioning of the first portion of the device is verified, and then the second portion of the device is released from the delivery sheath. The delivery catheter and delivery sheath can then be withdrawn or retracted from the body of the patient. In some examples, a retrieval element such as a tether, suture, or cable, is releasably attached to a portion of the device. The retrieval element can be used to retrieve or recapture the device after deployment, if desired.

Any of the implantable medical devices discussed herein can be used to occlude a left atrial appendage (LAA) of a human heart. The implantable medical devices can be delivered in an endovascular manner through or over a catheter system to a delivery site, such as the LAA or other appropriate delivery site, and deployed at the site. The implantable medical devices can be deployed within the LAA and/or across the ostium of the LAA to isolate the LAA from the main chamber of the left atrium (left atrial chamber), for example. This may prevent thrombus formation within the LAA and/or thrombus exit from the LAA. In this manner, a risk of stroke may be reduced or minimized.

Without limitation devices described here can be used to occlude spaces, holes, defects, apertures, vessels, conduits, or appendages within a body of a patient, including the heart, such as right or left atrial appendages, fistulas, aneurysms, and patent ductus arteriousus. The occlusive devices provide a frame that is compliant enough to conform to a wide variety of opening geometries and sizes, and offer a high degree of conformability to conform to various structural geometries at the deployment site. Particularly, embodiments of the devices can provide a left atrial appendage occlusion device frame that provides firm, secure anchoring with significantly reduced clinical sequela from piercing or without traumatic piercing of the left atrial appendage tissue. While the devices discussed herein will generally be described as for use in occlusion applications, the devices can also be applicable for filtering applications. For example, the device frames described herein can be used for occlusion applications, filtering applications, and others. As an example, any of the frames described herein can be fully, substantially, or partially covered by a covering component configured to inhibit passage of blood through the covering component for occlusion applications. In some embodiments, any of the frames described herein can be fully, substantially, or partially covered by a covering component configured to filter by permitting blood to pass through the covering component but to inhibit emboli from passing through the covering component for filtering applications. As such, even though the face section of a frame may be described herein as an occlusive face, for example because the frame may be used in an occlusion application, the face section may similarly be described as a filter face for applications where the frame is used to filter rather than occlude.

In some implementations, the devices described herein can assume two or more configurations. For example, while the device is being delivered to the deployment site, the device may assume a collapsed or delivery configuration. Following deployment of the device, the device may assume an expanded or deployed configuration. While the device is being deployed, for example, the device may assume one or more partially expanded or partially deployed configurations.

Figure 1B:
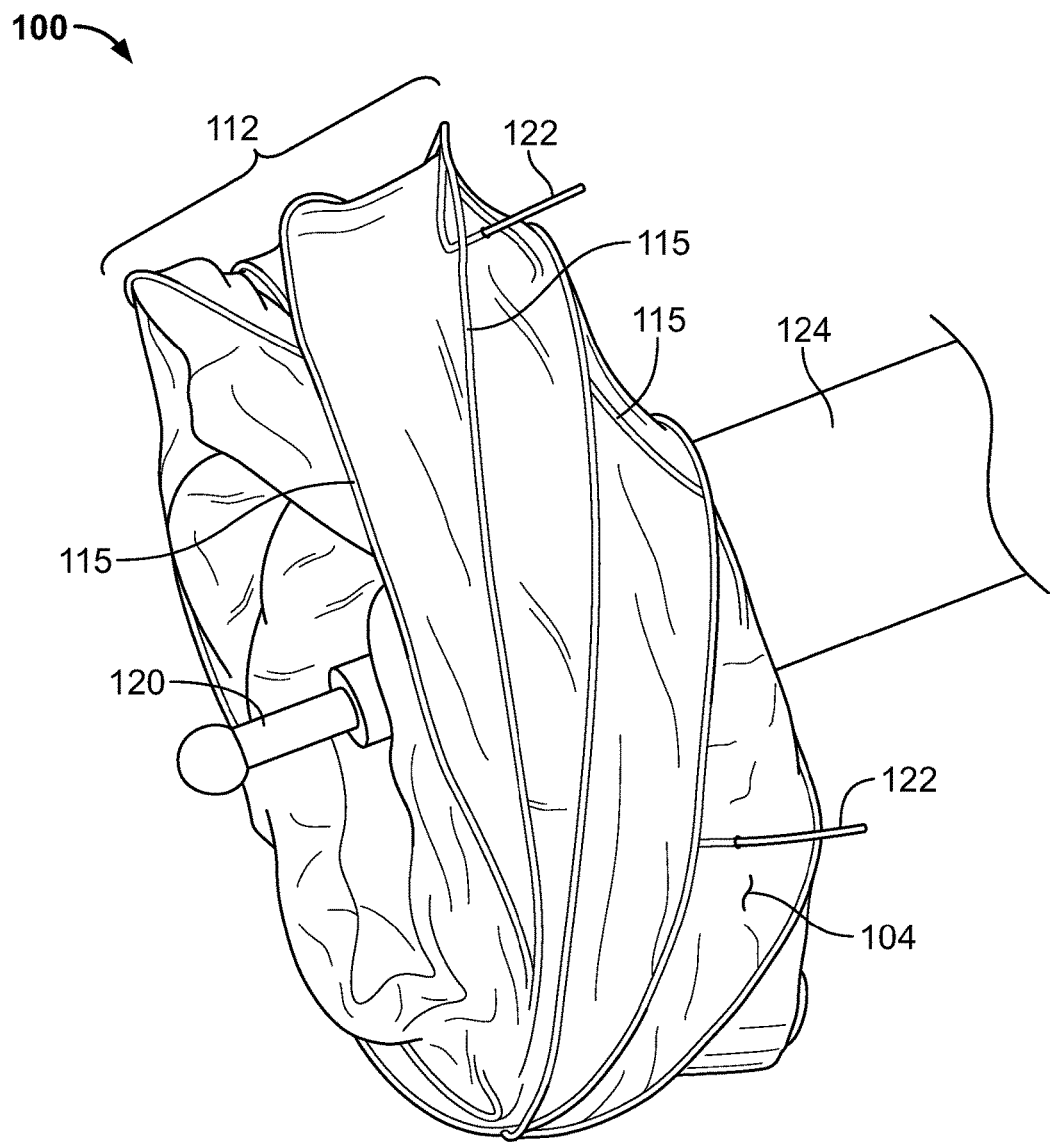
Figure 1C:
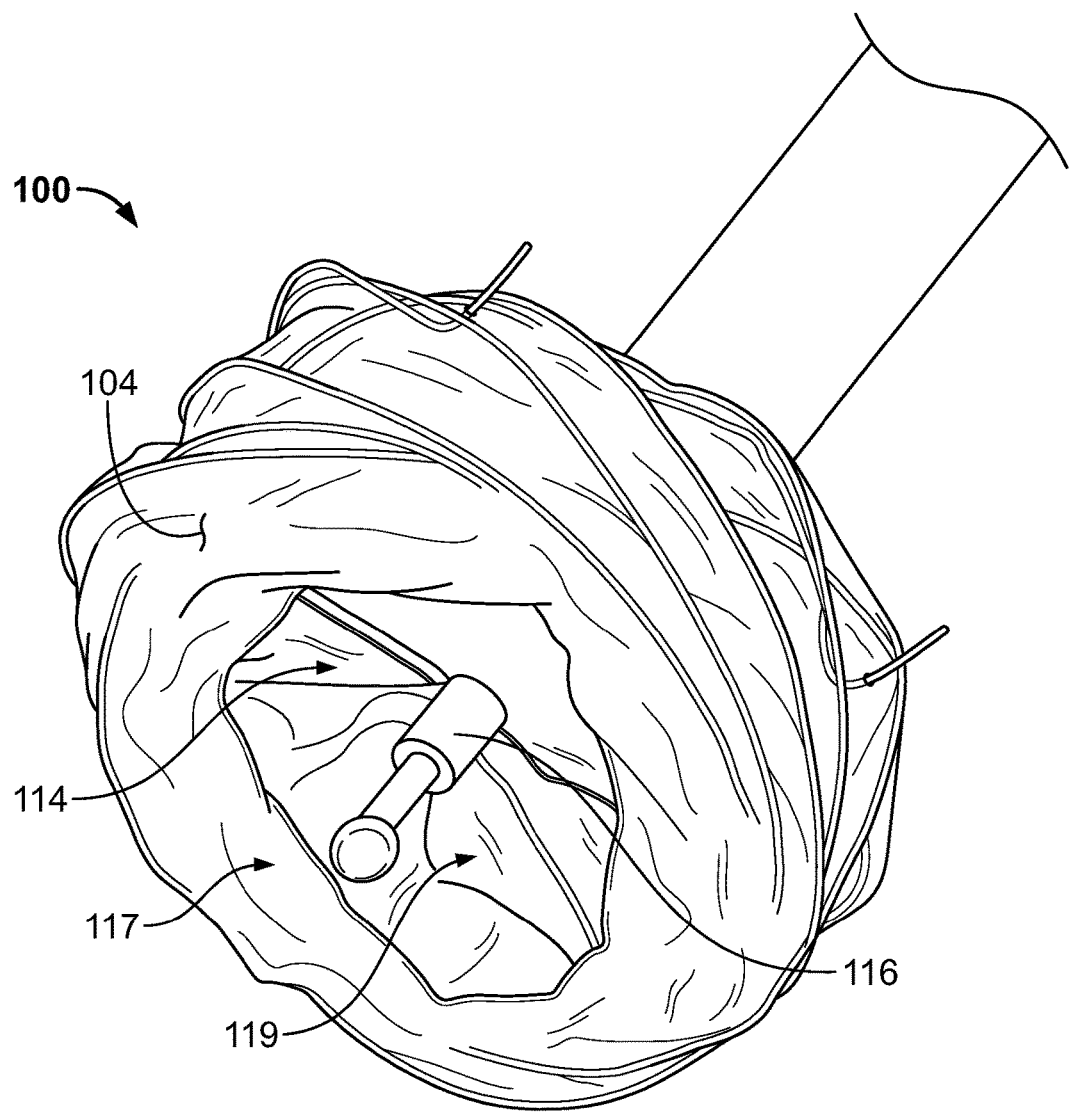

FIGS. 1A, 1B, and 1C are perspective views of an example occlusive device 100 that can be used to occlude a hole, defect, aperture, appendage, vessel or conduit within a body of a patient. The occlusive device 100 includes a device frame comprised of a plurality of elongate members 102, and includes a covering component 104 that covers at least a portion of the frame. In this example, the covering component 104 covers a portion of the frame and is attached to portions of the elongate members 102. As used herein, "frame" may refer to an entire frame of a device, or may alternatively refer to a localized portion of a device that includes at least one elongate member. The occlusive device 100 is releasably attached, in FIG. 1A, to an example delivery catheter 106 at a first hub member 108. In some embodiments, the first hub member 108 and a second hub member 116 are connectable, and the delivery catheter 106 can be releasably attached to both the first hub member 108 and the second hub member 116.

In general, the elongate members 102 of occlusive device 100 are configured to define at least one occlusive face 110 of the device frame, a laterally facing skirt 112 of the device frame, where the skirt extends about a circumference of the frame, and an inverted section 114 (see FIG. 10) of the device frame. The elongate members 102 include a first portion that defines the at least one occlusive face 110 of the device frame, a second portion that defines the laterally facing skirt 112 of the device frame, and a third portion that defines the inverted section 114 of the device frame. The occlusive face 110 may be a generally disc-shaped member, and in various implementations can have a generally circular shape, or can have an oval or generally elliptical shape. The laterally facing skirt 112, as can be seen in FIG. 1B, defines a laterally facing surface of the device 100 that is configured to conform to a wall of a space to be occluded. For example, the laterally facing skirt 112 (along with the covering component 104) may conform to an interior wall of the left atrial appendage, and may assist with occlusion of the appendage by preventing or substantially prevent passage of blood between the skirt 112 and the wall of the appendage. In some embodiments, one or more anchor features 122 are included. In some such embodiments, the anchor features 122 can protrude from the laterally facing skirt 122 to enhance the migration resistance of the device 100. As will be described in more detail below, in some embodiments the inverted section 114 can include a first portion that generally opposes the profile of at least a portion of the laterally facing skirt 112, and a second portion that generally opposes the profile of at least a portion of the occlusive face 110.

Each of the elongate members 102 includes a first end and a second end. The first hub member 108 aggregates the first ends of the elongate members 102, and a second hub member 116 (see FIG. 10) aggregates the second ends of the elongate members 102. That is, each of the elongate members 102 extends from the first hub member 108 to the second hub member 116, and first portions of the elongate members 102 define the occlusive face 110, second portions of the elongate members 102 define the laterally facing skirt 112, and third portions of the elongate members 102 define the inverted section 114. The occlusive device 100 includes ten elongate members.

In general, the device frame includes a face section, a laterally facing skirt section, and an inverted section. First portions of the elongate members define the face section and extend radially from the first hub member. Second portions of the elongate members define the laterally facing skirt section and extend in a distal, axial, and helical direction along a first rotational direction (e.g., counter-clockwise) from the face section. Third portions of the elongate members define the inverted section and extend in a generally proximal direction from a distal portion of the laterally facing skirt section to the second hub member along a rotational direction opposite the first rotational direction (i.e., clockwise in this example).

In general, at the time that the device is initially constructed, the elongate members 102 extend from the first hub member 108 to the second hub member 116 in a common rotational direction. For example, each of the elongate members 102 can extend from the first hub member 108 to the second hub member 116 in a generally clockwise direction. Alternatively, for example, each of the elongate members 102 can extend from the first hub member 108 to the second hub member 116 in a generally counter-clockwise direction. As will be explained in additional detail below, the inverted section of the device gets inverted into an interior of the device, and it is this inversion that causes the portion of the elongate members that define the inverted section to follow a path having rotational direction opposite the rotational direction of the portion of the elongate members that define the laterally facing skirt section of the device frame.

Figure 2:
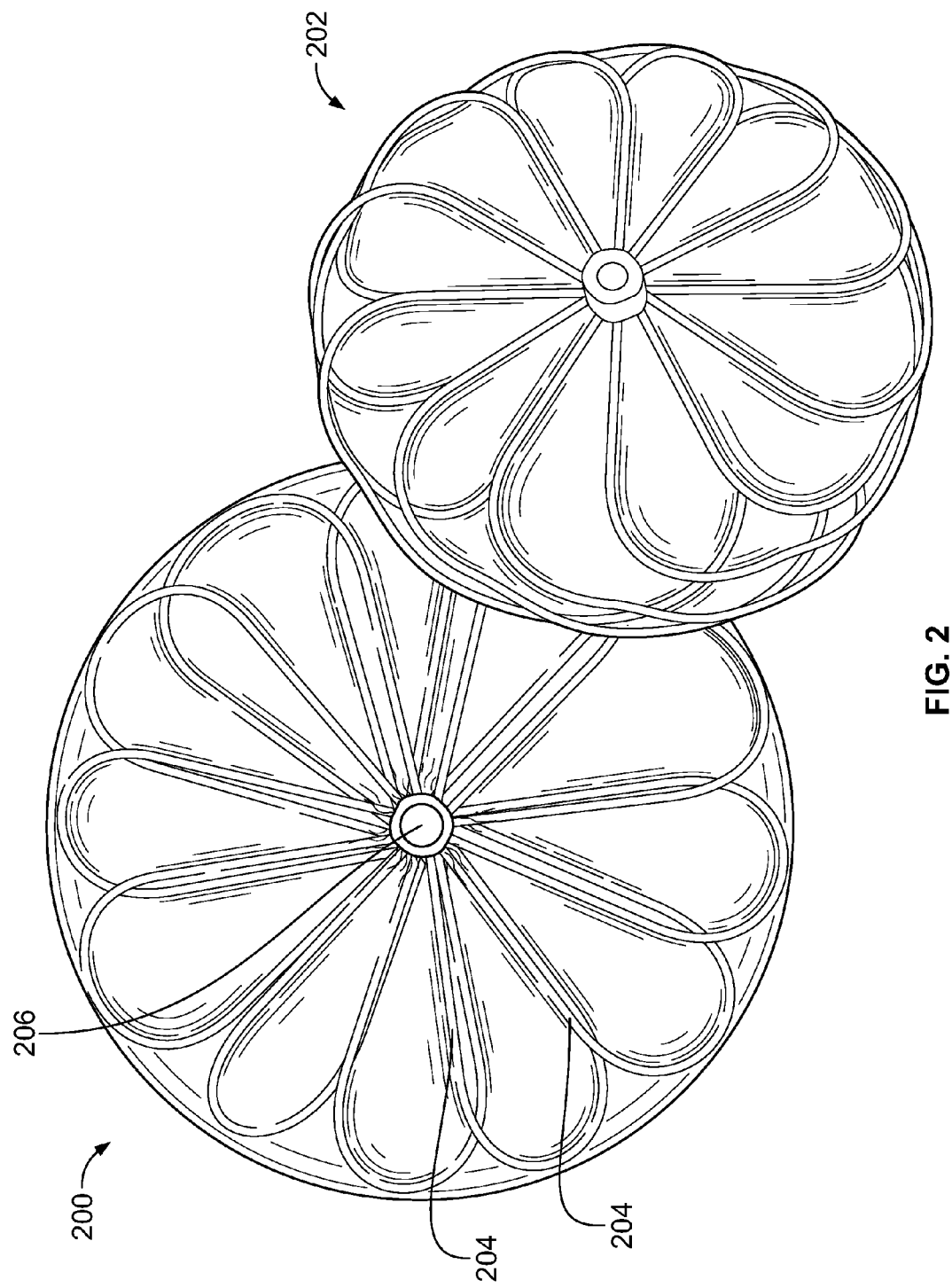
FIG. 2 is a front view of another example occlusive device and a perspective view of yet another example occlusive device.

As can be best seen in FIG. 2, which is a front view of another example occlusive device 200 and a perspective view of yet another example occlusive device 202, for each of the elongate members, the first portion 204 of the elongate member extends generally radially from the first hub member 206. The first portions 204 may be referred to as "struts" of the occlusive face. Devices 200 and 202 are very similar to the occlusive device 100 of FIGS. 1A-C, but include a different number of elongate members (in particular, twelve, rather than ten). This illustrates that the devices discussed herein can be constructed with any appropriate number of elongate members, such as two, three, four, five, six, seven, eight, nine, ten, eleven, twelve, thirteen, fourteen, or more. Also, the devices 200 and 202 illustrate that the occlusive devices can be constructed to have differing diameters for the respective occlusive faces, and to have differing diameters or widths for the corresponding laterally facing skirt.

The devices 200, 202 of FIG. 2 each include an occlusive face that has a generally circular shape. In general, the occlusive face of the devices discussed herein may have a generally flat profile in some embodiments, and in other embodiments may have a convex profile or a concave profile. In some examples, the occlusive face of the device is symmetric about a longitudinal axis of the device. In other examples, the occlusive face is asymmetric or eccentric about the longitudinal axis of the device.

Referring now to device 202 of FIG. 2, upon reaching a perimeter of the occlusive face of the device, the elongate members begin to traverse a helical path and define the laterally facing skirt. As can be best seen with reference to FIG. 1B, the elongate members include second portions 115 that define the laterally facing skirt 112 of the device as they traverse helically in the same rotational direction, as discussed above.

Generally, the view of FIG. 1A shows a proximal portion of the occlusive device 100, and the view of FIG. 1C shows a distal portion of the device 100. Generally, when the device 100 is deployed in a LAA, the occlusive face 100 may be generally oriented to face the left atrial chamber, the laterally facing skirt 112 may be generally oriented to face the wall of the LAA, and the inverted section 114 may be generally oriented to face within the LAA (i.e., to face the interior of the LAA). The inverted section 114 is referred to as being distal of the occlusive face 110 because, after deployment, the position of the inverted section 114 is generally distal of the occlusive face 110 with respect to the delivery system. By contrast, the occlusive face 110 is referred to as being proximal of the inverted section 114 because its deployed position is generally proximal to the delivery system as compared to the inverted section 114. Typically, the distal portion of the device is deployed first, and the proximal portion of the device (e.g., including the occlusive face 110) is deployed thereafter. With respect to a LAA, following deployment of the device, the inverted section 114 may be generally deeper within the interior of the LAA, while the occlusive face 110 may be oriented to face the left atrial chamber of the heart.

The devices discussed herein may generally be pulled into a delivery sheath to load the device, and may generally be pushed out of the delivery sheath to deploy the device. For example, a delivery catheter 106 may be releasably attached to a portion of the device (e.g., an attachment location near a proximal end of the device, the first hub member 108, the first hub member 108 and the second hub member 116, and the like), and used to pull the device 100 into the delivery sheath. The delivery sheath may be introduced to the vasculature of the patient and advanced through the vasculature, as described above, until a distal end of the delivery sheath is located at or near the target in vivo deployment site. The device 100 may then be pushed out of the sheath with the delivery catheter, and the catheter may be detached from the device. In general, the devices discussed herein may be loaded into the sheath and deployed from the sheath without using a control catheter to engage a distal end portion of the device, for example.

Elongate members 102 are wires in some implementations. For example, elongate members 102 can be spring wires, shape memory alloy wires, or super-elastic alloy wires for self-expanding type devices. Elongate members 102 can be made of nitinol (NiTi), L605 steel, stainless steel, or any other appropriate biocompatible material. In some embodiments, drawn wire tubes such as Nitinol tubes with a platinum, tantalum, iridium, palladium, or the like, fill can be used to enhance the elongate members 102 with additional radiographic visibility. In some embodiments, some or all of the elongate members 102 can be coated (e.g., sputter coated) with a radiopaque coating for enhanced radiographic visibility. For example, in some such embodiments portions or all of the elongate members 102 can be coated with a noble metal such as, but not limited to, tantalum, platinum, and the like. In some embodiments, bioresorbable or bioabsorbable materials may be used, for example a bioresorbable or bioabsorbable polymer. The super-elastic properties of NiTi make it a particularly good candidate material for the elongate members 102 (e.g., NiTi wires can be heat-set into a desired shape), according to some implementations. NiTi can be heat-set so that an elongate member 102 can self-expand into a desired shape when the elongate member 102 is placed in a less restrictive environment, such as when it is deployed from the delivery sheath to a body cavity. The elongate members 102 can provide structure and shape for the device 100. In general, the devices described herein include elongate members 102 that are shaped as desired to suit the purpose of the device. The elongate members 102 may generally be conformable, fatigue resistant, and elastic such that the elongate members 102 have a stored length. The elongate members 102 may have a spring nature that allows them to collapse and elongate to a pre-formed shape (e.g., the frame of a device may have a pre-formed shape). The devices described herein may generally be heat set one or more times, as will be discussed further below.

In some embodiments, the diameter or thickness of the elongate members 102 may be about 0.008" to about 0.015", or about 0.009" to about 0.030", but in some embodiments elongate members having smaller or larger diameters may be used. In some embodiments, each of the elongate members 102 has the same diameter. In some embodiments, one or more portions of the elongate members 102 may be diametrically tapered. The elongate members may have a round cross-sectional shape or may have a cross-sectional shape that is not round, such as a rectangle or other polygon. Examples of other cross-sectional shapes that the elongate members 102 may have include square, oval, rectangle, triangle, D-shape, trapezoid, or irregular cross-sectional shape formed by a braided or stranded construct. In some embodiments, a device frame may include flat elongate members 102. In some examples, the elongate members 102 may be formed using a centerless grinding technique, such that the diameter of the elongate members 102 varies along the length of the elongate members 102.

In other embodiments, the elongate members 102 are formed from a tube of material that is cut to remove portions of the tube, leaving the elongate members 102. The tube can be made of nitinol (NiTi), L605 steel, stainless steel, or any other appropriate biocompatible material. In some embodiments, bioresorbable or bioabsorbable materials may be used, for example a bioresorbable or bioabsorbable polymer. The tube of material may be cut in variety of ways. For example, the tube may be cut by a laser. Alternatively, the tube may be cut by a blade, by a water jet, or electrochemically milled, to list just a few examples. The tube is cut according to a prescribed pattern to form elongate members 102, so that the elongate members extend from the first hub member 108 to the second hub member 116. In these cut-tube embodiments, the first and second hub members 108, 116 may comprise cylindrical portions of the tube, for example. The first hub member 108, the second hub member 116, and elongate members 102 may all be considered portions of the tube, as they represent the remaining portions of the tube following the cutting process. Thereafter, the tube may be heat set one or more times, as will be discussed further below.

In some embodiments, one or more elongate members 102 comprises two or more wires (e.g., a twisted pair, or a braided or stranded construct), over at least a portion of the elongate member's path. That is, an elongate member 102 may be considered a two-filar elongate member over a portion or all of its path.

As described above, first hub member 108 and second hub member 116 aggregate, respectively, the first and second ends of elongate members 102. In cut-tube embodiments (i.e., embodiments where a tube of material is cut to define elongate members 102), first hub member 108 and second hub member 116 are typically cylindrical portions of the tube, from which the elongate members 102 extend. In embodiments that include wire-based elongate member 102, the hub members 108, 116 can be eyelets, crimp joints, or ring members, as will be further described below. In some examples, first hub member 108 and second hub member 116 are both eyelets. In some examples, first hub member 108 and second hub member 116 are both ring members. In some examples, first hub member 108 is an eyelet and second hub member 116 is a ring member. In some examples, first hub member 108 is a ring member and second hub member 116 is an eyelet. In some example, first hub member 108 is an eyelet or a ring member and second hub member 116 is a crimp joint.

In some embodiments, the frame of an occlusive device can be formed by cutting and expanding a tube or sheet of material (e.g., refer to FIGS. 18A, 18B, 18C and 19). For example, in some embodiments a frame of an occlusive device can be formed by laser cutting a tube or sheet of NiTi material, expanding the NiTi material to the desired shape, and then heat-setting the material to the desired shape.

In some embodiments, the device frames discussed herein can be constructed with a single hub member. For example, first portions of elongate members can define a face section of the device, second portions of elongate members can define a laterally facing skirt section of the device, and third portions of elongate members can define an inverted section of the device, where first and second ends of the elongate members are aggregated by a single hub member.

Covering component 104 can be configured to inhibit the passage of blood and/or thrombus through the covering component 104, i.e., to substantially occlude or modulate the flow of blood and/or thrombus through the covering component 104. Some embodiments provide a covering component 104 that is configured to induce rapid tissue ingrowth and immediately occludes the passage of blood through the covering component 104. The covering component 104 may be a porous, elastic member that can stretch and collapse to accommodate extension and collapse, respectively, of the elongate members 102. Pores of the covering component 104 may be sized to substantially, or in some examples completely, prevent passage of blood, other bodily fluids, thrombi, and emboli. In some implementations, the covering component 104 prevents or substantially prevents passage of blood, other bodily fluids, emboli, or other bodily materials through the covering component 104. The covering component 104 can have a microporous structure that provides a tissue ingrowth scaffold for durable occlusion and supplemental anchoring strength of the occlusion device 100. Some embodiments of the covering component 104 comprise a fluoropolymer, such as an expanded polytetrafluoroethylene (ePTFE) polymer. In some examples, the covering component 104 can be a membranous covering. In some examples the covering component 104 can be a film.

In some embodiments, the covering component 104 is configured such that the inhibition of fluid passage through the covering component 104 is immediate and does not rely on a thrombotic process. In some embodiments, the covering component 104 can be modified by one or more chemical or physical processes that enhance certain physical properties of the covering component 104. For example, a hydrophilic coating may be applied to the covering component 104 to improve the wettability and echo translucency of the covering component 104. In some embodiments, the covering component 104 may be modified with chemical moieties that promote one or more of endothelial cell attachment, endothelial cell migration, endothelial cell proliferation, and resistance to thrombosis. In some embodiments, the covering component 104 may be modified with covalently attached heparin or impregnated with one or more drug substances that are released in situ to promote wound healing or reduce tissue inflammation. In some embodiments, the drug may be a corticosteroid, a human growth factor, an anti-mitotic agent, an antithrombotic agent, or dexamethasone sodium phosphate.

In some embodiments, the covering component 104 may be formed of a fluoropolymer (e.g., expanded PTFE (ePTFE) or PTFE). In some embodiments, the covering component 104 may be formed of a polyester, a silicone, a urethane, or another biocompatible polymer, or combinations thereof. In some embodiments, bioresorbable or bioabsorbable materials may be used, for example a bioresorbable or bioabsorbable polymer. In some embodiments, the covering component 104 can comprise Dacron. In some embodiments, the covering component 104 can comprise knits or fibers. The covering component 104 may be woven or non-woven in various embodiments. In some embodiments, the covering component 104 may be formed of a copolymer. In some examples, a first portion of the covering component 104 may be formed of a first material and a second portion of the covering component 104 may be formed of a second material. For example, the portion of the covering component 104 that covers the occlusive face 110 may be formed of a first material, and a portion of the covering component 104 that covers the remainder of the device may be formed of a second material. In another example, a portion of the covering component 104 that covers the laterally facing skirt 112 may be formed of a first material, and a portion of the covering component 104 that covers the remainder of the device may be formed of a second material.

In some embodiments, the covering component 104 is attached, as by an adhesive, for example, to the first portions and second portions of the elongate members, but is not attached to the third portions of the elongate members. That is, the covering component is attached to the device frame at the occlusive face 110 and the laterally facing skirt 112 of the device frame, but is not attached to the device frame at the inverted section 114 of the device frame.

In some embodiments, the covering component 104 is attached, as by an adhesive, for example, to the occlusive face 110 and the laterally facing skirt 112 of the device frame. In some embodiments, the covering component 104 is attached to at least some portions of the elongate frame members using an adhesive. In some embodiments, FEP (fluorinated ethylene propylene) is used as an adhesive to attach the covering component 104 to elongate frame members. For example, an FEP coating can be applied to portions of the elongate frame members (e.g., refer to FIG. 8), and the FEP can act as a bonding agent to adhere the covering component 104 to the elongate frame members. In some embodiments, a radiopaque material can be combined with the adhesive. For example, in some embodiments a radiopaque powder (e.g., tungsten powder) can be mixed with the adhesive. When such a radiopaque material is used in conjunction with the adhesive for attaching the covering component 104 to the elongate frame members, the occlusive device 100 (and other devices described herein that include such radiopaque material) can be enhanced from a radiographic visualization standpoint (e.g., using fluoroscopy).

In some embodiments, portions of the covering component 104 can be attached to the elongate members by banding the covering component 104 thereto. For example, in some embodiments portions of the covering component 104, such as but not limited to the ends of the covering component 104, are attached to the elongate members, or to the hub members, using banding. The banding can be a variety of materials, including but not limited to biocompatible film materials, suture materials, metallic materials, and the like, and combinations thereof. Such attachment materials and techniques can also be used for other embodiments of the occlusive devices provided herein.

In some embodiments, the covering component 104 is attached to selected regions of the device frame and not attached to other regions of the device frame. This technique can facilitate enhanced conformability of the occlusive device 150 to the topography of a patient's anatomy at the implant site. Such techniques can also be used with other embodiments of the occlusive devices provided herein.

In some embodiments, covering component 104 is pre-perforated to modulate fluid flow through the covering component 104, to create filtering properties, and/or to affect the propensity for tissue ingrowth to the covering component 104. In some embodiments, the covering component 104 is treated to make the covering component 104 stiffer or to add surface texture. For example, in some embodiments the covering component 104 is treated with FEP powder to provide a stiffened covering component 104 or roughened surface on the covering component 104. In some embodiments, selected portions of the covering component 104 are so treated, while other portions of the covering component 104 are not so treated. Other covering component 104 material treatment techniques can also be employed to provide beneficial mechanical properties and tissue response interactions. Such materials and techniques can also be used for other embodiments of the occlusive devices provided herein.

Regarding the inverted section 114 of the device frame, the covering component 104 can be attached to the portion of the inverted section that opposes the profile of at least a portion of the occlusive face 110, and the covering component 104 is not attached to the portion of the inverted section that generally opposes the profile of at least a portion of the laterally facing skirt 112. See FIG. 10, where the covering component 104 is loose about a portion 117 of the inverted section 114 that opposes at least a portion of the laterally facing skirt 112, and is tighter against the portion 119 of the inverted section 114 that opposes at least of portion of the occlusive face 110. In general, not attaching the covering component 104 to at least a portion of the inverted section 114 can provide a degree of freedom for the covering component, and allow it to move freely to avoid binding as the device frame expands and collapses, for example.

In some embodiments, both the first hub member 108 and the second hub member 116 are covered by the covering component 104. In some embodiments, one or both of the first hub member 108 and the second hub member 116 are not covered by the covering component 104. With reference to FIGS. 1B and 1C, device 100 is shown carried on a mandrel 120 for ease of illustration, along with a catheter or sheath 124, into which the device 100 may be loaded. In actual use, mandrel 120 would be replaced by a delivery component, for example.

In some embodiments, the first hub member 108 and the second hub member 116 are coupled together by a coupling element. The coupling element may be an adhesive, for example, such as fluorinated ethylene propylene (FEP). In other examples, the coupling element may be a weld or a mechanical coupling element, such as a joint, rivet (e.g., a barbell rivet), or various types of catch members. When coupled together, the first hub member 108 and the second hub member 116 may be substantially aligned along a longitudinal axis of the device frame. In some examples, the first hub member 108 and the second hub member 116 may be concentrically aligned along the longitudinal axis of the device frame. In some embodiments, the coupling element can eliminate relative motion between the first hub member 108 and the second hub member 116. Eliminating the relative motion between the hub members can reduce or negate a straightening effect on the elongate members in some examples, which can be beneficial for loading or deploying the device, in some cases.

By coupling the first hub member 108 and the second hub member 116 together, the struts of the occlusive face 110 are placed back-to-back with struts of the portion 119 of the inverted section 114 that opposes at least a portion of the occlusive face 110. This may balance rotational forces associated with the elongate members 102 of the device 100, which may be advantageous for deployment of the device 100. The rotational forces may be balanced, for example, because the inverted section 114 is inverted within the device, as will be discussed further below, so that the distal-facing portion of the device forms a cupped shape, as can be seen with reference to FIG. 10.

Figure 3A:
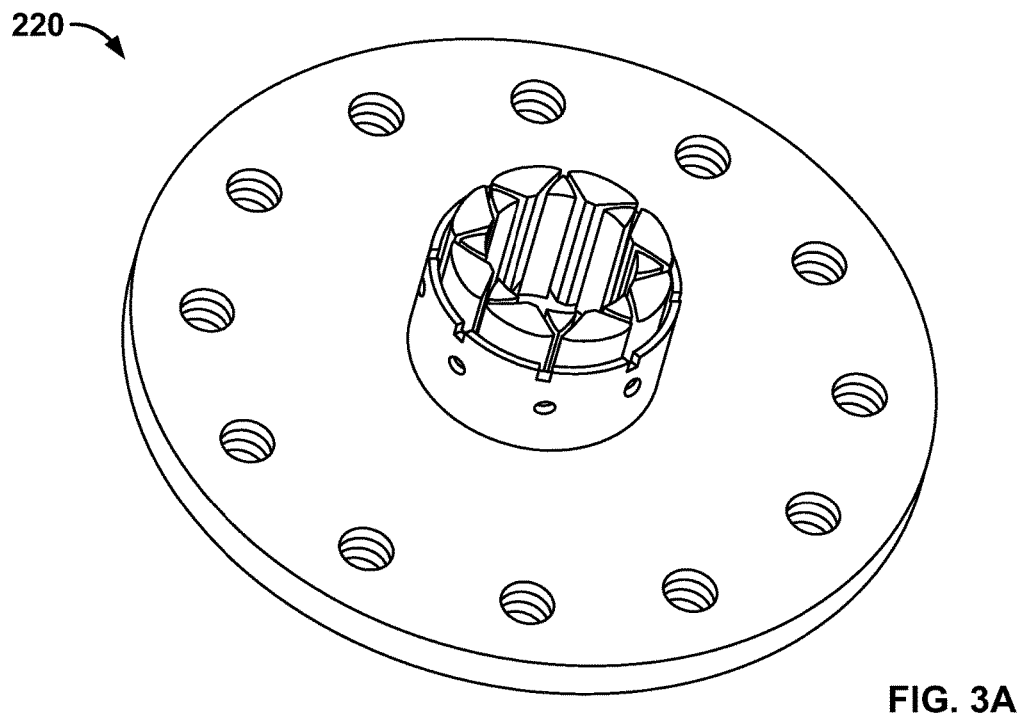
FIG. 3A is a perspective view of an example jig apparatus.

For devices having elongate members 102 comprised of wires, the elongate members may be wound, for example, using a winding jig or a modular tool and by guiding each elongate member 102 along a winding path defined by one or more pins, bars, blocks, channels, or feature-defining jig components to create the features of the device as desired. When using a jig apparatus, for example, the elongate members may follow a predetermined path as defined by the jig apparatus or determined by features of the jig apparatus. FIG. 3A is a perspective view of an example jig apparatus 220. Jig apparatus 220 can be used to wind an eight-wire occlusive device. For devices that include a different number of wires, jig apparatus's similar to jig 220 but with appropriate modifications, can be used.

Figure 3B:
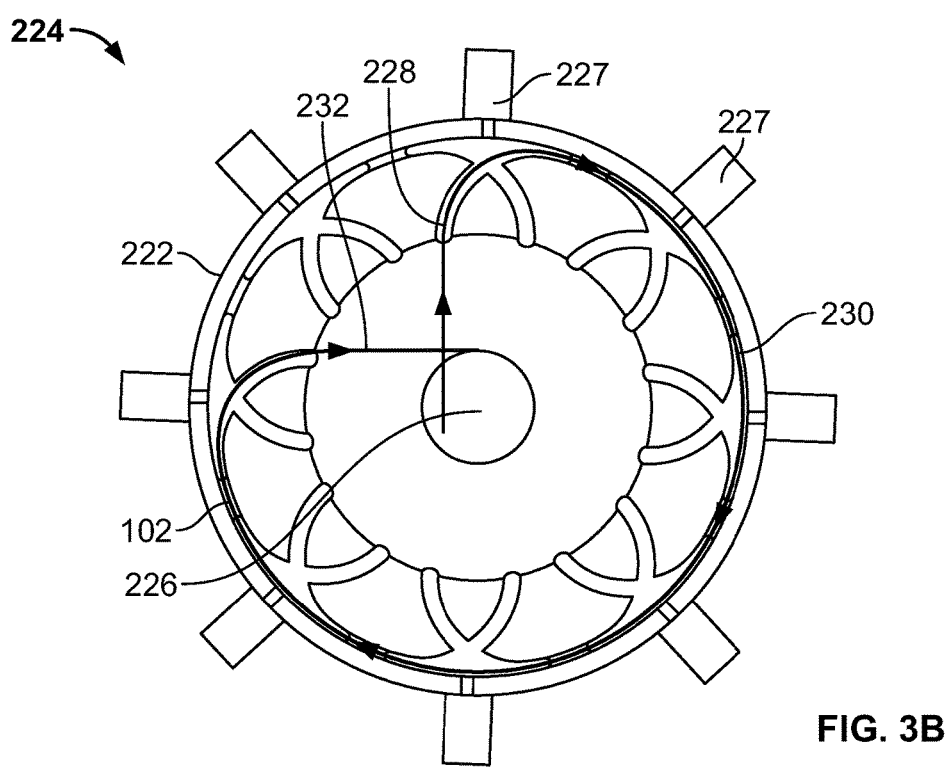
FIG. 3B is a top view of an example jig apparatus, and shows a wind pattern that can be used to wind a device frame.

FIG. 3B is a top view of an example jig apparatus 222, and shows a wind pattern 224 that can be used to wind an occlusive device. Jig apparatus 222 is similar to jig 220, but includes additional features 227 (e.g., pins) that can be optionally used with one or more of the winding path to provide one or more anchors for the device. An elongate member 102 can initially be wound in a coiled fashion around a pin or mandrel (not shown) at the center 226 of the jig 222, to create a first eyelet (which may be first hub member 108 in some embodiments). The elongate member 102 can then be wound radially (see portion 228) and through a path in the jig 222. The elongate member 102 is generally wound in a rotational direction (clockwise in this example), as indicated by portion 230, and finally is wound radially back to the center 226 of the jig (see portion 232) and coiled around the pin or mandrel to create a second eyelet (which may be second hub member 116 in some embodiments). As can be seen in FIG. 3B, an angle defined between the elongate member's exit path from the first eyelet and entry path to the second eyelet is about 270°. In some examples, the angle may be in a range of about 255° to about 285°. In some examples, the angle may be in a range of about 225° to about 315°. In some examples, the angle may be in a range of about 140° to about 360°. Each of the elongate member's 102 can be similarly wound on the jig 22, and the above-described angle may be about the same for each of the wires of the device. In general, a length of the device may be tuned based in part on the winding angle defined between the elongate member's exit path from the first eyelet and entry path to the second eyelet. For example, for devices having a longer skirt length, angles of about 360° or longer can be used. For devices having a shorter skirt length, angles of about 140°-200° can be used.

Figure 4:
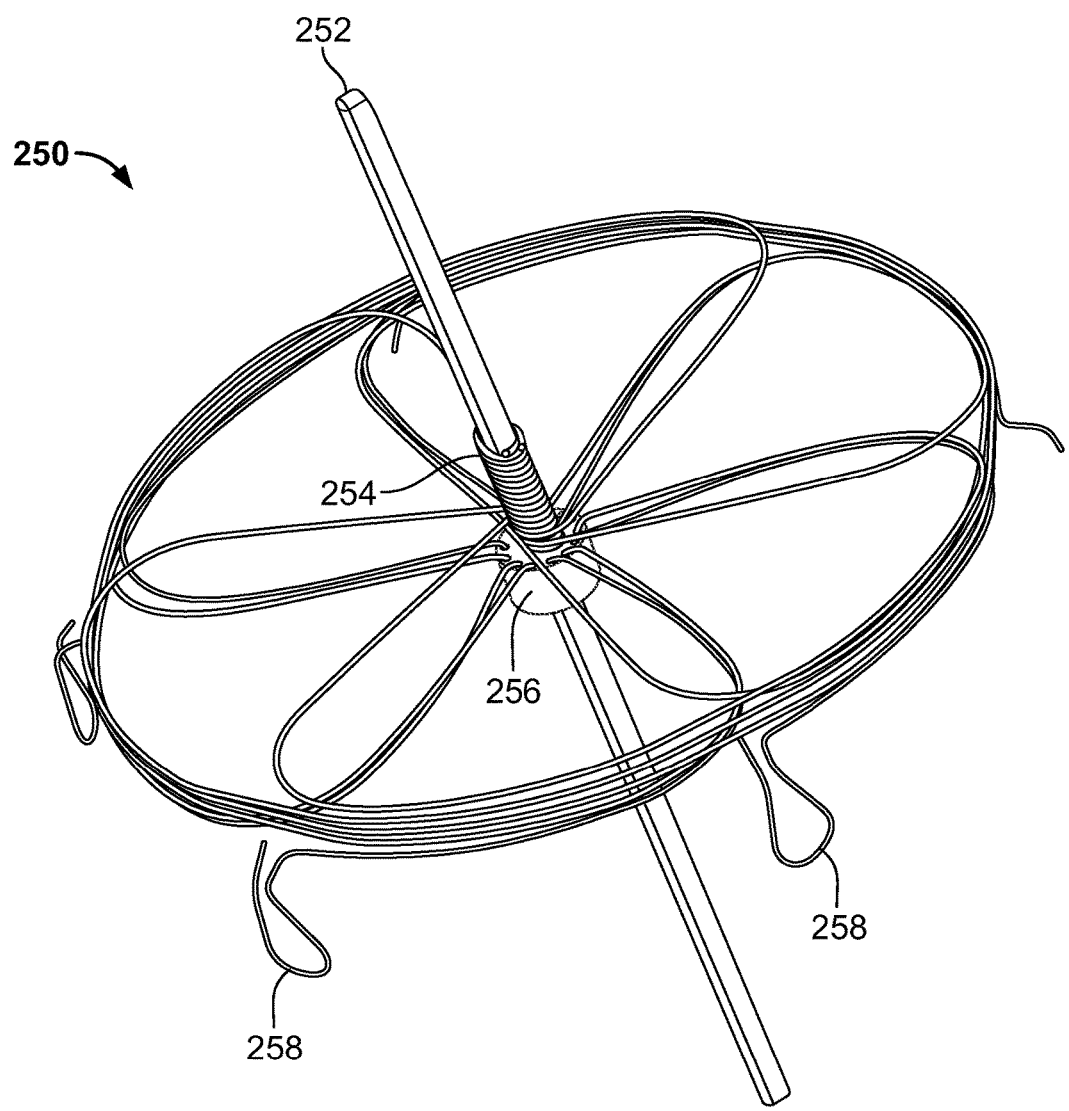
FIG. 4 is a perspective view of an example device frame.

FIG. 4 is a perspective view of an example device frame 250 carried by a mandrel 252 after the mandrel 252 and frame has been removed from a winding jig. Frame 250 includes an eyelet 254 as a second hub member 116 and a ring member 256 as a first hub member 108. Various types of ring members that can be used as either first or second hub members of the occlusive devices discussed herein will be described in more detail below.

Device frame 250 generally includes six wires that form the device frame 250. Device frame 250 also includes six anchor features 258, which in this example are formed by six additional wires. As such, the device frame 250 of FIG. 4 includes a portion of the frame that is two-filar, and a portion of the frame that is single-filar. Although frame 250 would be wound on a jig designed for frames with six wires, the eight-wire example jig assembly 224 of FIG. 3B illustrates features 227, around which wires can be wound to provide device frame anchor features similar to anchor features 258. For example, a pair of wires including a frame wire and an anchor wire may extend from first hub member 108 (e.g., a first eyelet). The frame wire may traverse the path shown in FIG. 3B, and the anchor wire may initially traverse the same path, but during portion 230 may instead be would around a feature 227 and terminated.

Figure 5A:
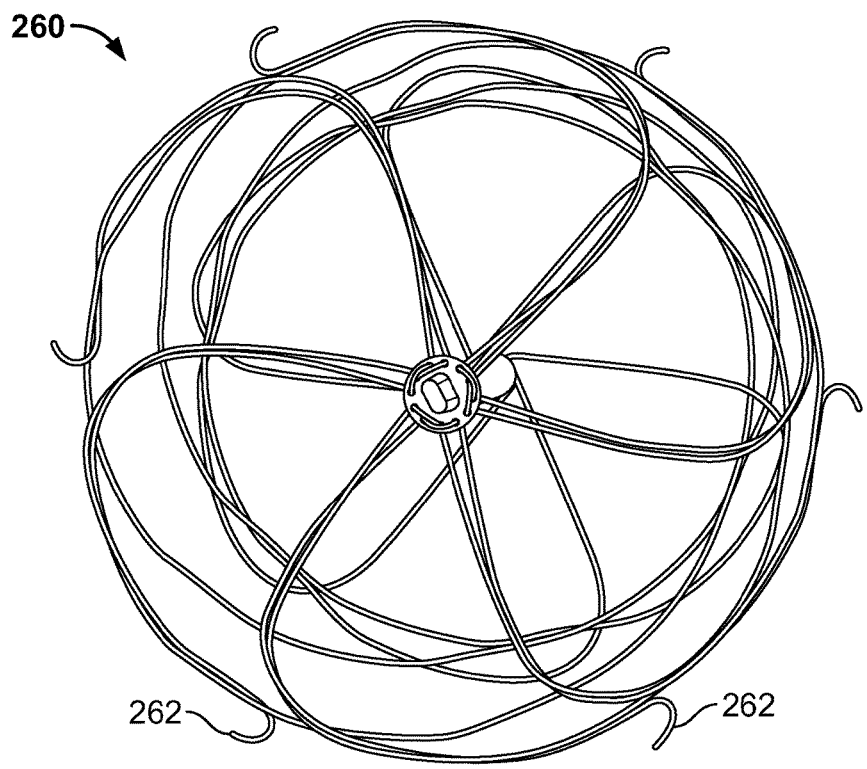
FIG. 5A is a perspective view of an example device frame that includes example anchors having a hook shape.
Figure 5B:
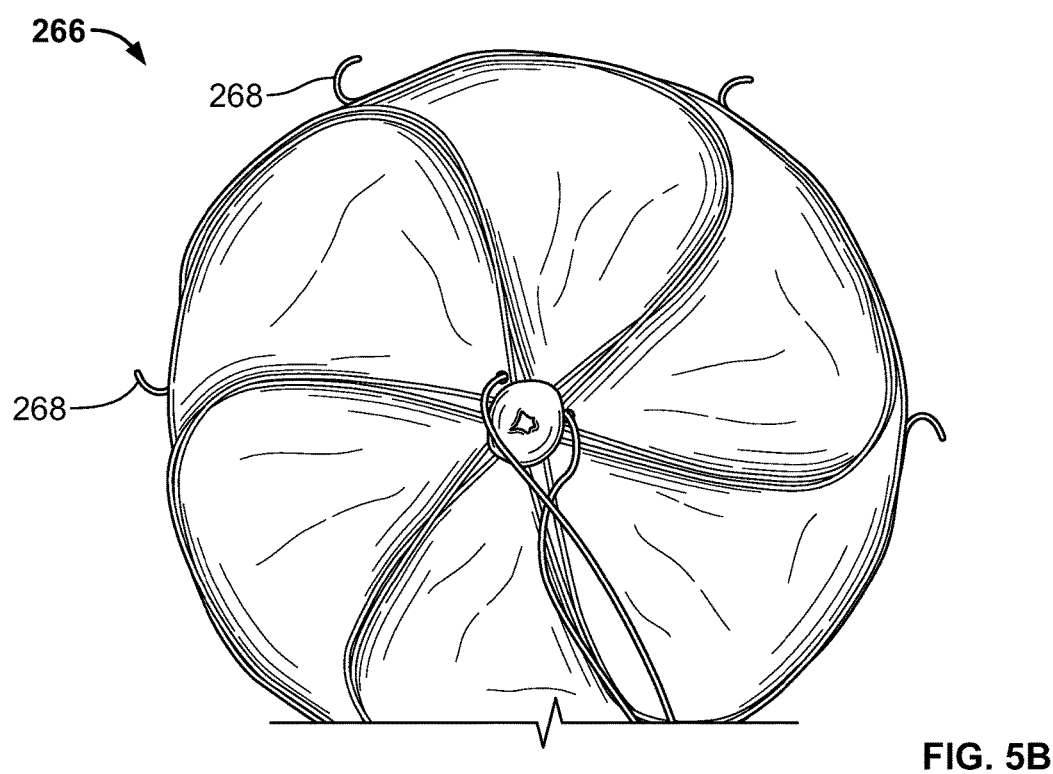
FIG. 5B is a front view of an example occlusive device.

The anchor features can take various forms. FIG. 5A is a perspective view of an example device frame 260 that includes example anchors 262 having a hook shape. FIG. 5B is a front view of an example occlusive device 266, and shows how the anchors 268 can extend from the laterally facing skirt for engaging tissue of a wall of the space to be occluded (e.g., the wall of an LAA).

In some embodiments, device frames described herein can be created using a process that includes a single heat set operation, where the shape memory elongate members 102 are heated for a predetermined time and according to a predetermined heating profile while configured in a predetermined orientation to heat set the elongate members as desired. In some embodiments, device frames described herein can be created using a process that includes two heat set operations. For example, a first heat set operation can be provided to define portions of the occlusive face 110 and inverted section 116 of the device, and a second heat set operation can be used to define the laterally facing skirt 112 and portions of the inverted section 116. For example, the second heat set operation can be used to provide the cupped feature of the device frames described herein.

Figure 6:
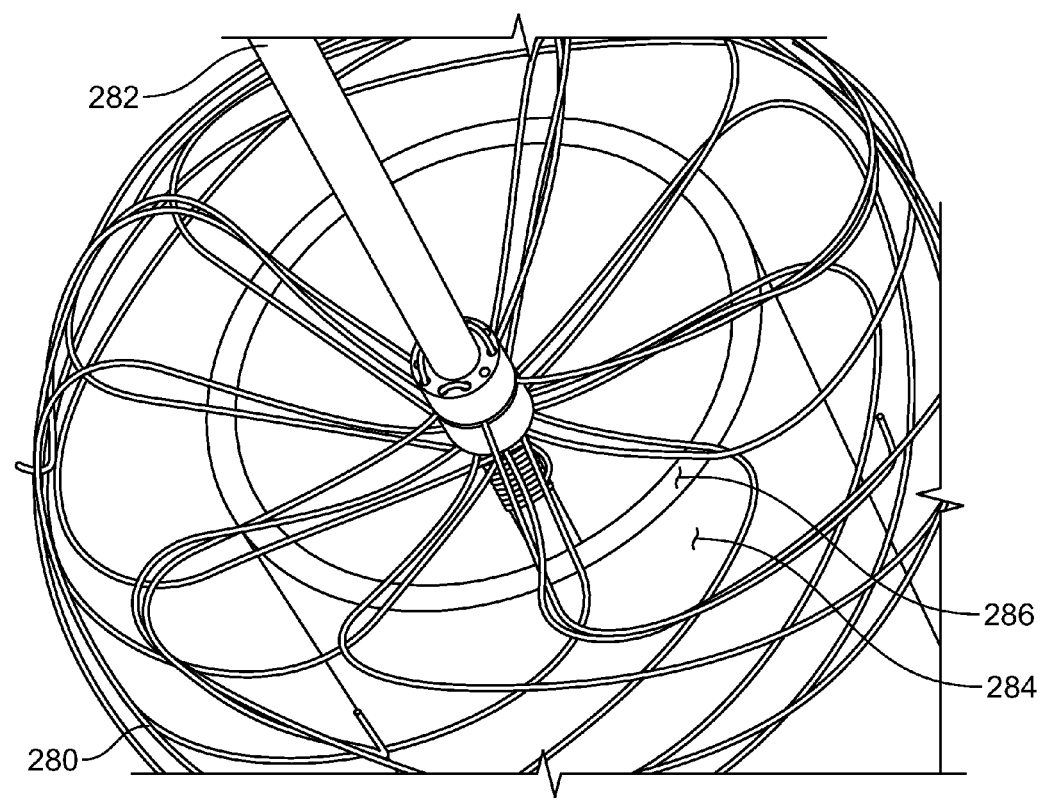
FIG. 6 illustrates an example manufacturing operation that can provide the cupped feature of the device frames discussed herein.

Referring again to device frame 250 of FIG. 4, the frame 250 can be heat set using a first heat set operation. Following a first heat set operation, FIG. 6 illustrates an example manufacturing operation that can provide the cupped feature of the device frames discussed herein. A device frame 280, carried by a mandrel 282 and initially in a generally flat orientation similar to the orientation of frame 250 of FIG. 4, is pushed a predetermined distance into an interior space of manufacturing pipe or tube 284. For example, the mandrel 282, to which the first and second hub members 108, 116 of the frame 280 are mounted, can be centered within the manufacturing pipe or tube 284 so that the (generally flat) frame 280 is flush with an edge 286 of the manufacturing pipe or tube 284. The mandrel may then be pushed a predetermined distance into the tube 284, which may cause the first and second hub members 108, 116 to at least partially enter the interior space of the tube 284. The frame 28 has a diameter that is larger than the diameter of the tube 284, and the laterally facing skirt 112 is formed as the excess frame length is pushed down by the tube 284 while the mandrel 282 is advanced into the tube 284. In some embodiments, the mandrel 282 is pushed into the tube 284 about 0.090". In some examples, the mandrel may be advanced into the tube 284 a distance in a range of about 0.088" to about 0.092". In some examples, the mandrel may be advanced into the tube 284 a distance in a range of about 0.085" to about 0.095". When the mandrel 282 has been appropriately advanced into the tube 284 to create the laterally facing skirt 112, a second heat set operation can be performed on the frame 280. Although the description above describes two separate heat set operations, in some implementations a single heat set operation can be performed.

Figure 7:
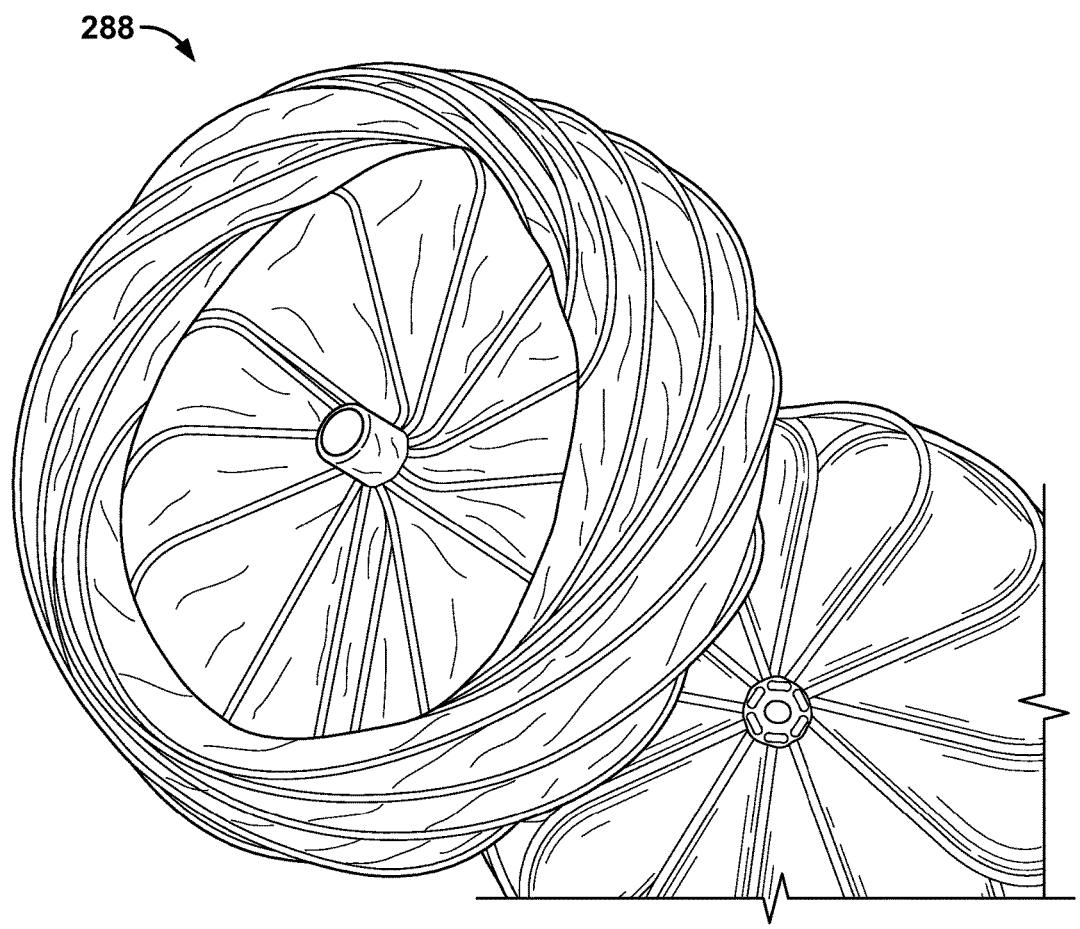
FIG. 7 is a perspective view of a distal portion of an example occlusive device that illustrates the cupped feature of the device.

FIG. 7 is a perspective view of a distal portion of an example occlusive device 288 that illustrates the cupped feature of the device.

Following the second heat set operation, the device frame can be removed from the tube 284 and prepared for attachment of the covering component 104. The first and second hub members 108 and 116 can be separated on the mandrel to elongate the device frame. An adhesive (e.g., FEP) can be applied to portions of the elongate members. As described above, the covering component 104 is attached to the occlusive face 110, the laterally facing skirt 112, and the portion of the inverted section that opposes the profile of at least a portion of the occlusive face. The covering component 104 is not attached to the portion of the inverted section that generally opposes the profile of at least a portion of the laterally facing skirt. As such, the frame can be prepared so that portions of the elongate members to which the covering component should attach are coated with adhesive, and portions or the frame to which the covering component should not attach are not coated with adhesive. In some examples, the entire frame can be initially coated with adhesive, and selected portions of the adhesive can be removed (as by vacuuming). In some examples, only those portions of the frame to which the covering component should attach are coated with adhesive.

Figure 8:
FIG. 8 is a perspective view of an example device frame elongated along a mandrel and with adhesive applied to portions of the frame to which the covering component will attach.

FIG. 8 is a perspective view of an example device frame 290, elongated along a mandrel and with adhesive applied to portions of the frame 290 to which the covering component will attach. In some examples, a hypotube can be used to separate the first and second hub members 108 and 116 to elongate the device on the mandrel. The covering component 104 may then be attached to portions of the frame 290 via the adhesive. In some examples, a membranous film is wrapped onto the frame to provide the covering component 104. In some examples, a membranous bag element is positioned onto the frame to provide the covering component 104.

Following application of the covering component, the first and second hub members 108 and 116 may be coupled together by a coupling element. The coupling element may be an adhesive, such as FEP, in some examples. In other examples, the coupling element may be a weld or a mechanical coupling element, such as a joint, rivet (e.g., a barbell rivet), or various types of catch members. The coupling element may substantially align the first hub member 108 and the second hub member 116 along a longitudinal axis of the device frame. In some examples, the first hub member 108 and the second hub member 116 may be concentrically aligned along the longitudinal axis of the device frame.

Figure 9:
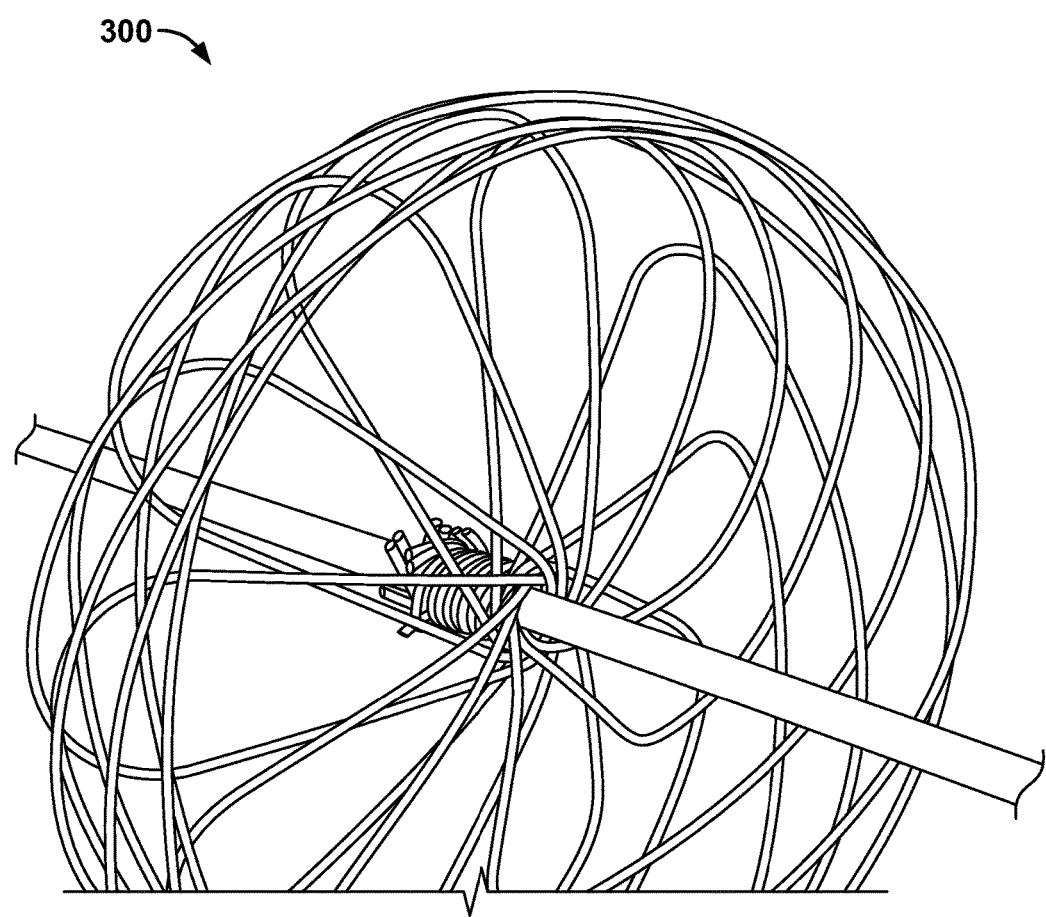
FIG. 9 is a perspective view of an example device frame.

FIG. 9 is a perspective view of an example device frame 300, where the second hub member is arranged concentrically within (e.g., nested within) the first hub member. In this example, each of first hub member and second hub member are eyelets. In some examples, a first mandrel having a first diameter can be used in winding the first eyelet and a second mandrel having a second (smaller, in this example) can be used in winding the second eyelet. In other examples, the first hub member can be arranged concentrically within the second hub member.

Figure 10:
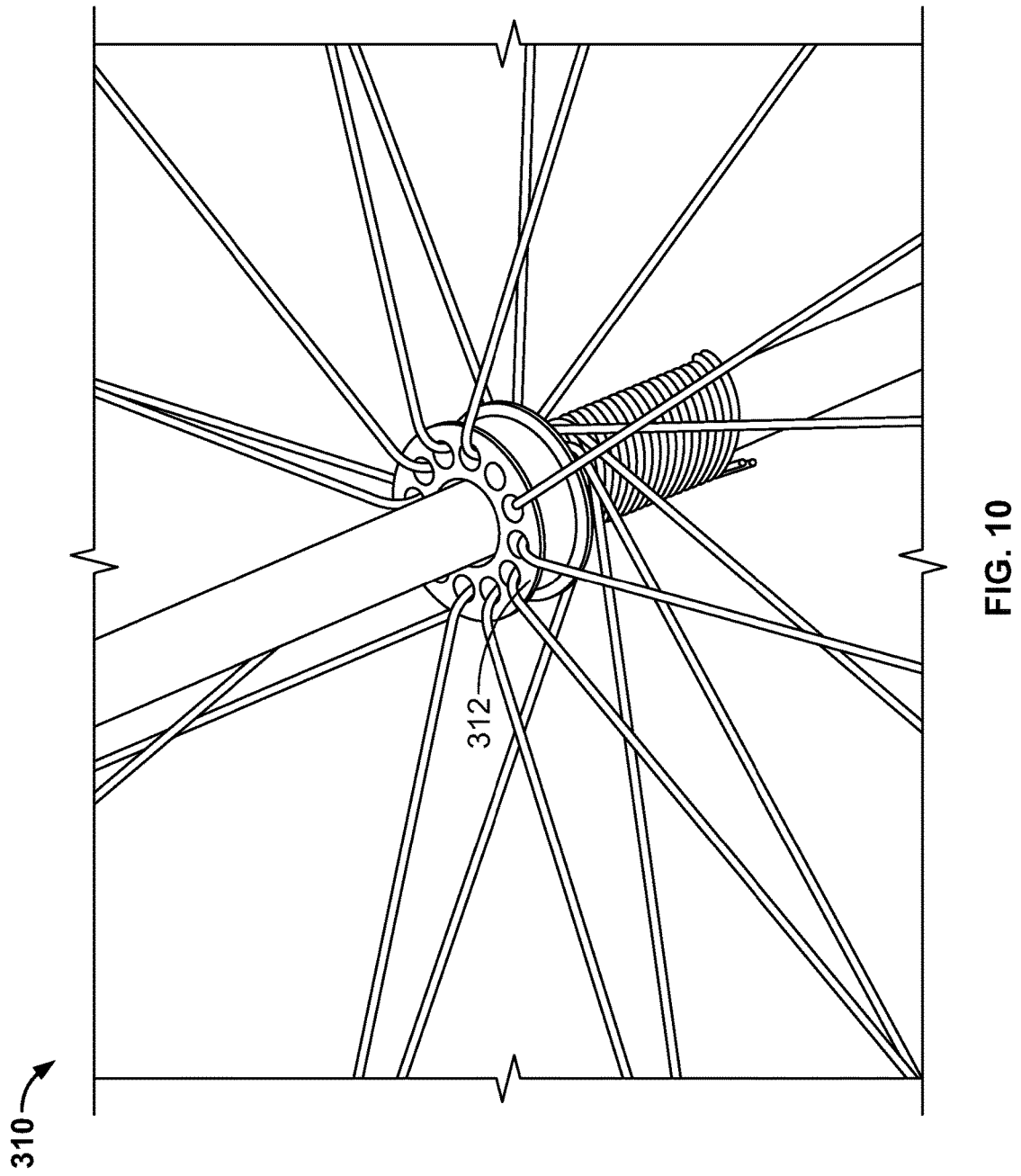
FIG. 10 is a perspective view of a portion of an example device frame, and an example ring member.

FIG. 10 is a perspective view of a portion of an example device frame 310, and an example ring member 312. Ring member 312 generally has a ring shape, and includes a plurality of holes longitudinally defined through a wall of the ring member 312. The ring member 312 may aggregate ends of the elongate members, which may pass through the holes of the ring member 312, or, in some embodiments, terminate within the ring member 312.

FIGS. 11-17 are drawn to highlight particular occlusive device frame features that can be incorporated into the designs of the occlusive devices provided herein. For example, in some of the figures the designs of the hub members and/or other frame features are highlighted. It should be understood that one or more of the features that are highlighted in these figures can be included in any of the occlusive devices described elsewhere herein, and that such features (and other features described herein) can be mixed and matched to create hybrid designs that are entirely within the scope of this disclosure. In these figures, no covering component or only partial covering component is shown and some portions of the frames are not shown so that the highlighted frame features are more readily visible. It should be understood that the occlusive devices of FIGS. 11-17 can be combined with a covering component in some embodiments. The covering component can share any or all of the features, characteristics, properties, etc. as described above in reference to the covering component 104 and/or any other exemplary covering components described herein.

Figure 11:
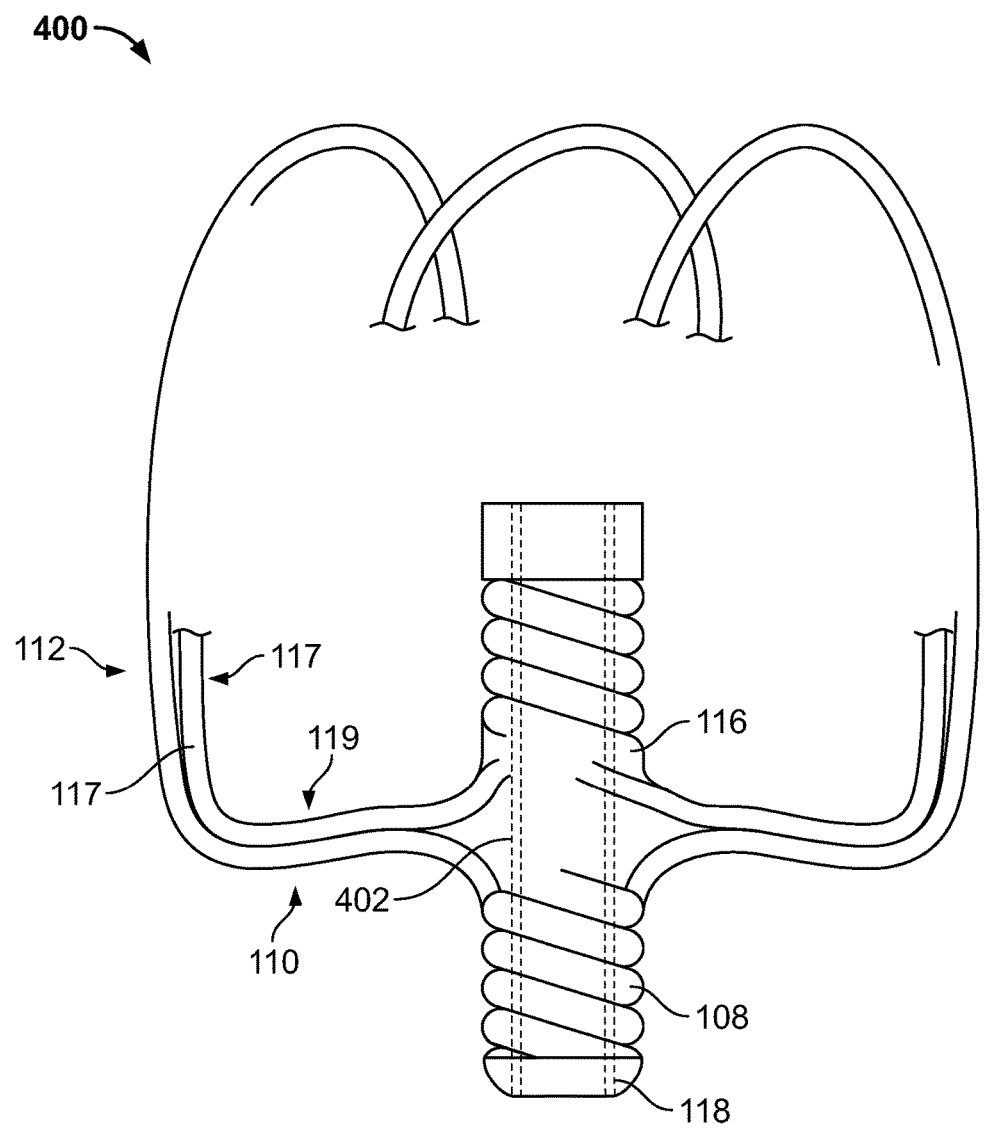
FIG. 11 is a conceptual diagram of a portion of an example device frame.

FIG. 11 is a conceptual diagram of a portion of an example device frame 400 of the type discussed herein. Frame 400 shows how the portion 117 of the inverted section opposes the laterally facing skirt 112, and how the portion 119 of the inverted section opposes the occlusive face 110. A union joint 402 couples the first hub member 108 to the second hub member 116, and aligns them along a longitudinal axis of the device. The joint 402 may hold the hub members 108 and 116 axially, while allowing rotational movement therebetween. The hub members 108 and 116 are eyelets in this example. A cap 118 of the joint may be rounded, for example.

Figure 12:
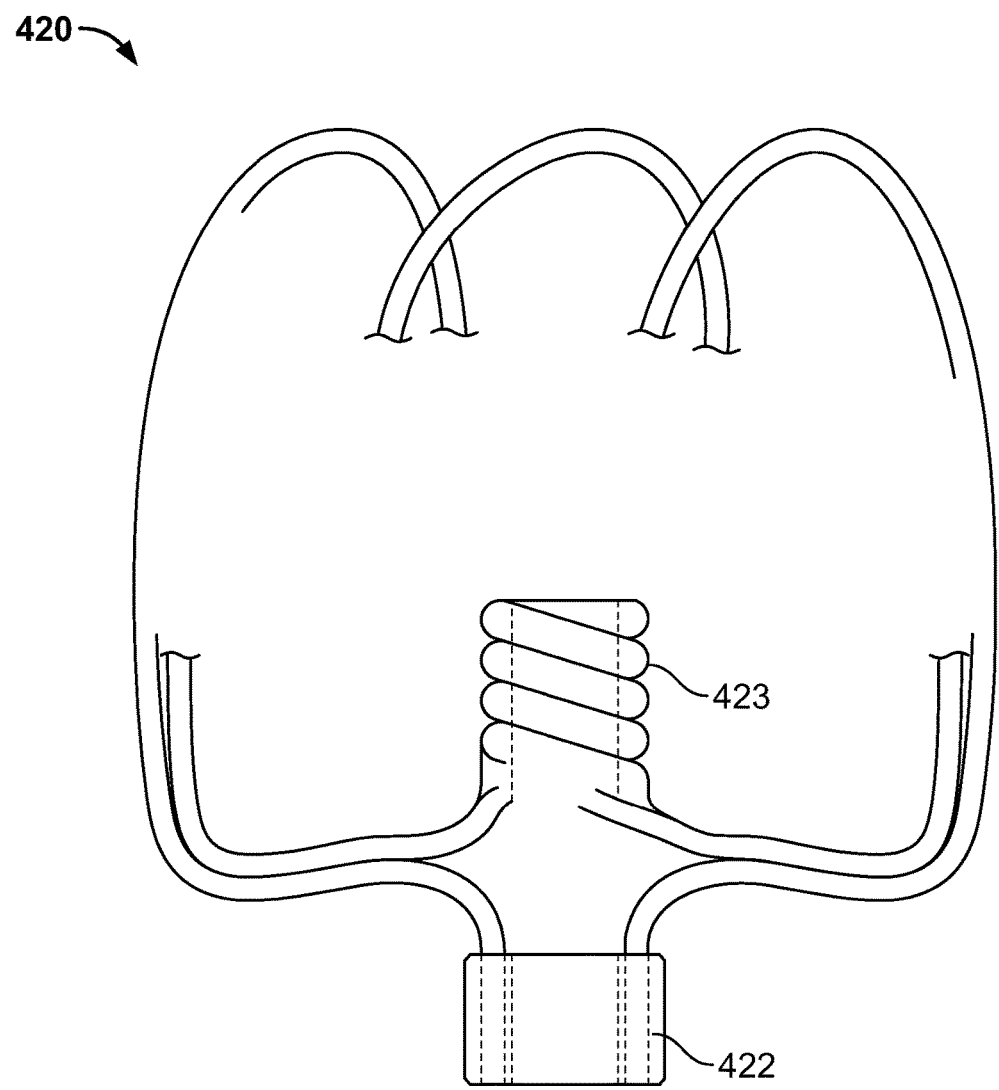
FIG. 12 is a conceptual diagram of a portion of another example device frame.

FIG. 12 is a conceptual diagram of a portion of an example device frame 420 of the type discussed herein. The frame includes a ring member 422 as the first hub member. The second hub member is an eyelet 423 in the depicted example. In the depicted embodiment, the ring member 422 and the eyelet 423 are not directly coupled to each other. However, in some embodiments the ring member 422 and the eyelet 423 are directly coupled to each other. Ring member 422 may provide additional termination points for anchor attachment wires. As can be seen in FIG. 12, the elongate members generally enter ring member 422 along an axial direction, whereas the wires that enter an eyelet (see FIG. 11) may do so tangentially in a helically wound direction. In some examples, the ring member 422 may include a threaded feature (not shown) for attaching a delivery catheter, for example.

Figure 13:
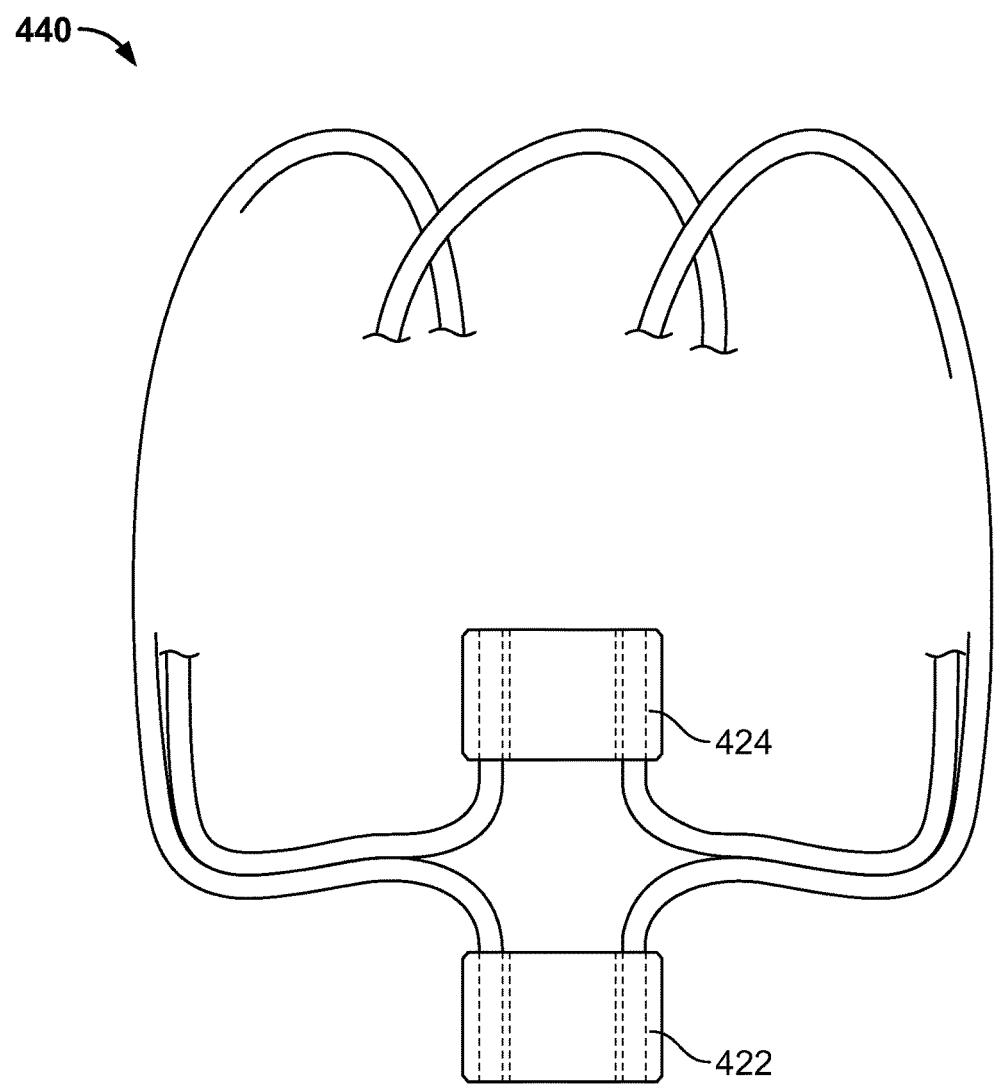
FIG. 13 is a conceptual diagram of a portion of yet another example device frame.

FIG. 13 is a conceptual diagram of a portion of an example device frame 440 of the type discussed herein. The frame includes two ring members 422 and 424, corresponding to the first and second hub members, respectively. The elongate members may be terminated at the hub members in various ways. For example, the elongate members may be looped through the hub members. The elongate members may alternatively be welded, or attached with adhesive.

Figure 14:
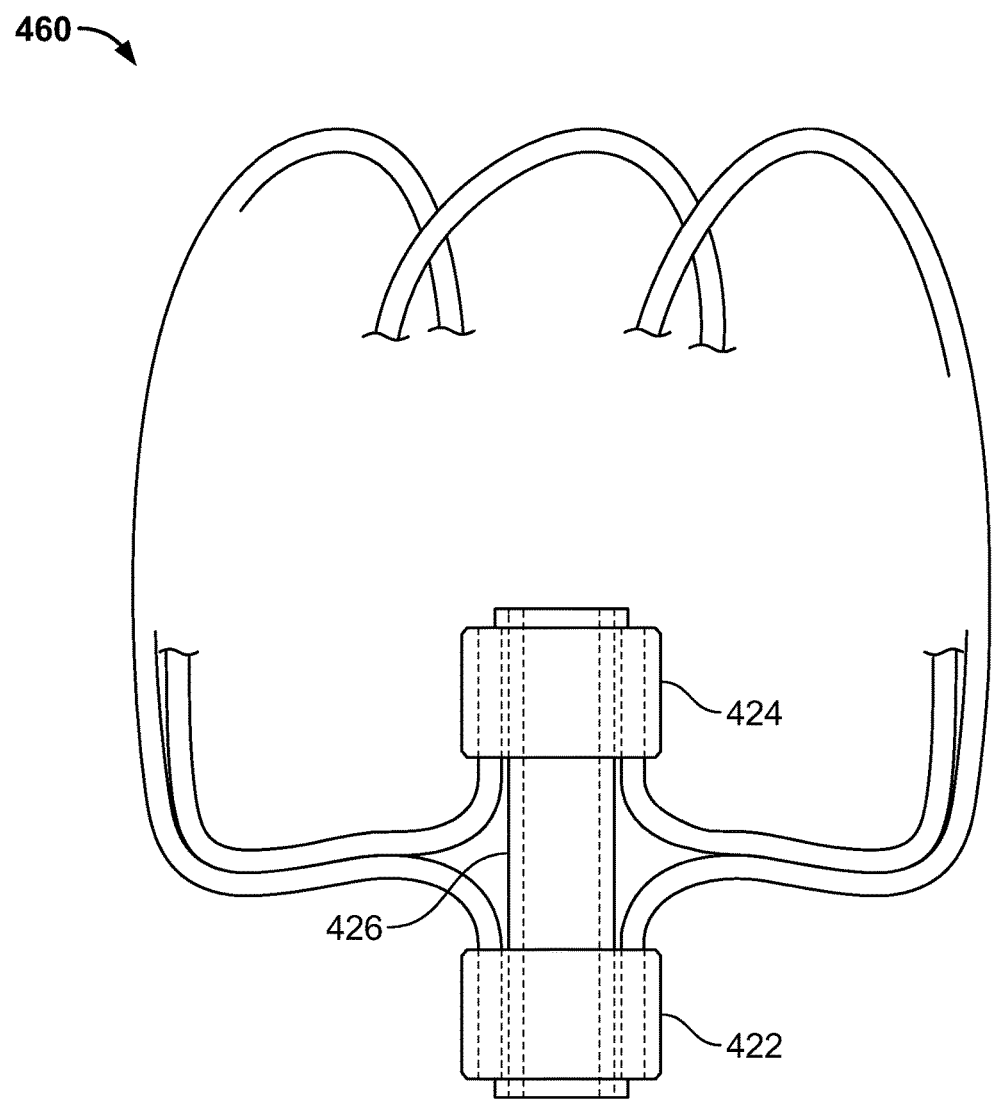
FIG. 14 is a conceptual diagram of a portion of yet another example device frame.

FIG. 14 is a conceptual diagram of a portion of an example device frame 460 of the type discussed herein. The frame includes two ring members 422 and 424, corresponding to the first and second hub members, respectively coupled together by a joint 426. In some examples, the joint 426 may be configured to allow ring members 422 and 424 to spin relative to one another. In some examples, the joint 426 may be configured to not allow the ring members 422 and 424 to spin relative to one another.

Figure 15:
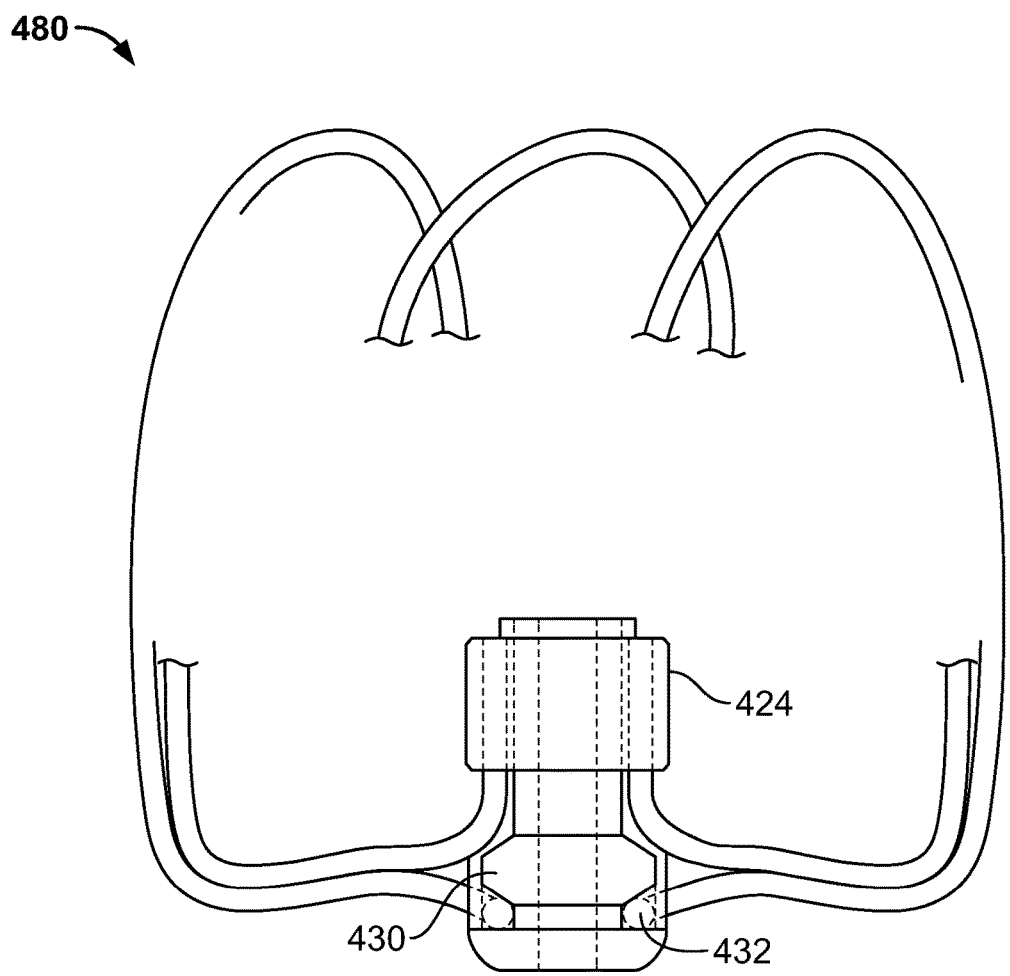
FIG. 15 is a conceptual diagram of a portion of yet another example device frame.

FIG. 15 is a conceptual diagram of a portion of an example device frame 480 of the type discussed herein. The frame includes a pivot hub component 430 of the type described in the provisional application titled "Joint Assembly for Medical Devices," having inventors Coby C. Larsen, Steven J. Masters, and Thomas R. McDaniel, filed on 16 Nov. 2012, and which is herein incorporated by reference in its entirety for all purposes. Ends of the elongate members that terminate in the pivot hub component 430 have ball ends 432 that are received by the hub 430 with socket or slotted features, and allow the elongate members to pivot. In the depicted embodiment, the inner hub member comprises a ring member 424. In some embodiments, the inner hub member may be another type of hub member such as, but not limited to, an eyelet, a tube portion, and the like.

Figure 16:
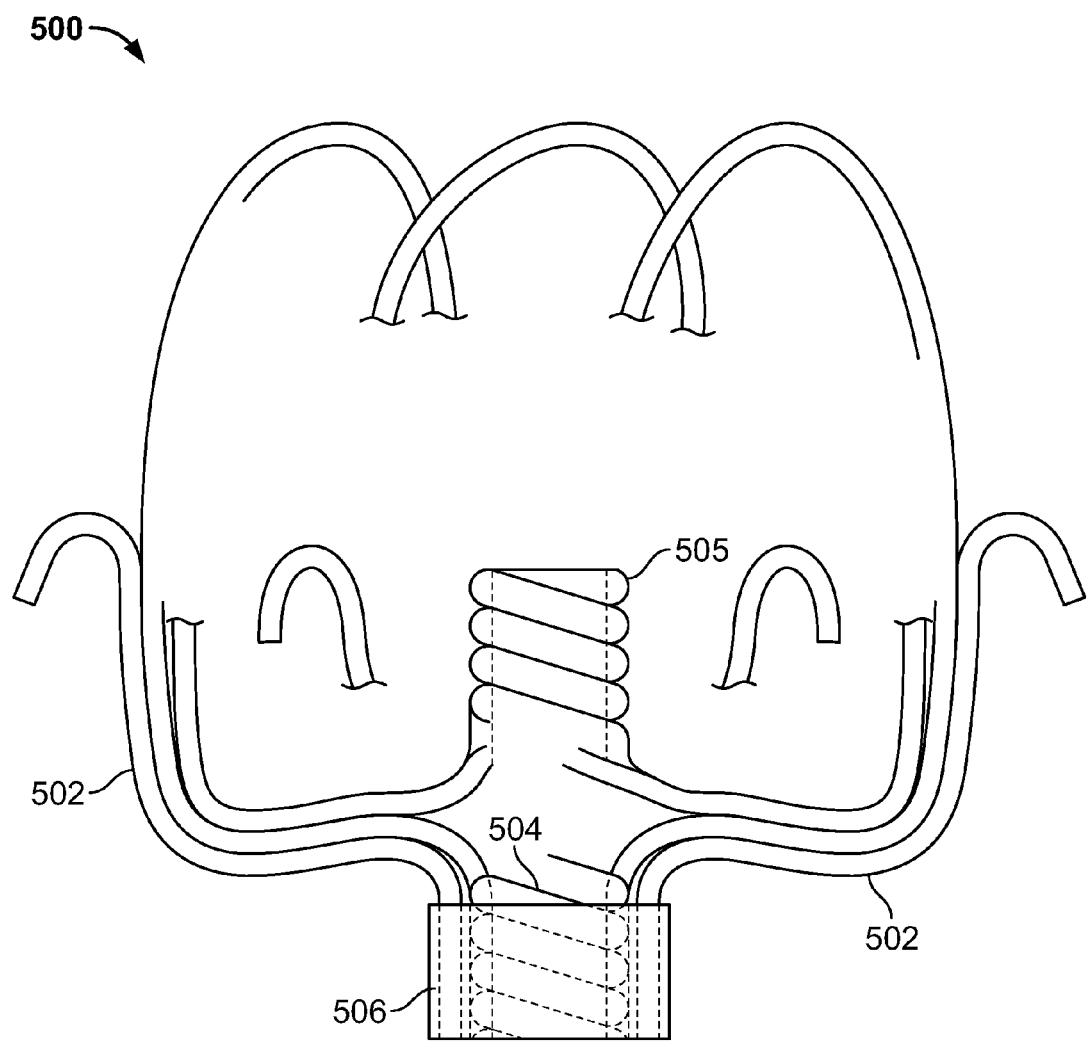
FIG. 16 is a conceptual diagram of a portion of yet another example device frame.

FIG. 16 is a conceptual diagram of a portion of an example device frame 500 of the type discussed herein. An anchor assembly 502 is included, where the anchor assembly 502 uses separate elongate members from those used to form the occlusion frame of the device 500. The elongate members of the occlusion frame are terminated in an eyelet 504, which acts as the first hub member, while the anchor elongate members are terminated in a hub or ring component 506, which may be attached to eyelet 504 by adhesive, welded joint, or other mechanical structures (e.g., dog-bone joint). In the depicted embodiment, the inner hub member comprises an eyelet 505. In some embodiments, the inner hub member may be another type of hub member such as, but not limited to, a ring member, a tube portion, and the like. The anchor assembly 502 can use wires of different size, shape, or material than the wires of the occlusion frame, in some implementations. In some embodiments, the anchor assembly 502 can be formed using a cut-tube process as described elsewhere herein.

Figure 17:
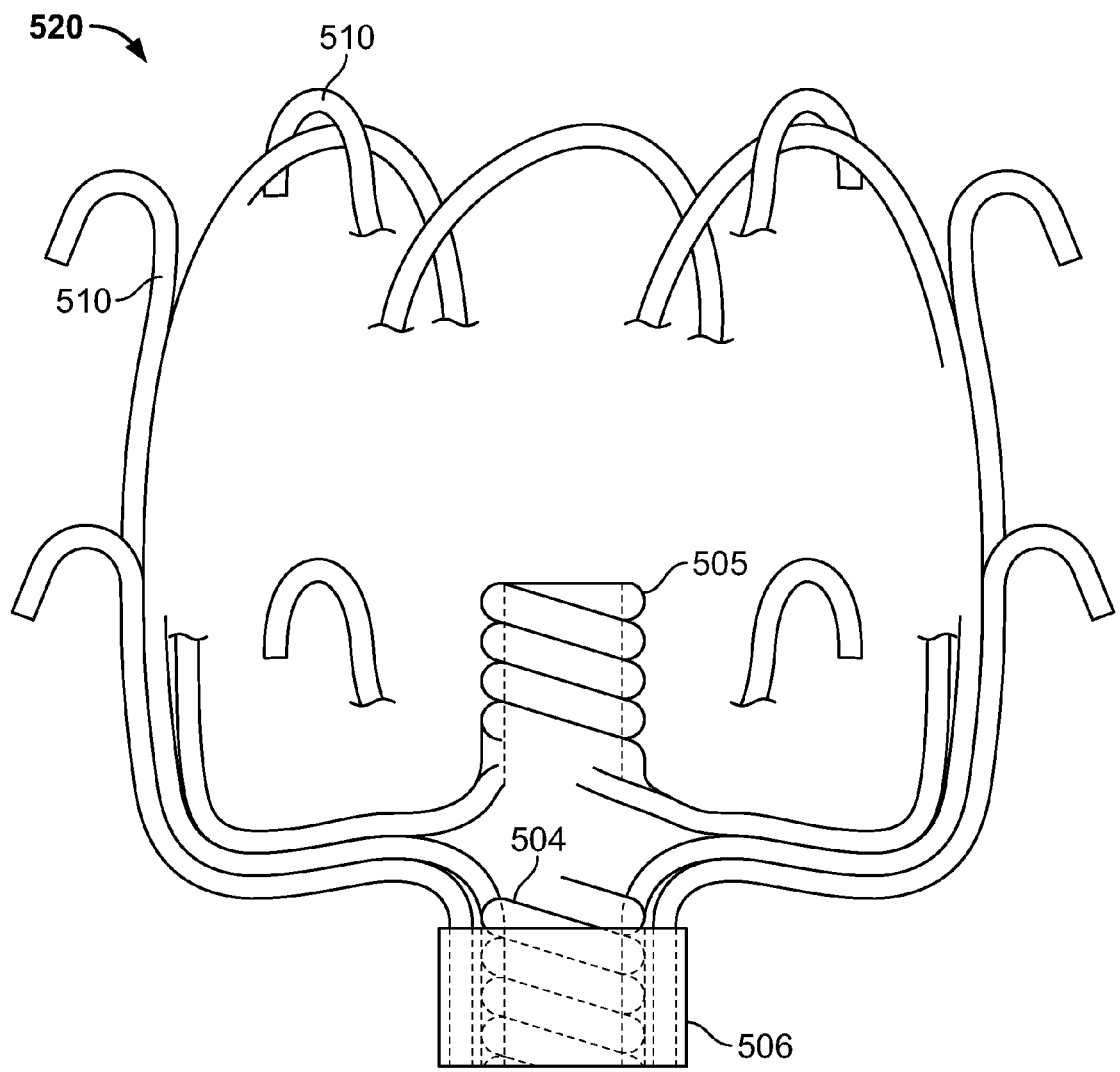
FIG. 17 is a conceptual diagram of a portion of yet another example device frame.

FIG. 17 is a conceptual diagram of a portion of a device frame 520 that is similar to the frame 500 of FIG. 16, but includes additional anchors 510 located near the distal end of the device, which may allow for earlier anchoring during deployment of the device, for example. The anchors 510 may terminate at the same hub or ring component 506, for example. In the depicted embodiment, the inner hub member comprises an eyelet 505. In some embodiments, the inner hub member may be another type of hub member such as, but not limited to, a ring member, a tube portion, and the like. The anchor assembly 510 can use wires of different size, shape, or material than the wires of the occlusion frame, in some implementations. In some embodiments, the anchor assembly 510 can be formed using a cut-tube process as described elsewhere herein.

Figure 18A:
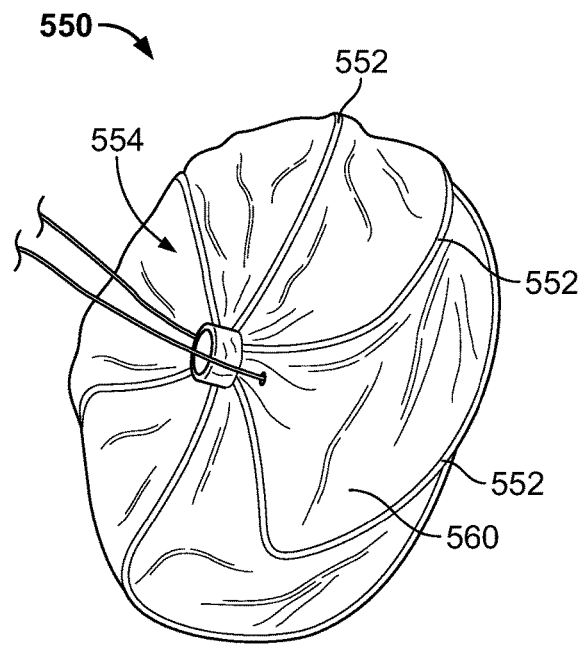
FIGS. 18A, 18B, and 18C are perspective views of an example device that includes a device frame having elongate members that are formed from a tube of material.
Figure 18B:
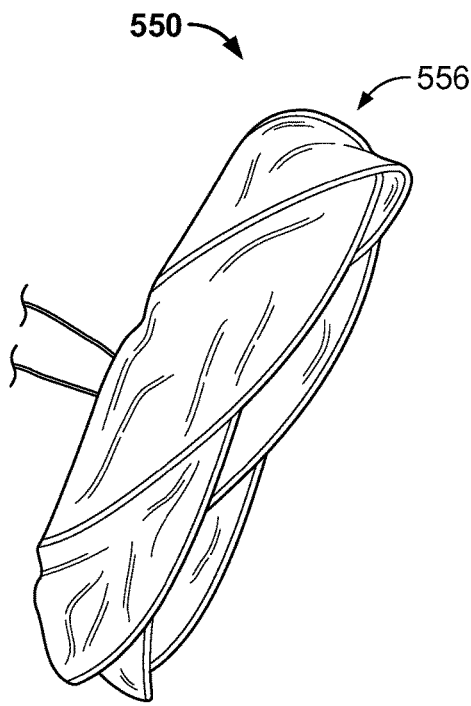
Figure 18C:
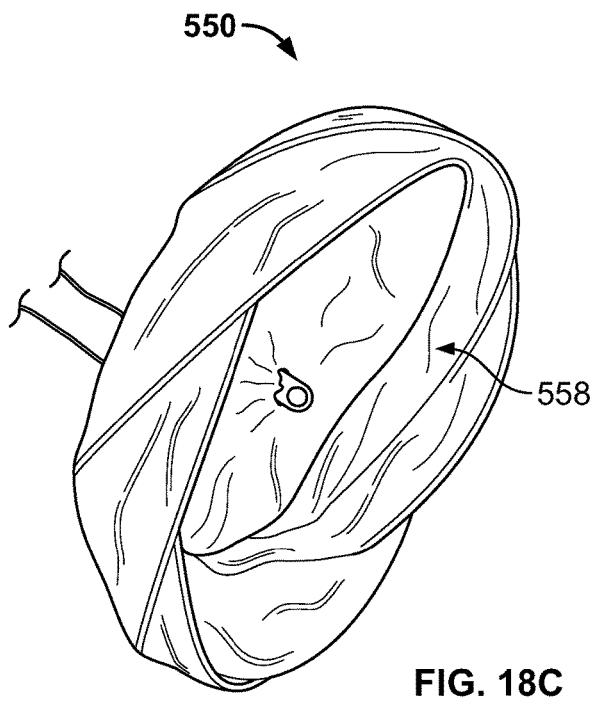

FIGS. 18A, 18B, and 18C are perspective views of an example device 550 that includes a device frame having elongate members 552 that are formed by cutting (e.g., laser cutting) and expanding a tube of material. In this example, the device 550 includes six elongate members 552. In general, the frame of device 550 has a shape similar to other occlusive device frames discussed herein. For example, a face section 554, laterally facing skirt section 556, and inverted section 558 of the device frame can be seen in the figures, despite the presence a covering component 560.

Figure 19:
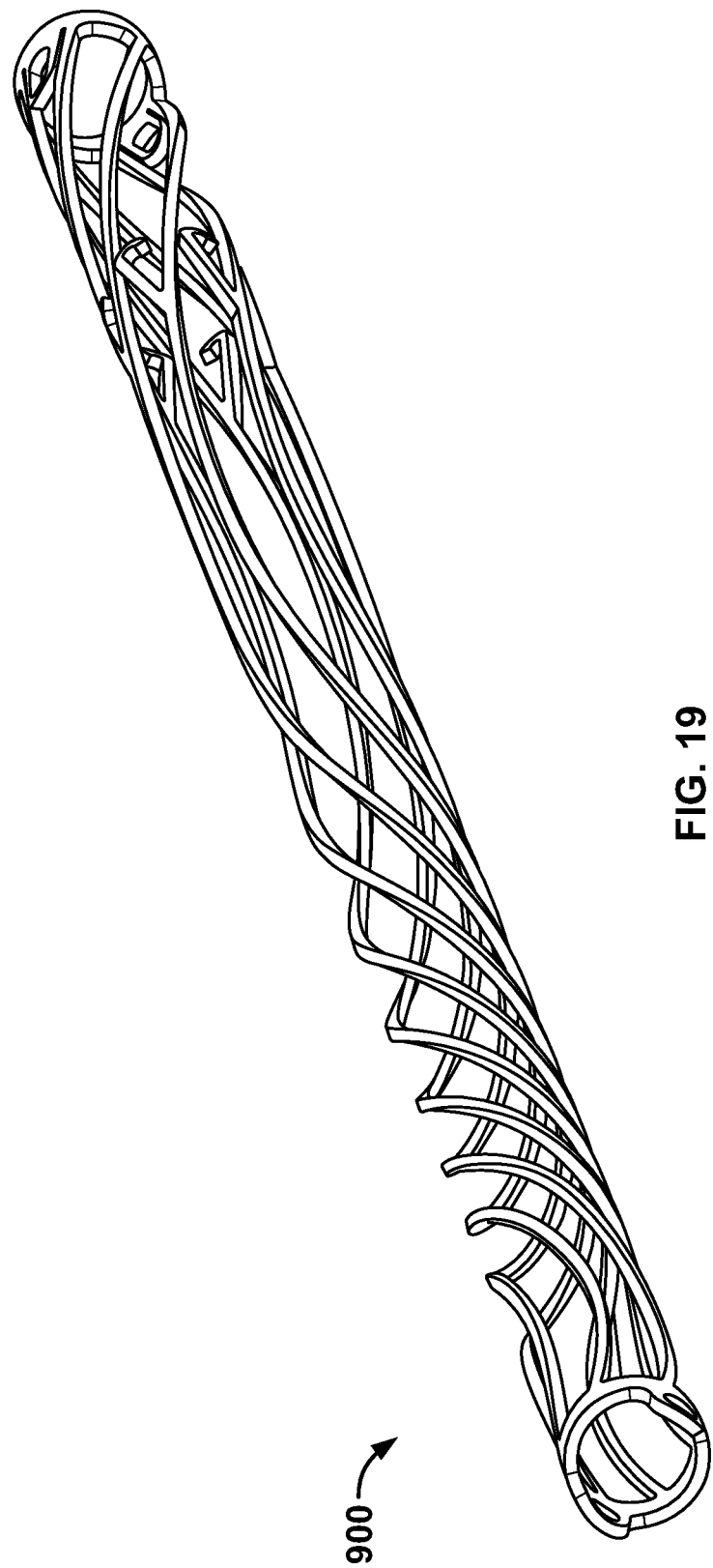
FIG. 19 is a view of an example device frame in an elongated, pre-heat-set configuration, after it was laser-cut from a NiTi tube.

FIG. 19 is a view of an example device frame 900 in an elongated, pre-heat-set configuration, just after it was laser-cut from a NiTi tube, for example. The frame 900 includes cylindrical members near distal ends of the frame, which may correspond to the hub members discussed herein. The frame also includes elongate portions of the tube that can be heat set to a particular configuration so that the elongate portions form the features of the frames discussed herein. The elongate portions generally terminate at the cylindrical members. The frame 900 is intended to depict a general example of how a tube of material may be cut so that remaining portions of the tube may form a frame for some occlusive devices provided herein.

FIGS. 20-25 are drawn to highlight particular occlusive device frame features that can be incorporated into the designs of the occlusive devices provided herein. For example, in some of the figures the designs of the anchor frames and/or occlusion frames are highlighted. It should be understood that one or more of the features that are highlighted in these figures can be included in any of the occlusive devices described elsewhere herein, and that such features (and other features described herein) can be mixed and matched to create hybrid designs that are entirely within the scope of this disclosure. In these figures, no covering component or only partial covering component is shown and some portions of the frames are not shown so that the highlighted frame features are more readily visible. It should be understood that the occlusive devices of FIGS. 20-25 can be combined with a covering component in some embodiments. The covering component can share any or all of the features, characteristics, properties, etc. as described above in reference to the covering component 104 and/or any other exemplary covering components described herein.

Figure 20:
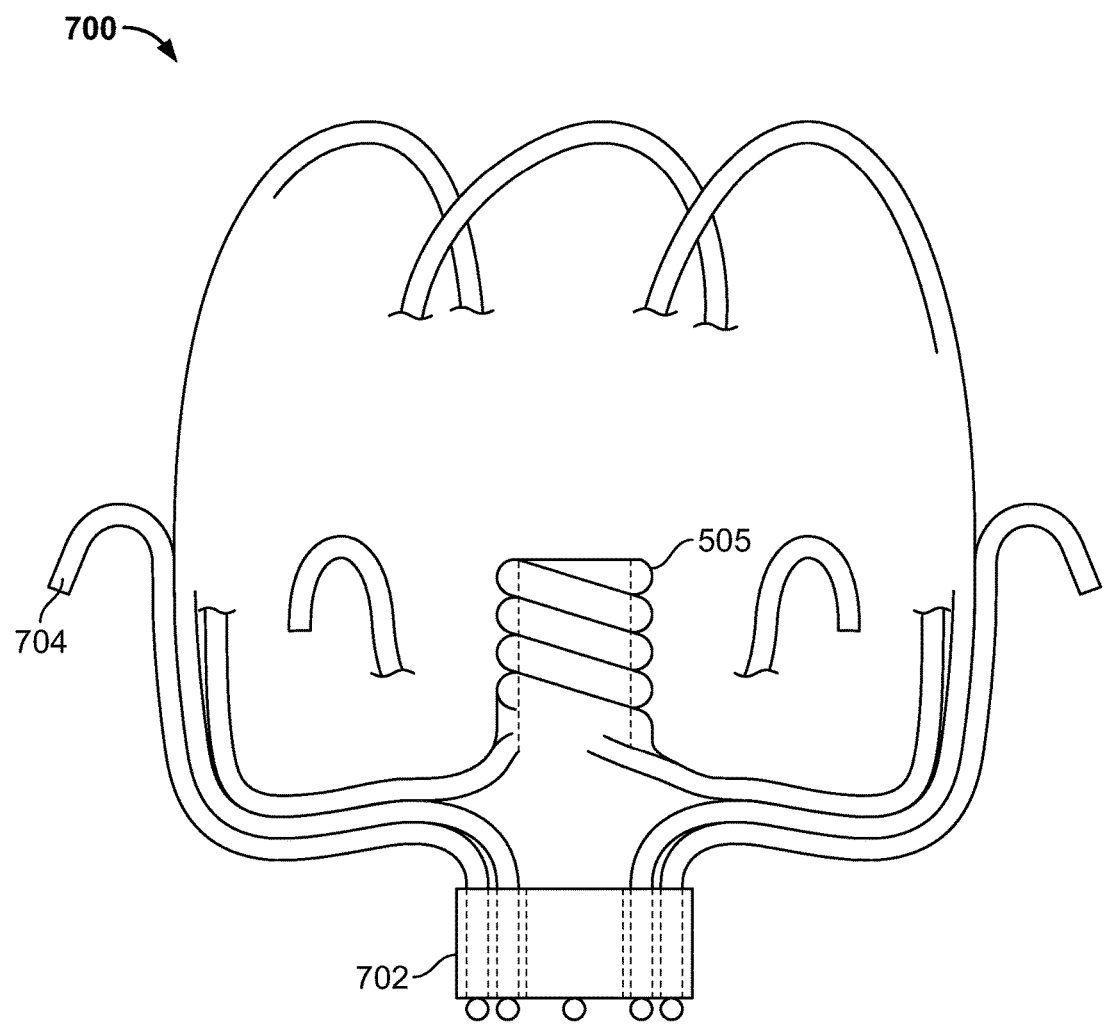
FIGS. 20-25 are conceptual diagrams of portions example device frames.

FIG. 20 is a conceptual diagram of a portion of an example device frame 700 of the type discussed herein. A ring member 702 includes attachment holes that can allow pre-formed anchors 704 to be added separately after the main device frame is already assembled. Ball ends are shown on the frame elongate members and anchor elongate members, and can help secure the elongate members to the ring member 702. Adhesive or weld joints, or other mechanical securing components, can also be optionally used, for example. In the depicted embodiment, the inner hub member comprises an eyelet 505. In some embodiments, the inner hub member may be another type of hub member such as, but not limited to, a ring member, a tube portion, and the like. The pre-formed anchors 704 can use wires of different size, shape, or material than the wires of the occlusion frame, in some implementations. For example, in some embodiments the pre-formed anchors 704 can be formed of a bioabsorbable polymer while the occlusion frame is formed of a metallic material.

Figure 21:
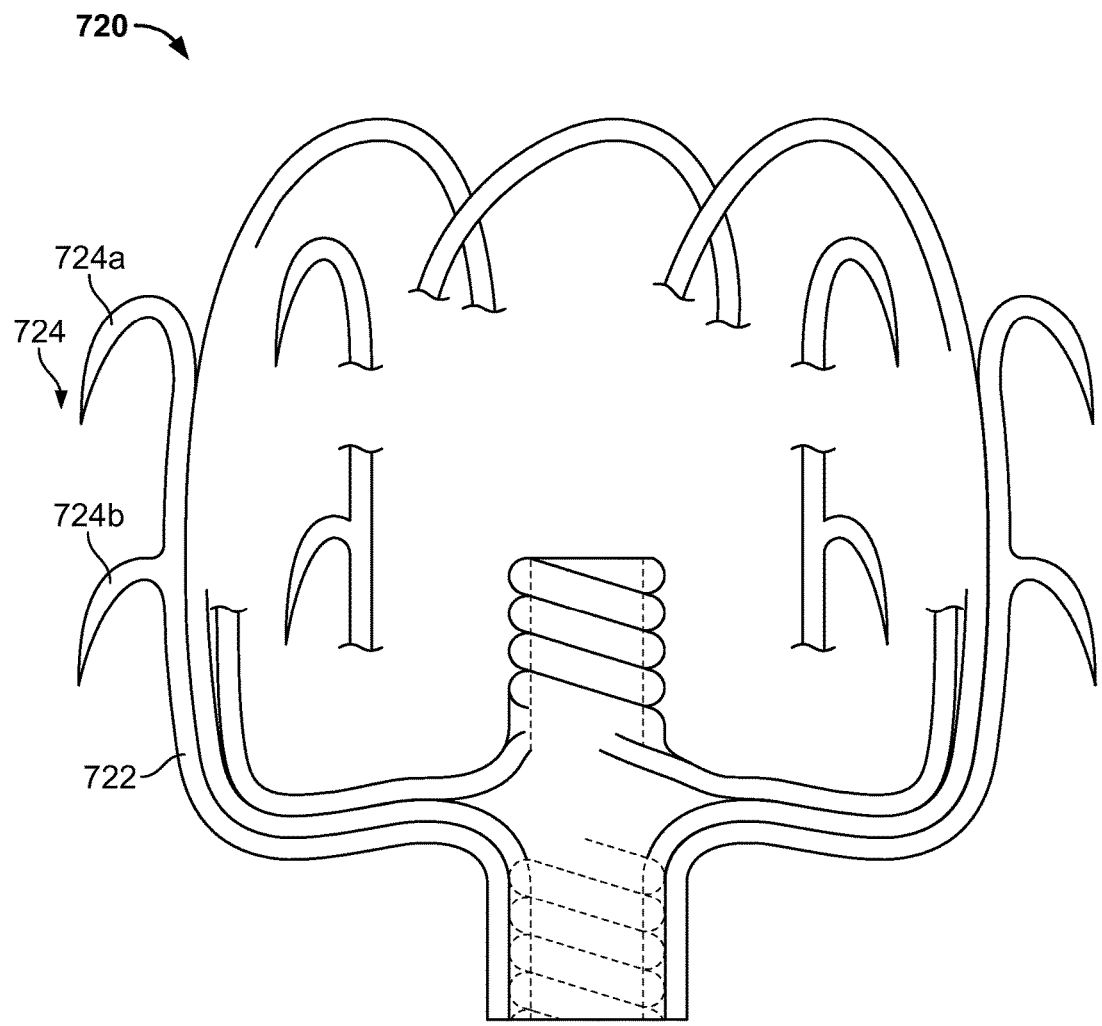

FIG. 21 is a conceptual diagram of a portion of an example device frame 720 of the type discussed herein. The frame 720 includes an anchor assembly 722 with anchors 724, where the anchor assembly 722 is cut from a tube of material. For example, the anchor assembly 722 can be cut from a tube of Nitinol. One or more anchor arms of the assembly 722 include anchors 724 disposed at different longitudinal positions of the device frame 720 (see e.g., anchors 724a, 724b). This can facilitate staged anchoring during deployment, for example. Because anchors 724a and 724b are on the same arm of the assembly, additional anchors may be provided without adding to the profile of the device, for example.

In some embodiments, the anchors 724 (and other anchors provided herein) are designed to be flexible and resilient such that the anchors 724 can be folded to a low-profile delivery configuration for containment within a delivery sheath, and can be translated within the delivery sheath without significant dragging resistance. When deployed from the delivery sheath, the anchors 724 revert to a curved configuration (e.g., as shown, or similar to as shown) that engages with the surrounding tissue at the deployment site. In some implementations, the anchors 724 pierce the surrounding tissue while the other parts of the frame 720 act as a pledget to limit the penetration depth of the anchors 724. In that manner, the risk of pericardial effusion related to penetration of the anchors 724 can be mitigated. In some implementations, the anchors 724 engage the surrounding tissue without penetration. It should be understood that while the anchors 724 are depicted as having sharp points, in some embodiments the anchors 724 (and the other anchors described herein) can have other types of ends including, but not limited to, ball ends, barbs, atraumatic ends, hooks, bifurcated ends, and so on. In some embodiments, individual anchors of the anchors 724 can have differing types of ends.

Figure 22:
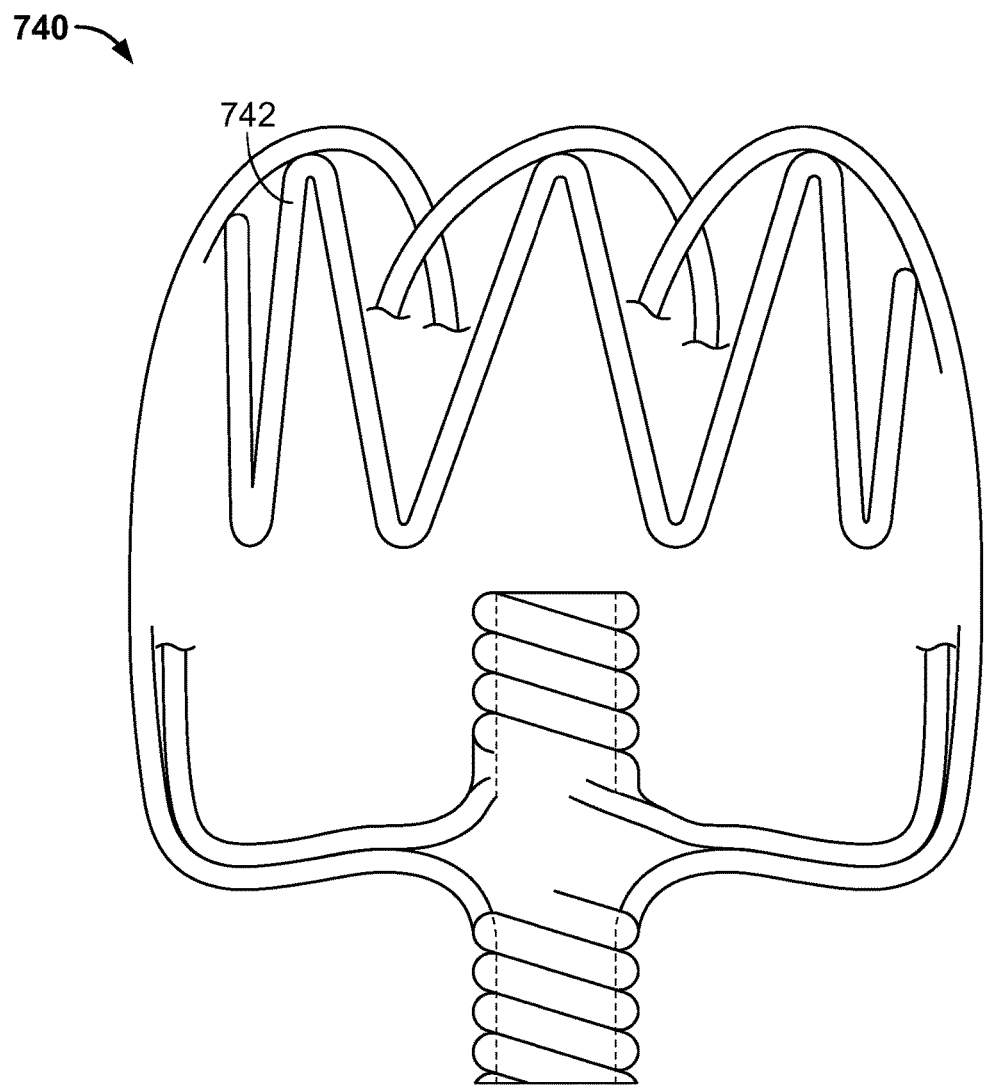

FIG. 22 is a conceptual diagram of a portion of an example device frame 740 of the type discussed herein. The frame 740 includes a distal expanding stent section 742, which can increase radial stiffness near the distal end of the frame 740. The increased radial stiffness may improve anchoring in some embodiments (anchors not shown in FIG. 23, but stent section 742 could be combined with any of the frames shown herein). Stent section 742 can be loosely attached to a distal portion of the frame 740 with suture or film near the looped regions of the frame. The stent section 742 can be formed from wires or cut tubing, for example.

Figure 23:
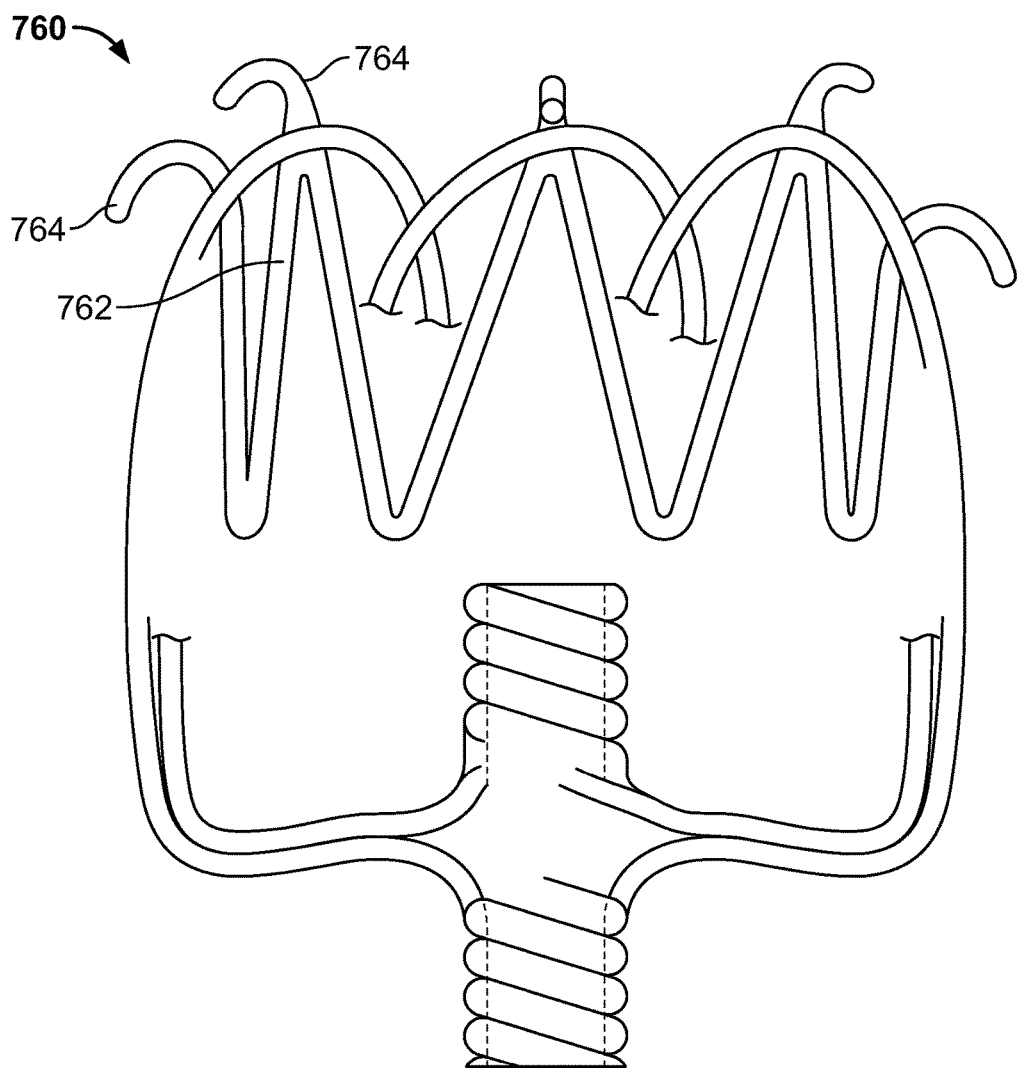

FIG. 23 is a conceptual diagram of a portion of an example device frame 760 of the type discussed herein. Frame 760 is similar to frame 740 of FIG. 23, but includes a stent section 762 with anchor features 764 that extend from the stent section 762.

Figure 24:
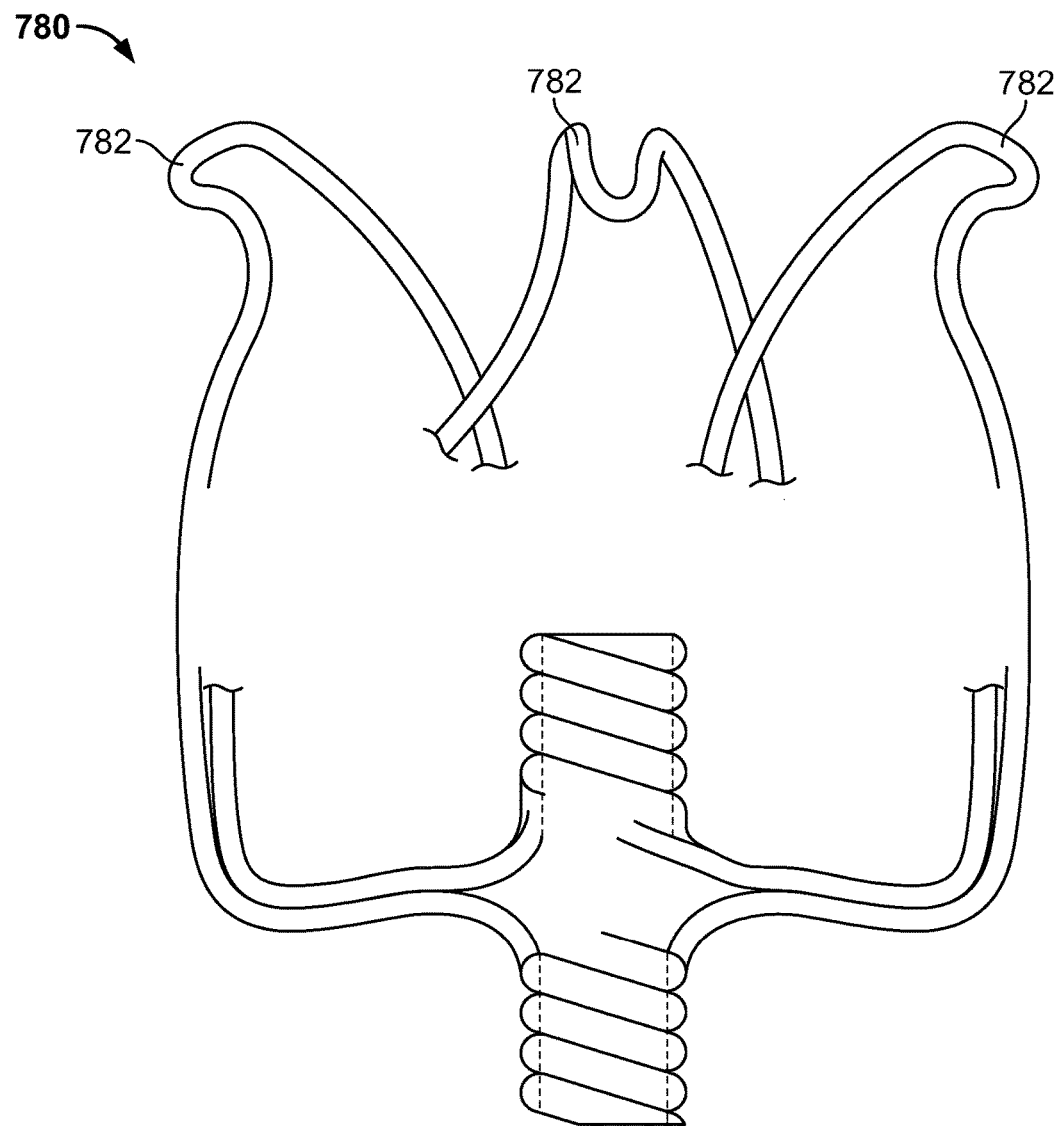

FIG. 24 is a conceptual diagram of a portion of an example device frame 780 of the type discussed herein. Frame 780 includes in-frame anchors 782 at a distal end of the device frame 780. The anchors 782 include a loop and provide passive anchoring designed to avoid or minimize penetration of tissue. In other examples, the anchors 782 could include a sharp feature (e.g., at least one hook, barb, or tine) designed to penetrate tissue. As an alternative, any of the micro-coil anchor features of the described in the provisional application titled "Space Filling Devices," having inventors Coby C. Larsen, Brandon A. Lurie, Steven J. Masters, Thomas R. McDaniel, and Stanislaw L. Zukowski, filed on 15 Mar. 2013, and which is herein incorporated by reference in its entirety for all purposes, can be attached to any appropriate portion of elongate frame members on any of the frames discussed herein.

Figure 25:
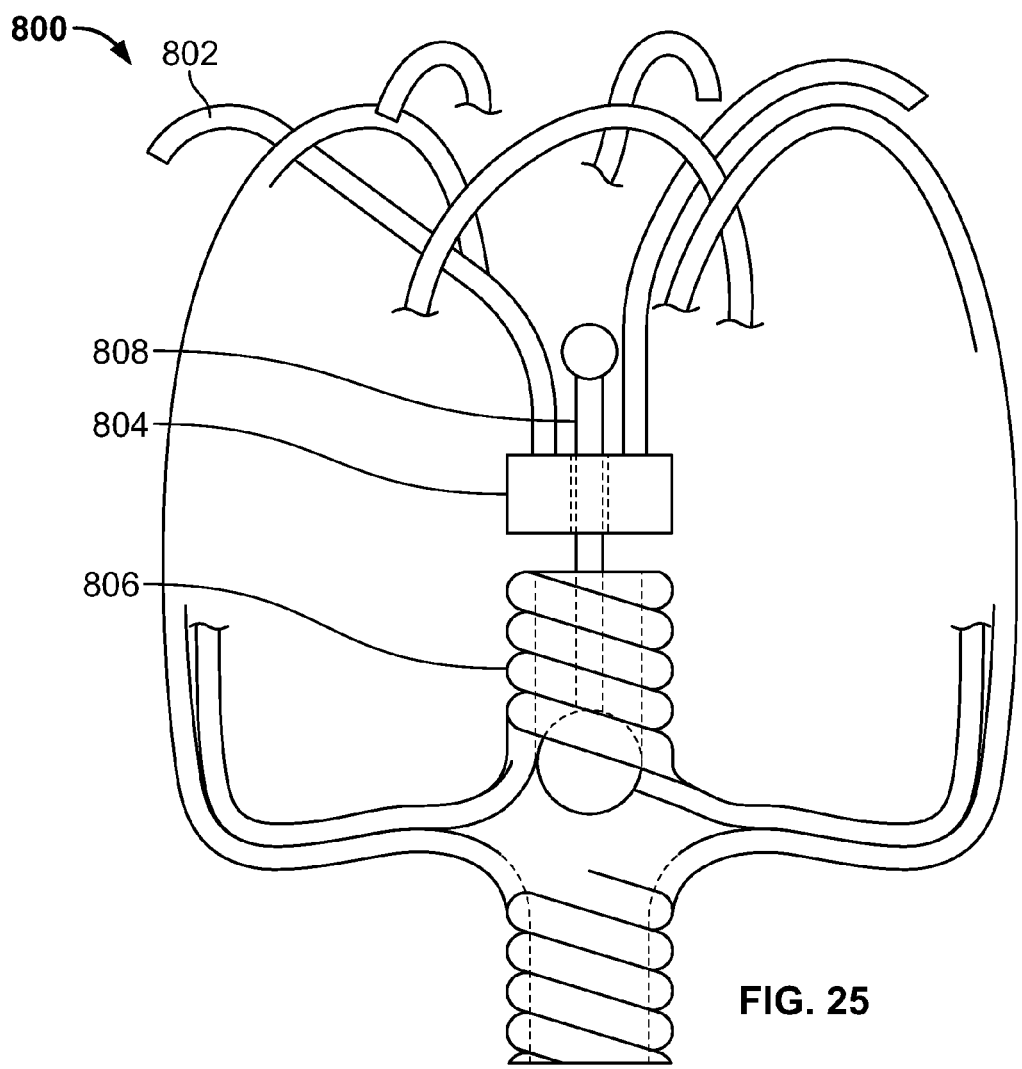

FIG. 25 is a conceptual diagram of a portion of an example device frame 800 of the type discussed herein. Frame 800 includes anchors 802 that extend distally from an anchor hub component 804, where the anchor hub component 804 is coupled to second hub member 806 by a coupling component 808 in this example. Coupling component 808 includes ball ends at respective ends of the component 808. In this embodiment, the anchors 802 can articulate with some degree of independence from the rest of the device frame 800 by virtue of the use of the coupling component 808.

Figure 26A:
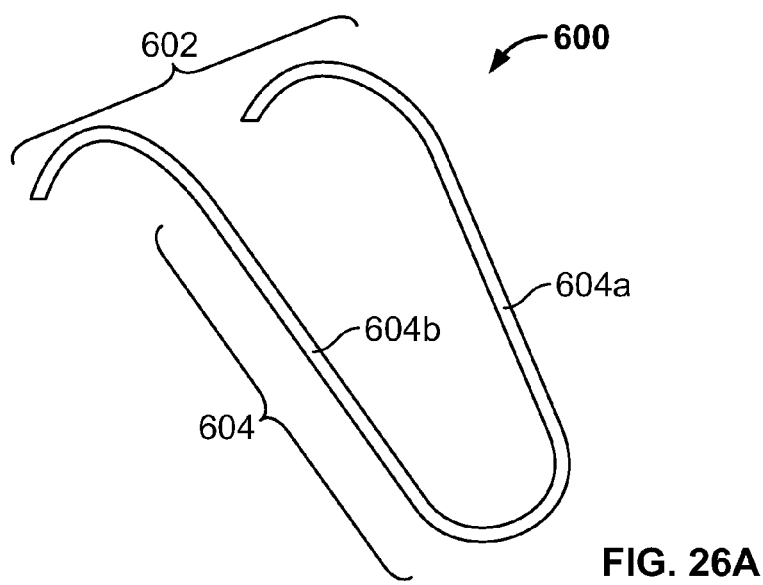
FIG. 26A is a perspective view of an example anchor component that is included on embodiments of the occlusive devices provided herein.

FIG. 26A depicts an example anchor component 600 that is included on some embodiments of the occlusive devices provided herein. The example anchor component 600 is a wire (e.g., NiTi or stainless steel) that is bent to or formed in the approximate shape shown, including the compound bend angles of the ends 602, and the U-shaped arms 604. The free ends of the anchor component 600 can include sharp tips, atraumatic tips, barbs, ball-ends, or other types of tips, or combinations thereof.

Figure 26B:
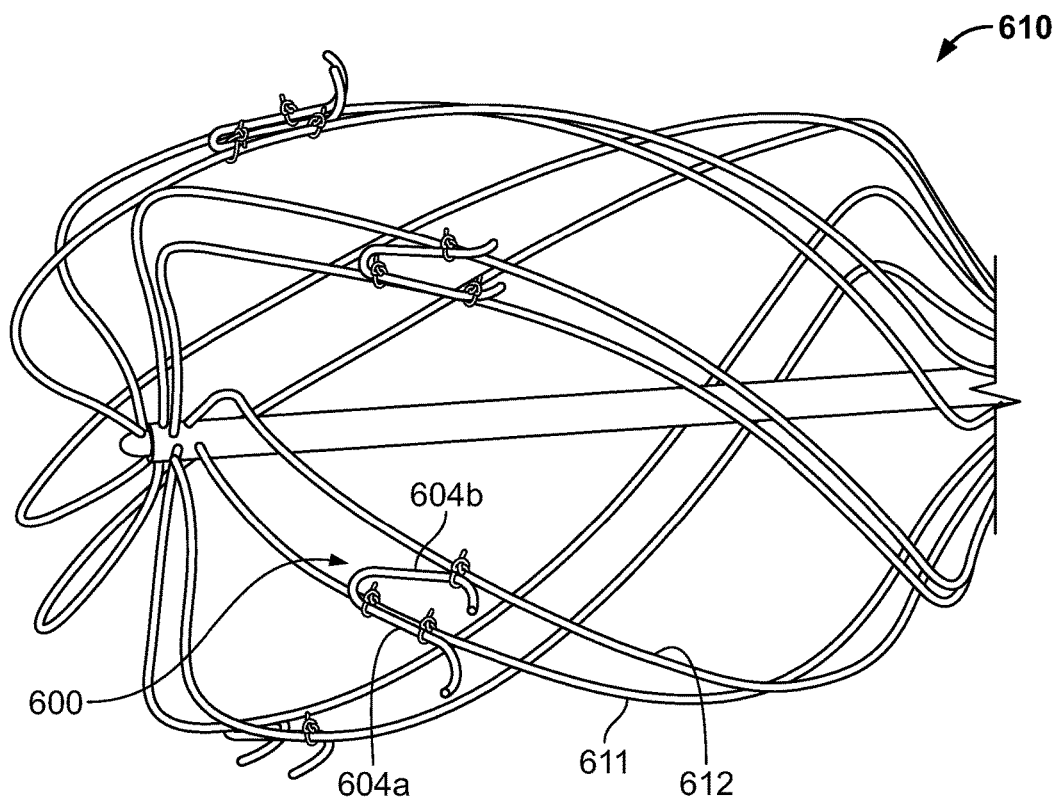
FIG. 26B is a perspective view showing the anchor component of FIG. 26A attached to the elongate members of an example occlusive device.
Figure 26C:
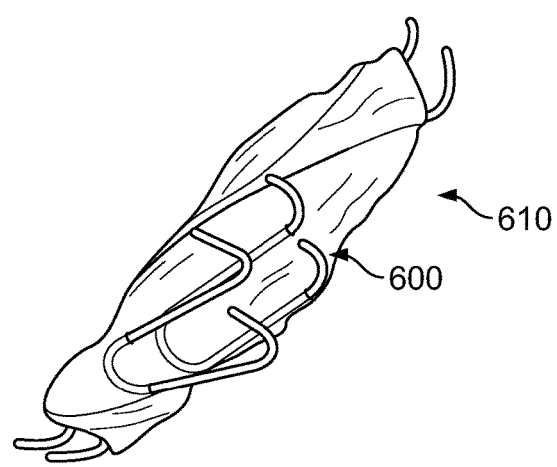
FIG. 26C is a perspective view showing the anchor component of FIG. 26A mounted to an example occlusive device that includes a covering component.

The first and second arms 604a and 604b can be connected to an elongate member of an occlusive device frame. For example, as illustrated in the example of FIG. 26B, the anchor component 600 can be connected to the elongate members 611 and 612 of an occlusive device 610. In this example implementation, the first arm 604a of the anchor component 600 is connected to a first elongate member 611 and the second arm 604b is connected to a second elongate member 612. As shown, the first arm 604a is connected to the first elongate member 611 at two or more positions along the length of the first arm 604a. This method of connecting the first arm 604a causes the first arm 604a to be held in contact with the first elongate member 611 substantially along the full length of the first arm 604a. In some embodiments the second arm 604b is connected to the second elongate member 612 at a single location. Therefore, in some embodiments the second arm 604b can pivot in relation to the second elongate member 612. Such a pivotable connection between the second arm 604b and the second elongate member 612 can allow the anchor component 600 to reconfigure its position in relation to the frame of the occlusive device 610 as the occlusive device 610 expands or contracts into different sizes or configurations. As the anchor component 600 reconfigures its position in relation to the frame of the occlusive device 610, the ends 602 point in a generally radially outward direction so as to maintain an ability to anchor the device to surrounding tissue. In addition, the ends 602 point in a slightly proximal direction to reduce the likelihood of device 610 migration. This feature is illustrated in FIG. 26C, which shows anchor component 600 with ends exposed and in an orientation to provide anchoring while the occlusive device 610 is in a partially collapsed configuration.

FIGS. 27A through 27D illustrate techniques for nesting hub members such that two or more hub members are located concentrically or coaxially in relation to each other. In some embodiments, the elongate frame members of the occlusive devices provided herein terminate at hub members. In some embodiments, a hub member is an eyelet (a coil comprised of one or more elongate members that are wound to have a spiral configuration). In some embodiments, a hub member is a ring member (e.g., refer to FIG. 10) where the elongate frame members terminate. In some embodiments, a hub member is a crimp joint, a collar surrounding an aggregation of elongate members. In some embodiments, the crimp joint may include adhesives, welds, compression fits, and the like, to restrain the elongate members within the collar. The eyelets and ring members may also include adhesives, welds, compression fits, and the like, to provide supplemental restraint of the elongate members. The nested hub configuration can provide an occlusive device that has advantages such as being collapsible to a low profile, as well as being resistant to fatigue. FIGS. 27A-27D are drawn to highlight particular occlusive device frame features that can be incorporated into the designs of the occlusive devices provided herein. It should be understood that one or more of the features that are highlighted in these figures can be included in any of the occlusive devices described elsewhere herein, and that such features (and other features described herein) can be mixed and matched to create hybrid designs that are entirely within the scope of this disclosure. In these figures, no covering component or only partial covering component is shown and some portions of the frames are not shown so that the highlighted frame features are more readily visible. It should be understood that the occlusive devices of FIGS. 27A-27D can be combined with a covering component in some embodiments. The covering component can share any or all of the features, characteristics, properties, etc. as described above in reference to the covering component 104 and/or any other exemplary covering components described herein.

Figure 27A:
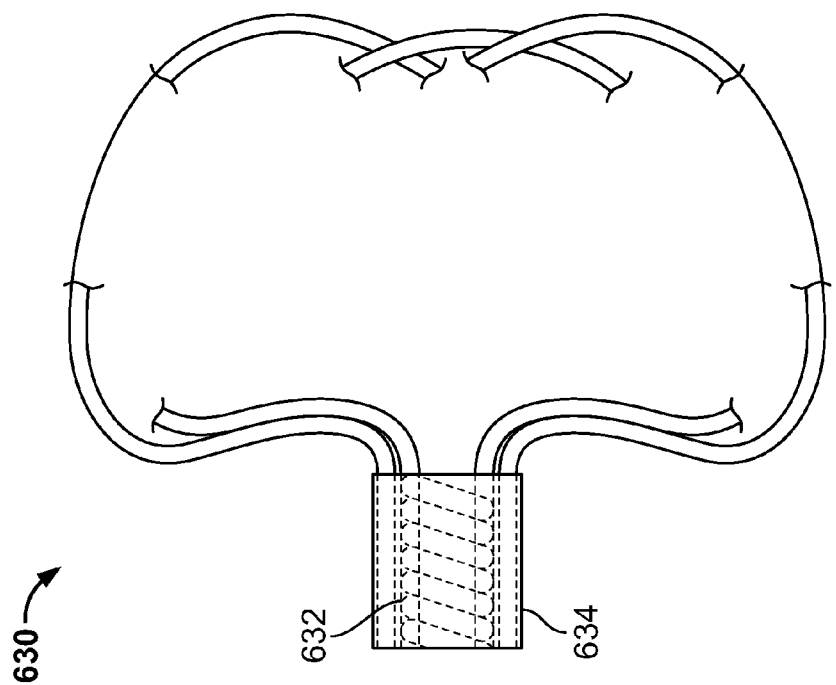
FIGS. 27A-27D are diagrams that exemplify nesting of hub members or eyelets within each other in accordance with embodiments provided herein.
Figure 27B:
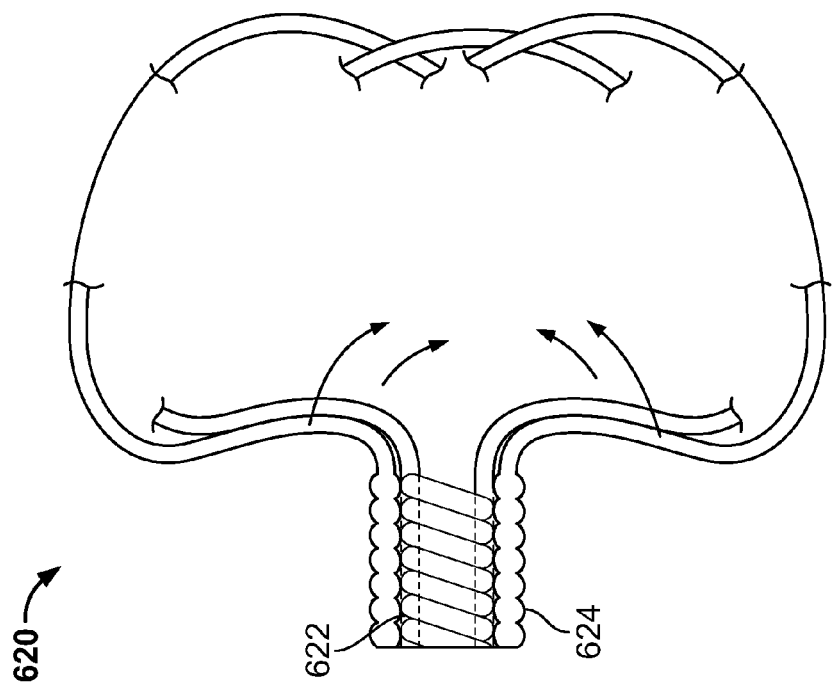
Figure 27C:
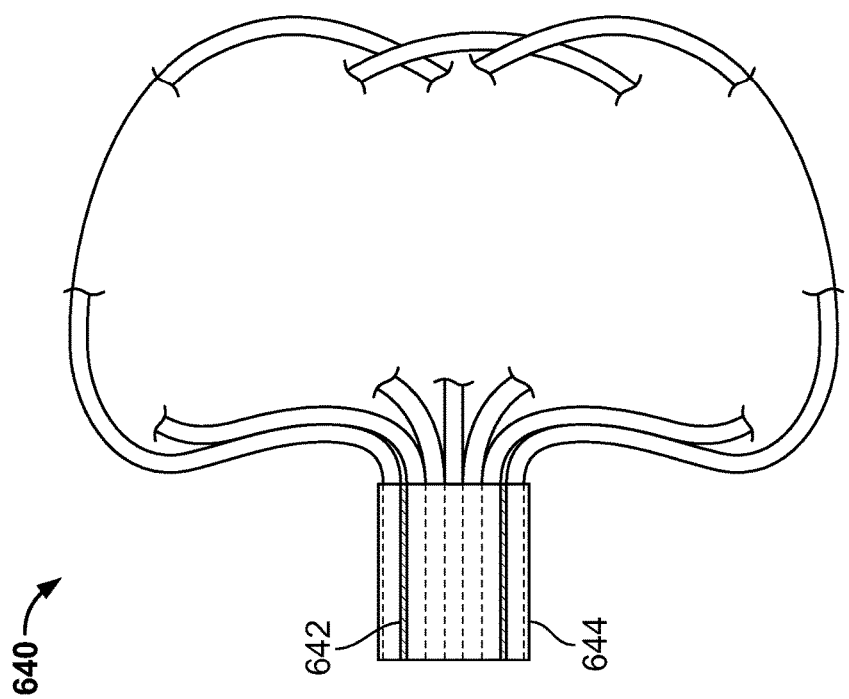
Figure 27D:
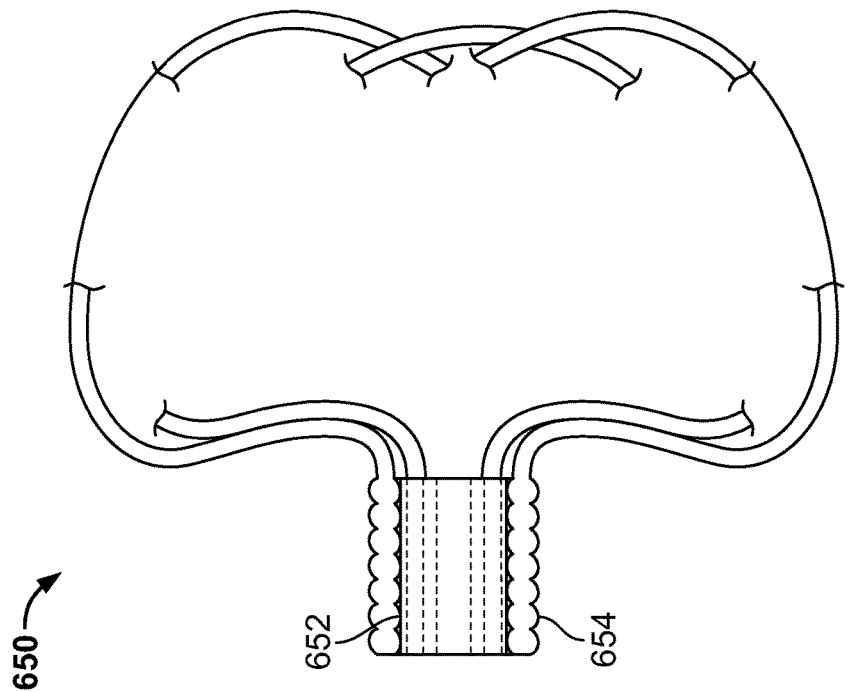

FIG. 27A depicts an occlusive device 620 that has nested eyelets 622 and 624. That is, first eyelet 622 is located within the space defined by the second eyelet 624. FIG. 27B illustrates an occlusive device 630 that has an eyelet 632 nested within a ring member 634. FIG. 27C illustrates an occlusive device 640 that has a crimp joint 642 nested within a ring member 644. FIG. 27D illustrates an occlusive device 650 that has a ring member 652 nested within an eyelet 654. It should be understood that any combination of ring members, eyelets, and crimp joints are envisioned within the scope of this disclosure. In some embodiments that have eyelets, some or all of the elongate elements that make up the eyelets may be conjoined in the eyelet area by welding (e.g., laser welding), or by another technique (e.g., using an adhesive, etc.). In some embodiments that have nested eyelets, such techniques can be used to conjoin some or all of the elongate elements of the inner eyelet and/or the outer eyelet individually, while not conjoining the inner eyelet and outer eyelet together. In some embodiments that have nested eyelets, such techniques can be used to conjoin some or all of the elongate elements of the inner eyelet and outer eyelet together. Any of the occlusive devices provided herein that include one or more eyelets can have some or all of the elongate elements of the eyelet(s) conjoined in such a manner.

Figure 28A:
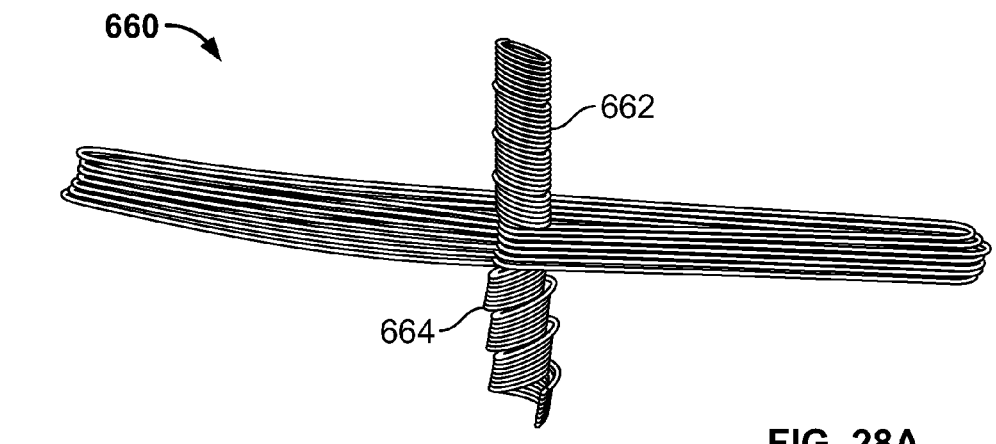
FIGS. 28A-28C depict techniques for configuring an occlusive device with nested eyelets in accordance with some embodiments provided herein.
Figure 28B:
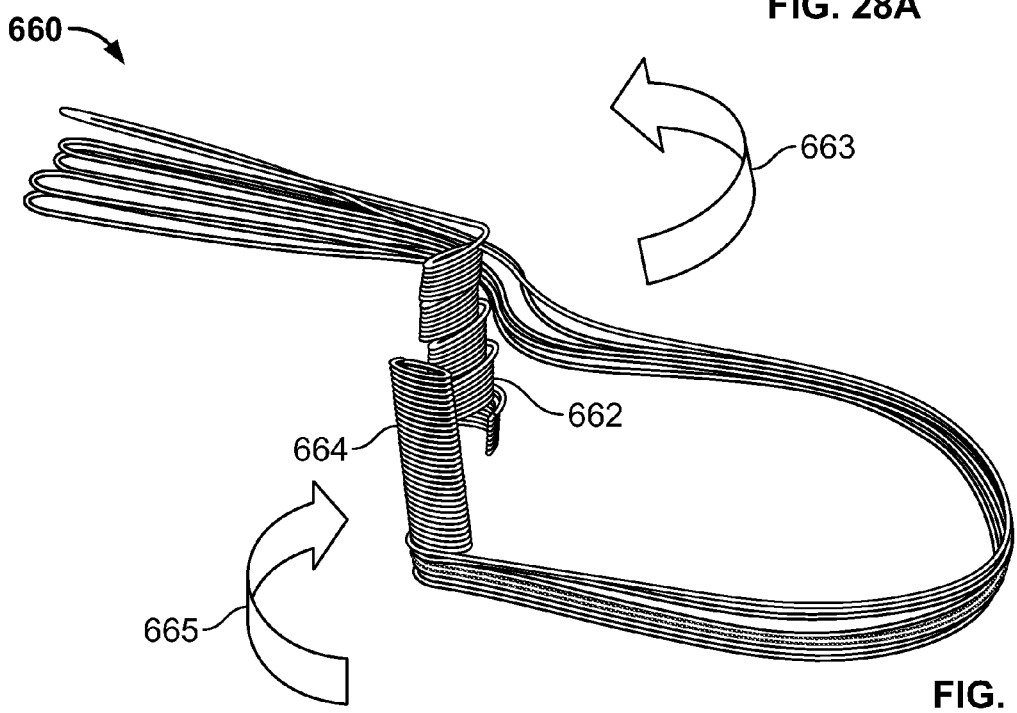
Figure 28C:
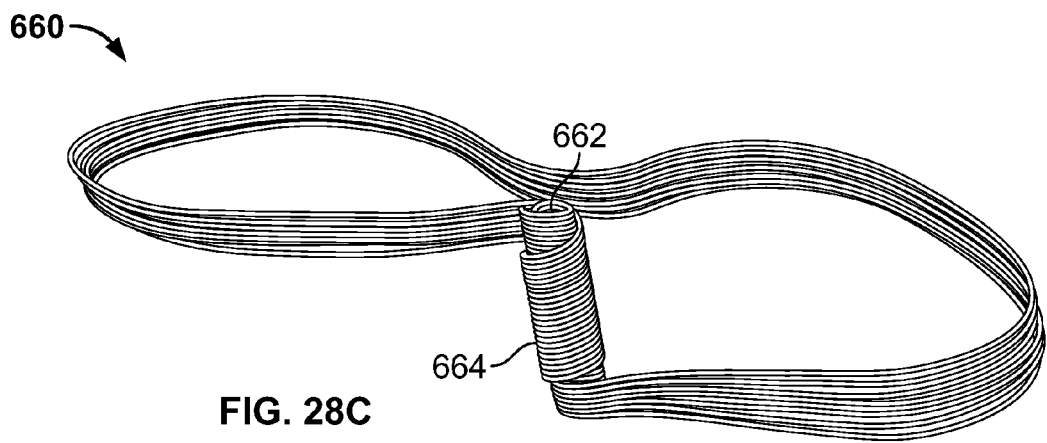

FIGS. 28A through 28C depict a technique for forming a frame of an occlusive device with nested eyelets. FIG. 28A shows an assembly of elongate members 660 that includes a first eyelet 662 and a second eyelet 664. The assembly of elongate members 660 can be the result of a process of winding elongate members using a jig and/or mandrel as described elsewhere herein. The assembly of elongate members 660 includes a first eyelet 662 and a second eyelet 664. While in some embodiments eyelets are included, in other embodiments other types of hubs can be included instead of, or in addition to, eyelets.

FIG. 28B depicts an intermediate step of the technique for nesting hubs. To transition from the configuration of the assembly of elongate members 660 shown in FIG. 28A to the configuration of the assembly of elongate members 660 shown in FIG. 28B, the first and second eyelets 662 and 664 are rotated about 180 degrees individually, and in opposite directions as indicated by arrows 663 and 665. In doing so, the elongate members 660 do not become twisted with each other.

FIG. 28C depicts the final step of the technique for nesting hub members. That is, the inner eyelet 662 is placed substantially within the interior space defined by the second hub 664. In some embodiments, the second hub 664 can be placed substantially within the interior space defined by the first hub 662.

Figure 29A:
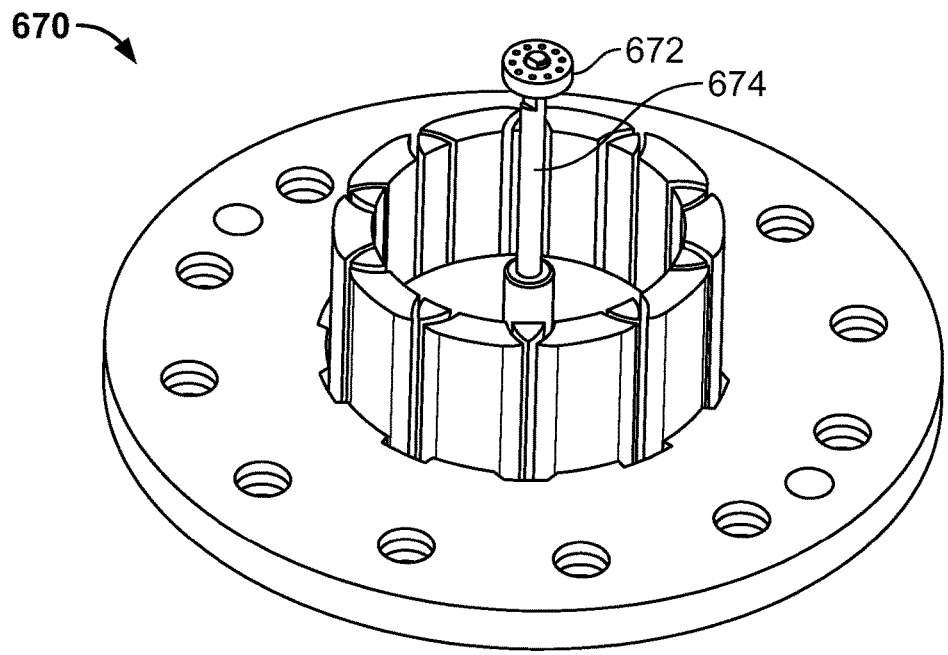
FIGS. 29A and 29B are perspective and side views of a winding jig that can be used to form occlusive devices with nested eyelets.
Figure 29B:
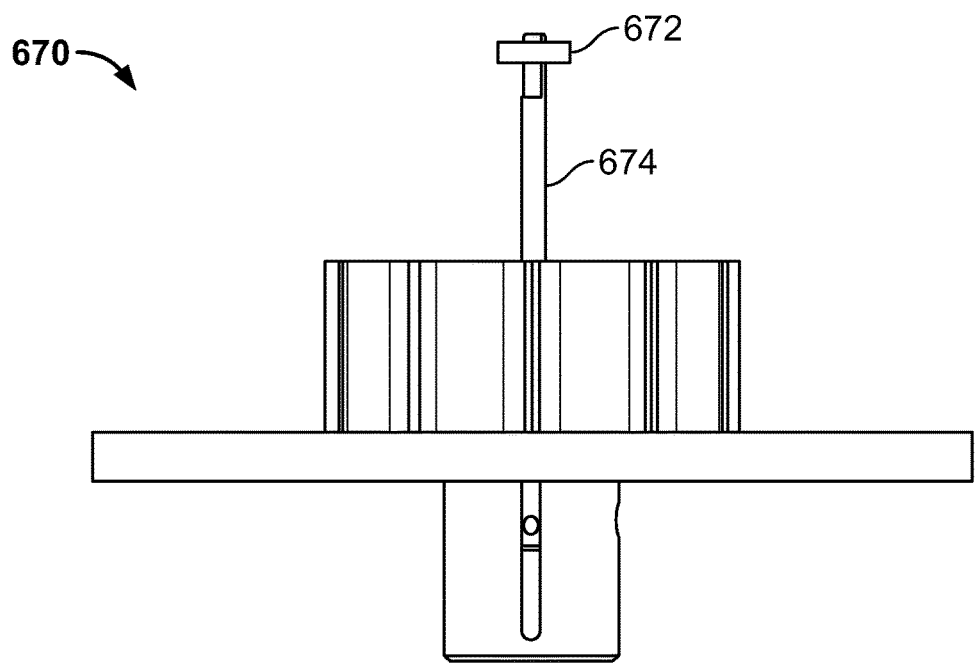

FIGS. 29A and 29B show tooling 670 that can be used to wind elongate members to make occlusive devices with nested eyelets. The winding pattern starts at the winding start disc 672 and winds an eyelet down the post 674. The elongate members are then wound, each following a similar but discretely different path (in this example about 216 degrees). The elongate members are then wound, starting at the bottom of the post, upwards to form another eyelet around the initial eyelet.

FIGS. 30A through 34D provide embodiments of occlusive devices that include distal anchoring members. Various types of distal anchoring members are described. FIGS. 30A-34D are drawn to highlight particular occlusive device frame features that can be incorporated into the designs of the occlusive devices provided herein. It should be understood that one or more of the features that are highlighted in these figures can be included in any of the occlusive devices described elsewhere herein, and that such features (and other features described herein) can be mixed and matched to create hybrid designs that are entirely within the scope of this disclosure. In some of these figures, some portions of the frames and covering components are not shown so that the highlighted frame features are more readily visible.

Figure 30B:
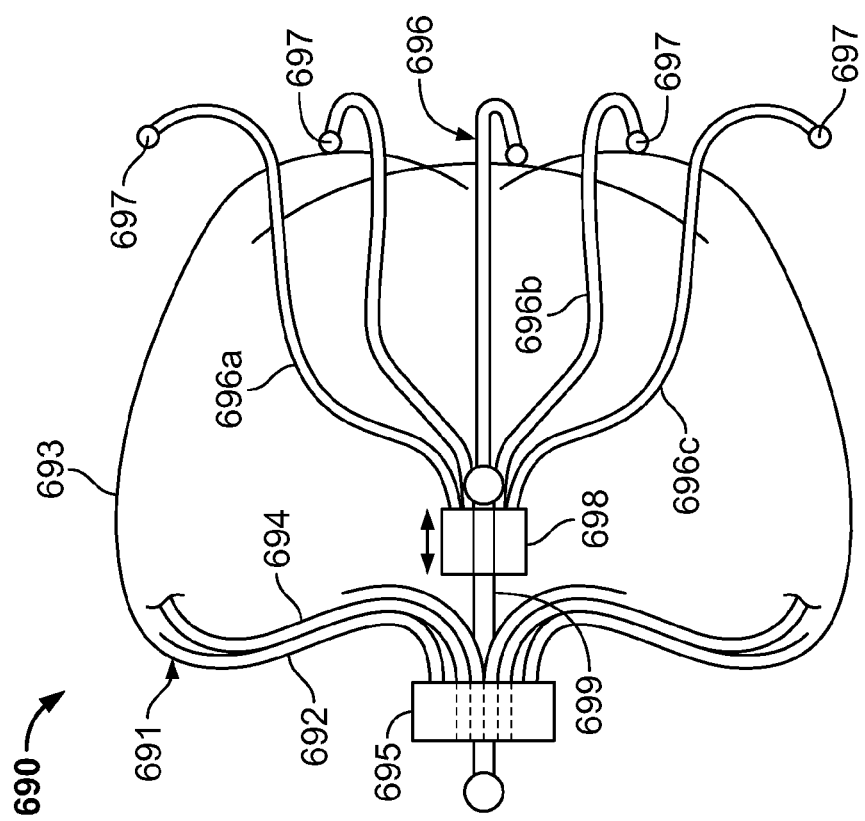
FIGS. 30A and 30B depict example occlusive device embodiments with distal anchoring assemblies.
Figure 30A:
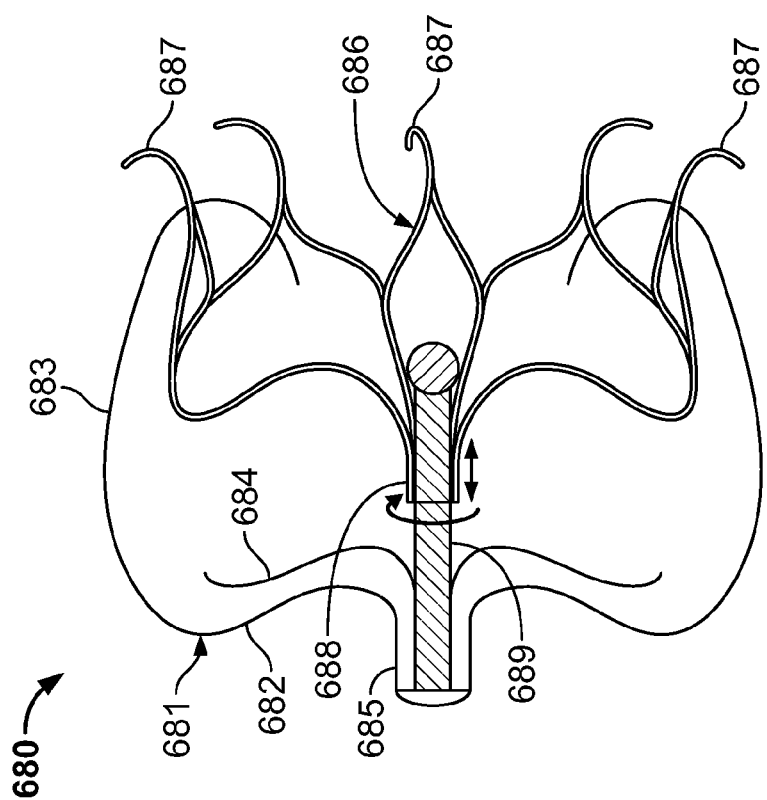

FIG. 30A depicts an occlusive device 680 that includes an occlusive member 681 and a distal anchoring member 686. As with some other occlusive devices described herein, the occlusive member 681 includes an occlusive face 682, a laterally facing skirt 683, an inverted section 684, and a hub member 685 (which may be a nested hub assembly in some embodiments, but in other embodiments the hubs are not nested).

In some embodiments, the distal anchoring member 686 is constructed from material that is cut and then expanded. For example, in some embodiments the distal anchoring member 686 is made from a tube of material that is laser-cut and then expanded (and heat-set in some embodiments) to the configuration substantially as shown. In some embodiments, NiTi is used as the material, but other materials such as stainless steel and polymers may also be used, instead of or in combination with NiTi. The design of the distal anchoring member 686 can facilitate the application of a radial force from the distal anchoring member 686 to the surrounding tissue that can assist with the anchoring performance of the occlusive device 680. In addition, the configuration of the distal anchoring member 686 includes portions made of curved elongate members. Such curved portions can provide axial and radial flexibility and springiness whereby the anchor frame is resistant to device migration within the anatomy of the patient. Further, in some embodiments the distal anchoring member 686 includes multiple free ends 687 that can abut or penetrate tissue to provide anchorage of the occlusive device 680 in relation to the surrounding tissue.

In some embodiments, the occlusive member 681 and distal anchoring member 686 may be coupled together by a coupling element 689. The coupling element may be an adhesive, such as FEP, or a weld, in some examples. In the depicted example, the coupling element 689 is a mechanical coupling element, such as a joint, rivet (e.g., a barbell rivet), or various types of catch members. The coupling element may substantially align the occlusive member hub 685 and the anchor member hub 688 along a longitudinal axis of the device frame. In some examples, the occlusive member hub 685 and the anchor member hub 688 may be concentrically aligned along the longitudinal axis of the device frame.

In some embodiments, the coupling element 689 may allow relative movement between the occlusive member 681 and distal anchoring member 686. For example, the occlusive member 681 and distal anchoring member 686 may be allowed to move axially in relation to each other, or to rotate in relation to each other.

FIG. 30B shows another embodiment of an occlusive device 690 that includes a distal anchoring member 696. As with some other occlusive devices described herein, the occlusive member 691 includes an occlusive face 692, a laterally facing skirt 693, an inverted section 694, and a hub member 695 (which may be a nested hub assembly in some embodiments, but in other embodiments the hubs are not nested).

In some embodiments, the distal anchoring member 696 is made of multiple elongate members (e.g., 696a, 696b, and 696c) that terminate at one end at a ring hub member 698 and at the other end at ball ends 697. The ball ends 697 are adapted for atraumatically engaging body tissue and securing the device 690 in place, for example by friction, pressure, or entanglement. In some examples, the ball ends 697 may be formed on the end of the fixation anchor wire by laser welding. The ball ends 697 may provide anchoring and may reduce a potential for perforation or pericardial effusion, in some implementations. In general, the ball ends 697 or other passive anchor features discussed herein may cause less friction on an inside surface of a delivery sheath as compared to some active anchor elements with sharp edges, in some implementations, which may reduce particulation with respect to the delivery system in some cases. In some embodiments, a diameter of the ball ends 697 may be about two times the diameter of the frame anchor wire. In some examples, the diameter of the ball end 697 may range from about 1× (with just a round wire end) to about 2× the diameter of the frame anchor wire, for example, the diameter may be about 1.5× the diameter of the frame anchor wire, or about 1.6×, 1.7×, 1.8×, or 1.9× the diameter of the frame anchor wire. The ball ends 697 may be created by applying a laser pulse to the end of the frame anchor wire, for example. For example, in some embodiments, spherical members or ball ends 697 may be formed directly on ends of the frame anchor wires using a precision laser weld technique (e.g., using an Nd:YAG laser).

In some embodiments, the occlusive member 691 and distal anchoring member 696 may be coupled together by a coupling element 699. The coupling element may be an adhesive, such as FEP, or a weld, in some examples. In the depicted example, the coupling element 699 is a mechanical coupling element, such as a joint, rivet (e.g., a barbell rivet), or various types of catch members. In some embodiments, the coupling element 699 may allow relative movement between the occlusive member 691 and distal anchoring member 696. For example, the occlusive member 691 and distal anchoring member 696 may be allowed to move axially in relation to each other, or to rotate in relation to each other.

Figure 31B:
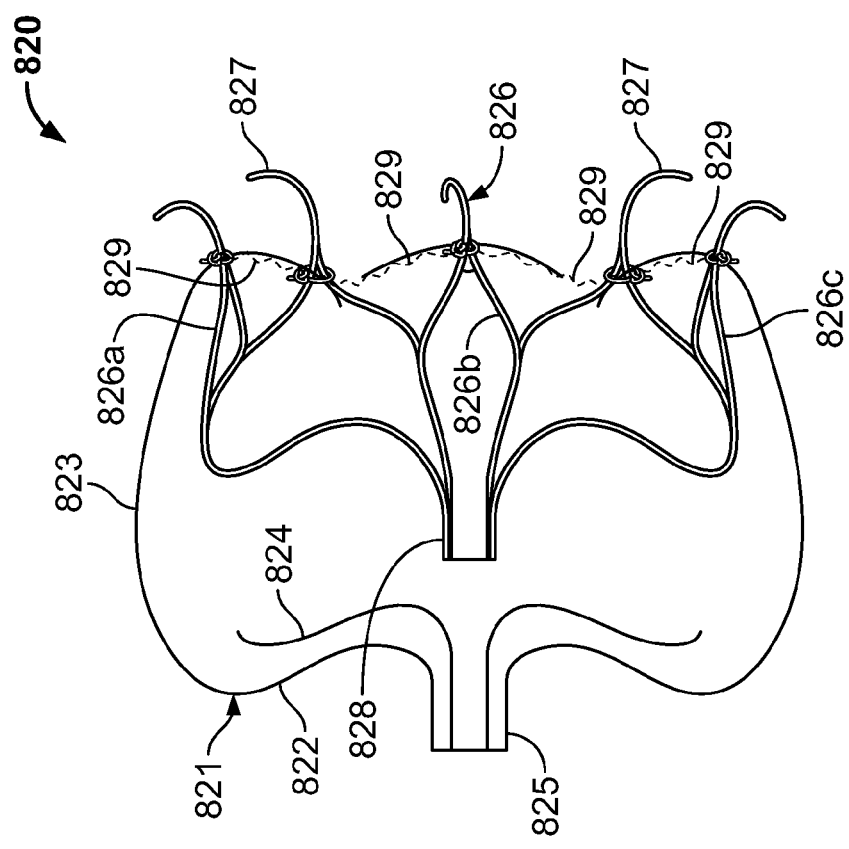
FIGS. 31A and 31B depict example occlusive device embodiments with distal anchoring assemblies.
Figure 31A:
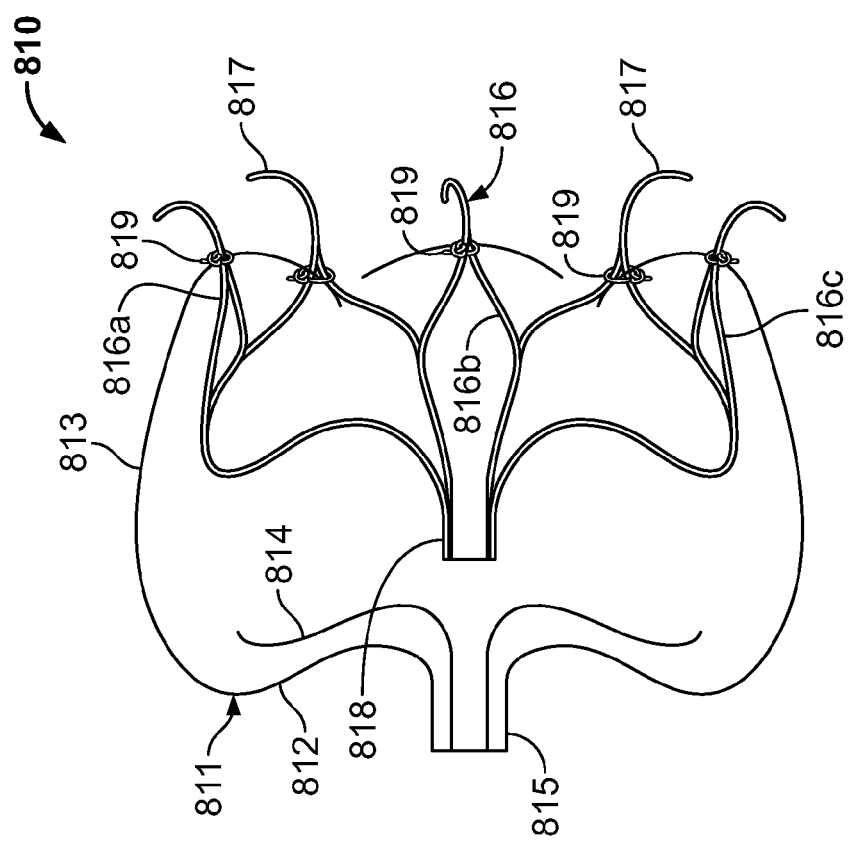

FIG. 31A shows another embodiment of an occlusive device 810 that includes a distal anchoring member 816. As with other occlusive devices described herein, the occlusive member 811 includes an occlusive face 812, a laterally facing skirt 813, an inverted section 814, and a hub member 815 (which may be a nested hub assembly in some embodiments, but in other embodiments the hubs are not nested).

In some embodiments, the distal anchoring member 816 is constructed from material that is cut and then expanded. For example, in some embodiments the distal anchoring member 816 is made from a tube of material that is laser-cut and then expanded (and heat-set in some embodiments) to the configuration substantially as shown. In some embodiments, NiTi is used as the material, but other materials such as stainless steel and polymers may also be used.

In some embodiments, the occlusive member 811 and distal anchoring member 816 may be coupled together by a coupling element 819. In contrast with occlusive device 680 and occlusive device 690 in occlusive device 810 the hubs 815 and 818 are not coupled. Rather, the perimeters of the occlusive member 811 and distal anchoring member 816 may be coupled together by multiple suture knots 819. In some embodiments, the hubs 815 and 818 can also be tethered together using a suture. The suture knots 819 lash and constrain the elongate members (e.g., 816a, 816b, 816c) to the elongate members of the occlusive member 811, or to the covering component of the occlusive member 811, or to both the elongate members and the covering component of the occlusive member 811.

This technique of coupling occlusive member 811 and distal anchoring member 816 using multiple suture knots 819 may allow the occlusive device 810 to collapse to a very low profile for placement within a delivery sheath. In addition, in some embodiments the use of multiple suture knots 819 to couple the peripheries of the occlusive member 811 and distal anchoring member 816 may enhance the stability of the occlusive device 810 during loading into a delivery sheath, during deployment, and after deployment.

FIG. 31B shows another embodiment of an occlusive device 820 that includes a distal anchoring member 826. As with other occlusive devices described herein, the occlusive member 821 includes an occlusive face 822, a laterally facing skirt 823, an inverted section 824, and a hub member 825 (which may be a nested hub assembly in some embodiments, but in other embodiments the hubs are not nested).

In some embodiments, the occlusive member 821 and distal anchoring member 826 may be coupled together by an overhand running stitch 829 that defines a spiral path around some or all of the periphery of the occlusive member 821 and distal anchoring member 826 at the intersection thereof. In contrast with occlusive device 680 and occlusive device 690, in occlusive device 820 the hubs 825 and 828 are not coupled. Rather, the perimeters of the occlusive member 821 and distal anchoring member 826 may be coupled together by an overhand running stitch 829. In some embodiments, the hubs 825 and 828 are tethered together using a suture. The overhand running stitch 829 lashes and constrains the elongate members (e.g., 826a, 826b, 826c) to the elongate members of the occlusive member 821, or to the covering component of the occlusive member 821, or to both the elongate members and the covering component of the occlusive member 821.

This technique of coupling occlusive member 821 and distal anchoring member 826 using an overhand running stitch 829 may allow the occlusive device 820 to collapse to a very low profile for placement within a delivery sheath. In addition, in some embodiments the use of an overhand running stitch 829 to couple the peripheries of the occlusive member 821 and distal anchoring member 826 may enhance the stability of the occlusive device 820 during loading into a delivery sheath, during deployment, and after deployment. Further, attachment of the distal anchoring member 826 to the occlusive member 821 can, in some embodiments, help center the occlusive device 820 within an anatomical space (e.g., a LAA).

Figure 32:
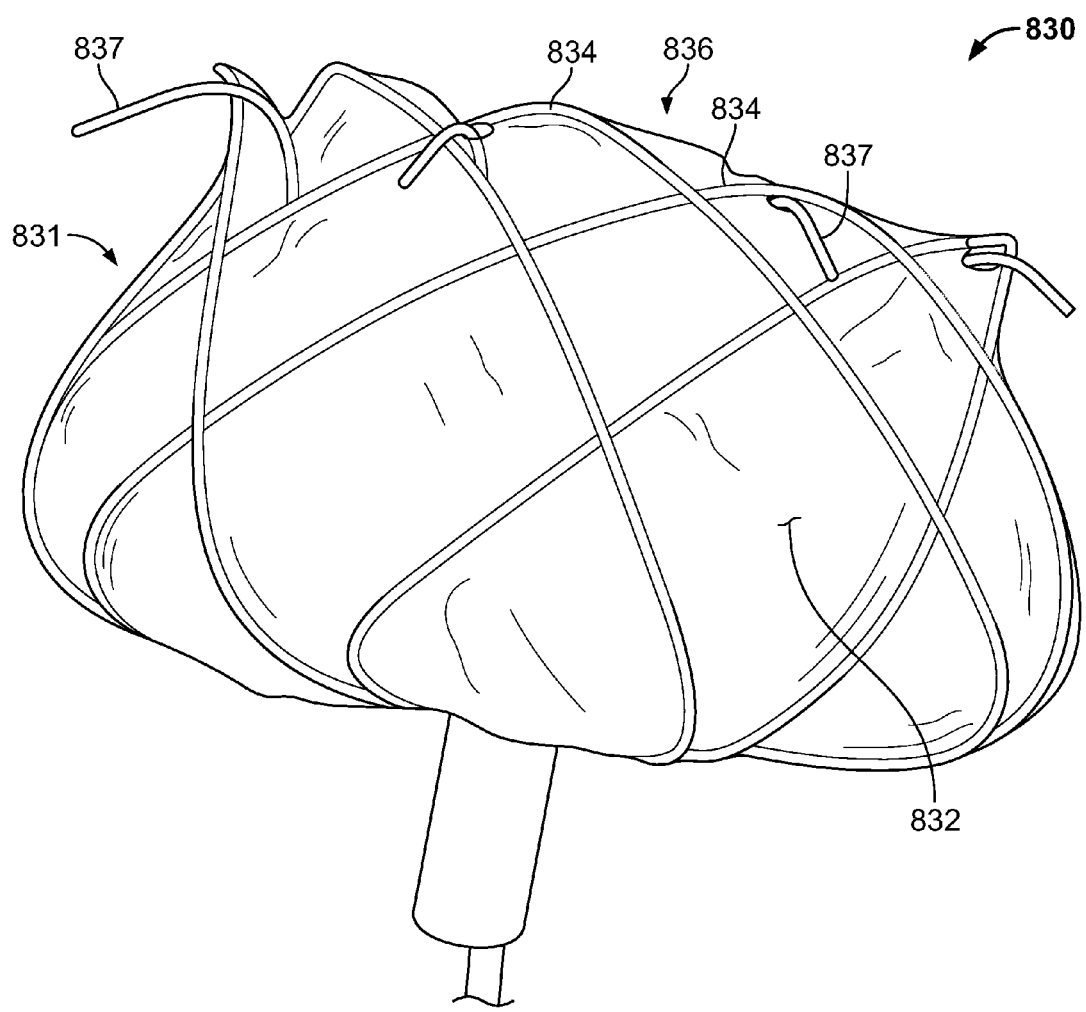
FIG. 32 is a perspective side view of an example occlusive device embodiment.
Figure 33B:
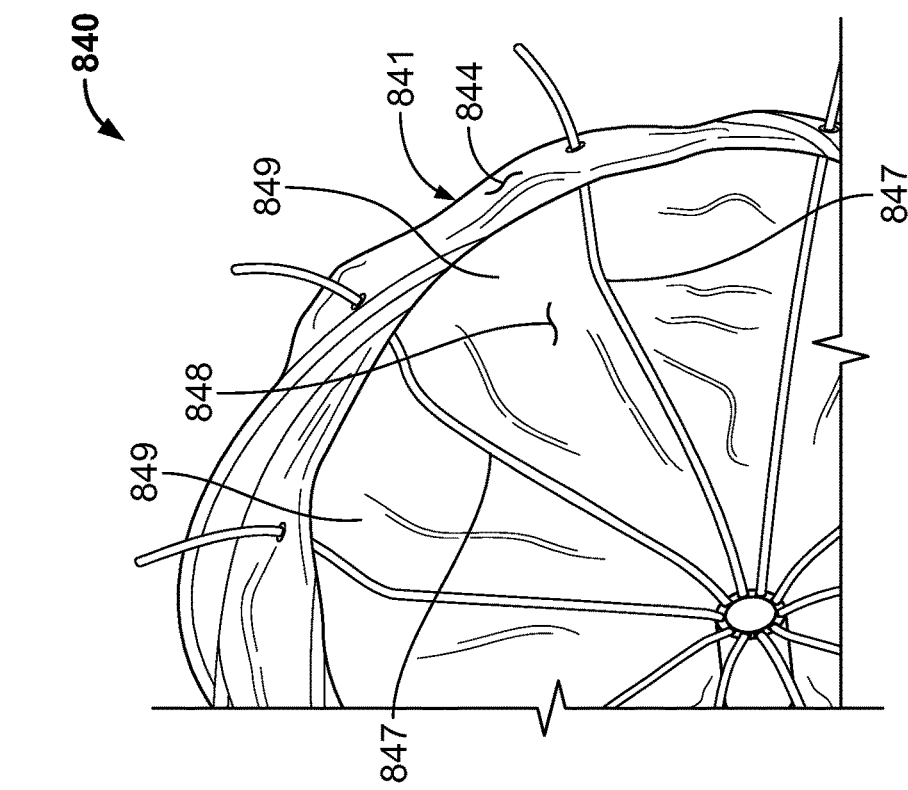
FIGS. 33A-33D show various views of example occlusive device embodiments.
Figure 33A:
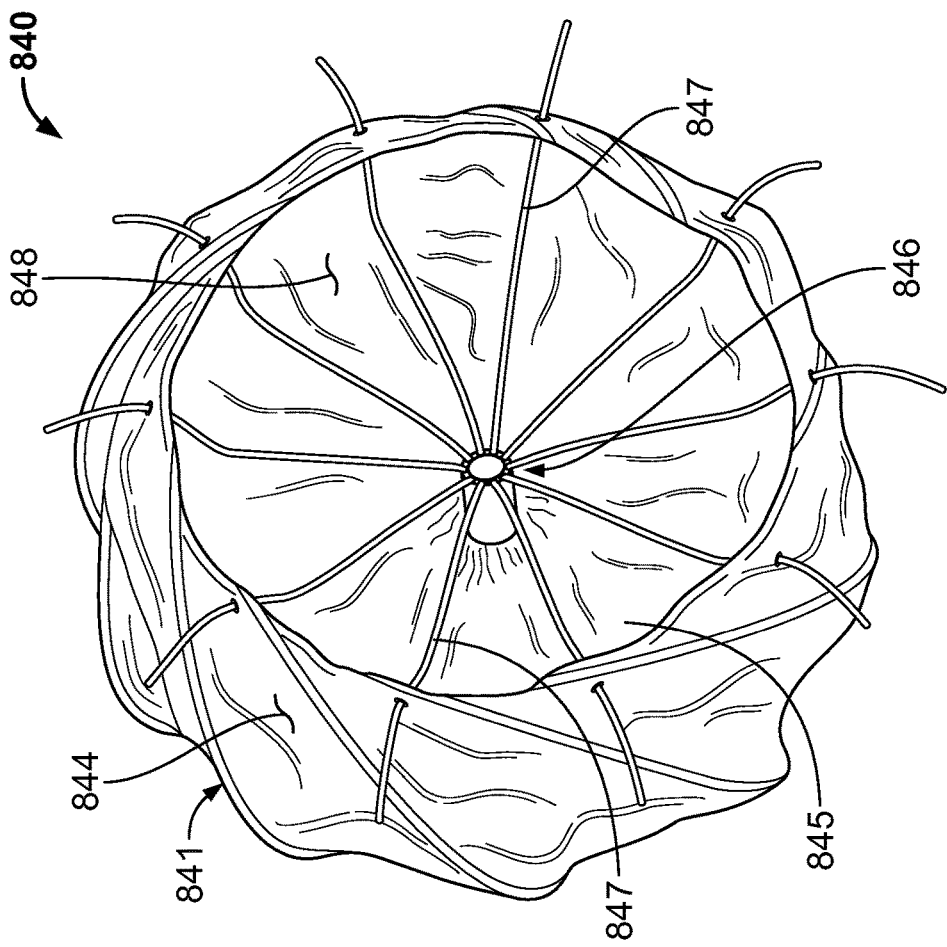
Figure 33D:
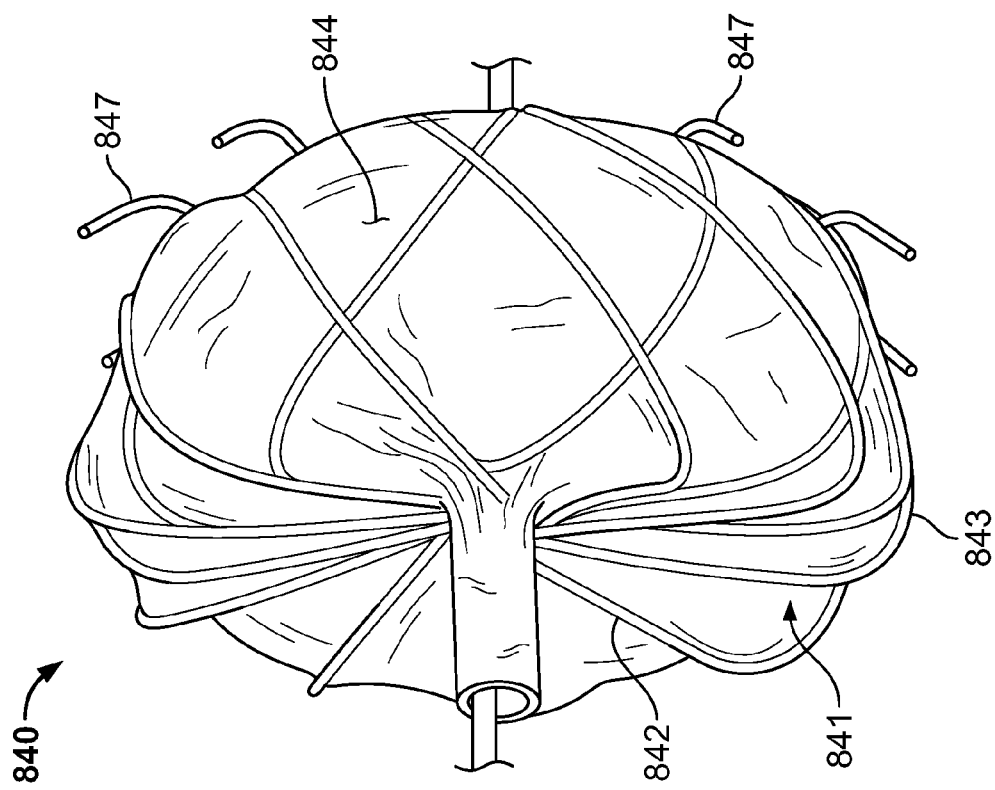
Figure 33C:
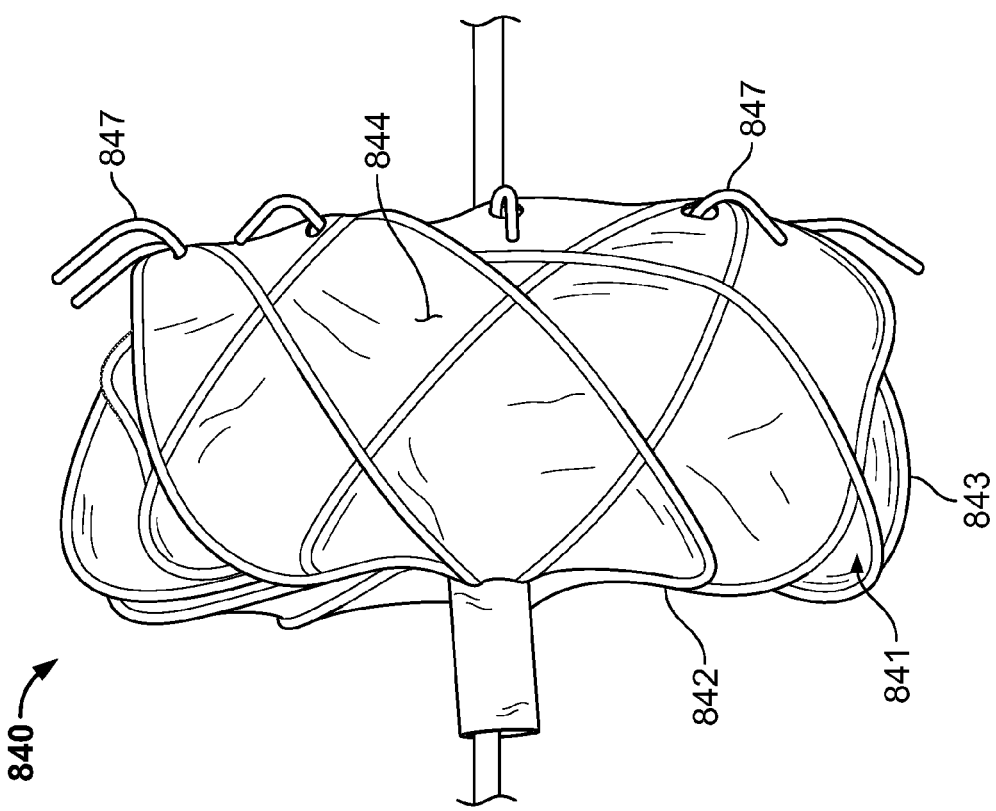

FIG. 32 shows a side perspective view of another occlusive device 830 that includes an occlusive member 831 and a distal anchoring member 836. In this view, only the end portions of the elongate members 837 of the distal anchoring member 836 are visible. It should be understood that the distal anchoring member 836 can be analogous to any of the distal anchoring members 686, 696, 816, and 826 of FIGS. 30A, 30B, 31A, and 31B; can be analogous to the distal anchoring member 846 of FIGS. 33A-33C; and can have any other similar design.

It can be seen that the elongate member 837 of the distal anchoring member 836 projects generally radially from the occlusive member 831. In particular, in some embodiments the elongate members 837 of the distal anchoring member 836 project through the covering component 832 of the occlusive member 831. Further, in some embodiments the elongate members 837 of the distal anchoring member 836 project from the occlusive member 831 through the interstitial spaces defined by the elongate members 834 of the occlusive member 831 (as shown in FIG. 32).

A suturing technique for lashing and constraining the elongate members 837 of the distal anchoring member 836 to the covering component 832 and elongate members 834 of the occlusive member 831 can be used for occlusive device 830. For example, in some embodiments, suture knots (refer to FIG. 31A) can be used to lash and constrain the elongate members 837 of the distal anchoring member 836 to the elongate members 834 of the occlusive member 831. In some embodiments, an overhand running stitch technique (refer to FIG. 31B) can be used for lashing and constraining the elongate members 837 of the distal anchoring member 836 to the covering component 832 and elongate members 834 of the occlusive member 831. In some embodiments, a combination of such techniques and other techniques (e.g., clips, adhesives, welds, etc.) can be used for lashing and constraining the elongate members 837 of the distal anchoring member 836 to the covering component 832 and elongate members 834 of the occlusive member 831.

FIGS. 33A through 33D illustrate another occlusive device 840. The occlusive device 840 includes an occlusive member 841 and a distal anchoring member 846. The occlusive member 841 includes an occlusive face 842, a laterally facing skirt 843, a covering component 844, and an inverted section 845.

The distal anchoring member 846 includes a frame of multiple elongate members 847, and a substrate 848. The substrate 848 is at least partially bonded (e.g., using FEP), laminated, or otherwise attached to the elongate members 847. In some embodiments, the substrate can be a densified ePTFE material. In some embodiments, other types of sheet materials can be used, including but not limited to, PTFE, a polyester, DACRON, a silicone, a urethane, or another biocompatible polymer, or combinations thereof.

In some embodiments, the distal anchoring member 846, including the frame of multiple elongate members 847 and the substrate 848, can be attached to the occlusive member 841 near the distal end of the laterally facing skirt 843. For example, in some embodiments the frame of multiple elongate members 847 and the substrate 848 of the distal anchoring member 846 is attached to the elongate members of the occlusive member 841 and/or the covering 844 of the occlusive member 841 as described in reference to FIGS. 31A, 31B, and 32 (e.g., using suture knots, an overhand running stitch, and the like). In some embodiments, the substrate 848 provides additional surface with which to attach the distal anchoring member 846 to the occlusive member 841. For example, in FIG. 33B a suture element 849 is used to stitch the substrate 848 to the covering component 844. The suture element 849 can also be used to lash the elongate members 847 to the elongate members of the occlusive member 841 and to the covering component 844. In such a manner, the distal anchoring member 846 can, optionally, be securely attached to the occlusive member 841 near the distal end of the laterally facing skirt 843.

Figure 34C:
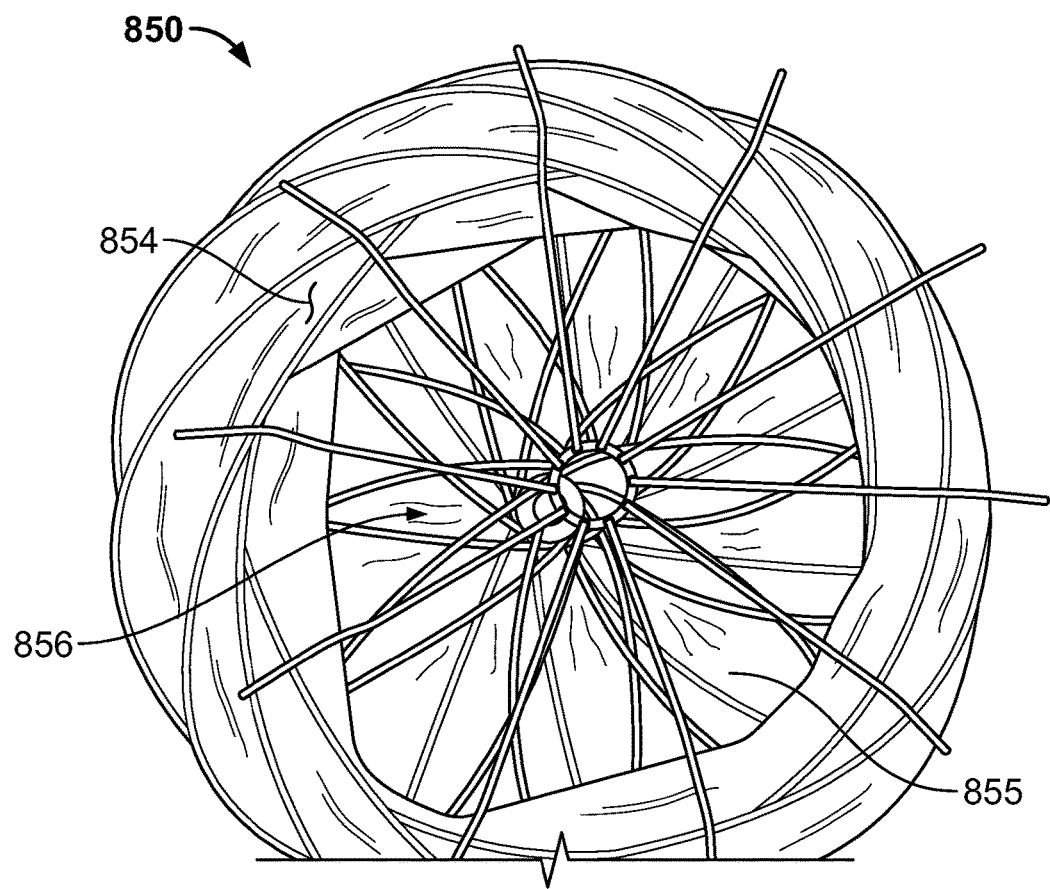
FIGS. 34C and 34D are additional views of the occlusive device of FIG. 34A.
Figure 34D:
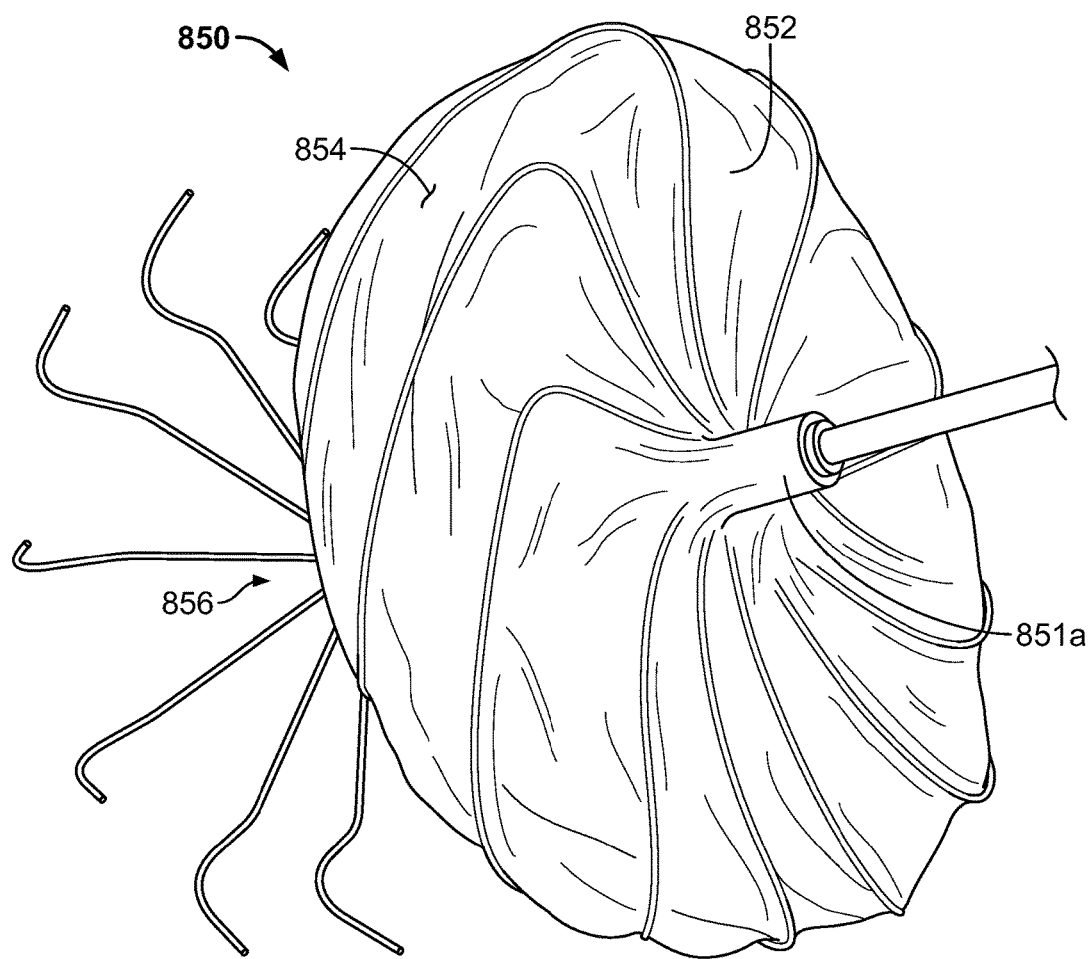

FIGS. 34A, 34C, and 34D show another example occlusive device 850 that includes a distal anchoring member 856. FIG. 34B illustrates an example distal anchoring member 856 that can be a component part of the occlusive device 850.

Referring to FIG. 34B, the example distal anchoring member 856 can include a frame with an anchoring portion 857, a proximal bulbous portion 858, and hubs 859a and 859b. The distal anchoring member 856 can be made of a material that is cut and expanded (such as shown in FIGS. 34A, 34C, and 34D) or of elongate members that are coupled together using hubs of various types (such as shown in FIG. 34B).

Referring to FIGS. 34A, 34C, and 34D, the example occlusive device 850 includes the distal anchoring member 856 and an occlusive member 851. The occlusive member 851 includes a hub 851a, an occlusive face 852, a laterally facing skirt 853, a covering component 854, and an inverted section 855.

In some embodiments, the distal anchoring member 856 is coupled to the occlusive member 851 in one or more of the following ways. For example, the hub 859a of the distal anchoring member 856 can be coupled to the hub 851a of the occlusive member 851. Such coupling of the hubs 859a and 851*a* can be accomplished using the various techniques for coupling hubs that are described elsewhere herein (e.g., using coupling elements such as an adhesive (such as FEP), a weld, a mechanical coupling element (such as a joint, rivet (e.g., a barbell rivet)), or various types of catch members). Additionally, or as an alternative, the distal anchoring member 856 can be coupled to the occlusive member 851 using the suturing techniques described in reference to FIGS. 31A, 31B, and 32 (e.g., using suture knots, an overhand running stitch, and the like). A substrate may be included on the distal anchoring member 856 as described in reference to FIGS. 33A-33D. Additionally, or as an alternative, the distal anchoring member 856 can be coupled to the occlusive member 851 using an interference fit between the bulbous portion 858 and the interior of the occlusive member 851. That is, the outer diameter of the bulbous portion 858 can be larger than the interior of the occlusive member 851 thereby providing a coupling between the distal anchoring member 856 and the occlusive member 851.

Figure 35:
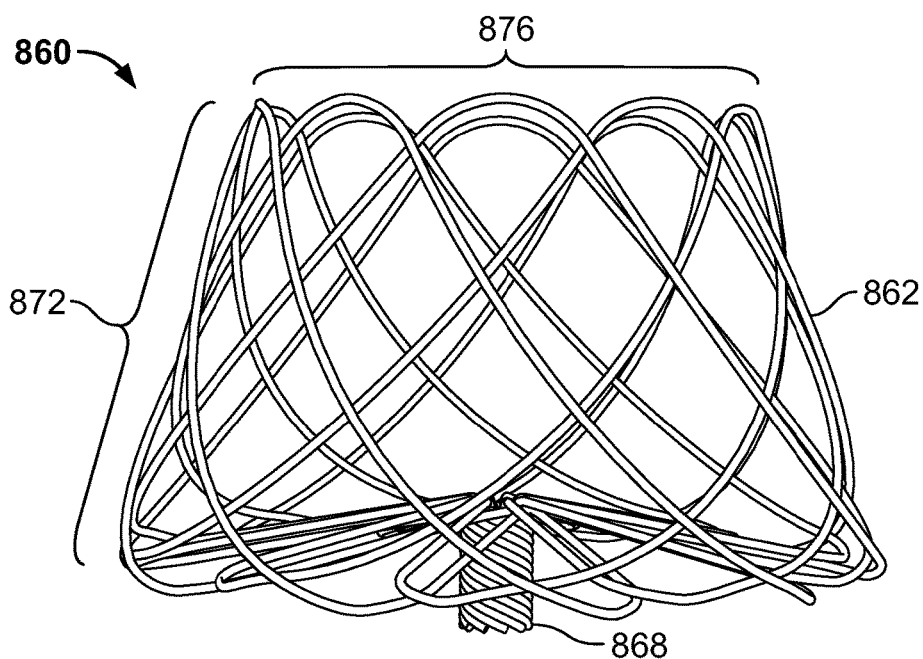
FIG. 35 is a side view of an example occlusive device frame embodiment.
Figure 36:
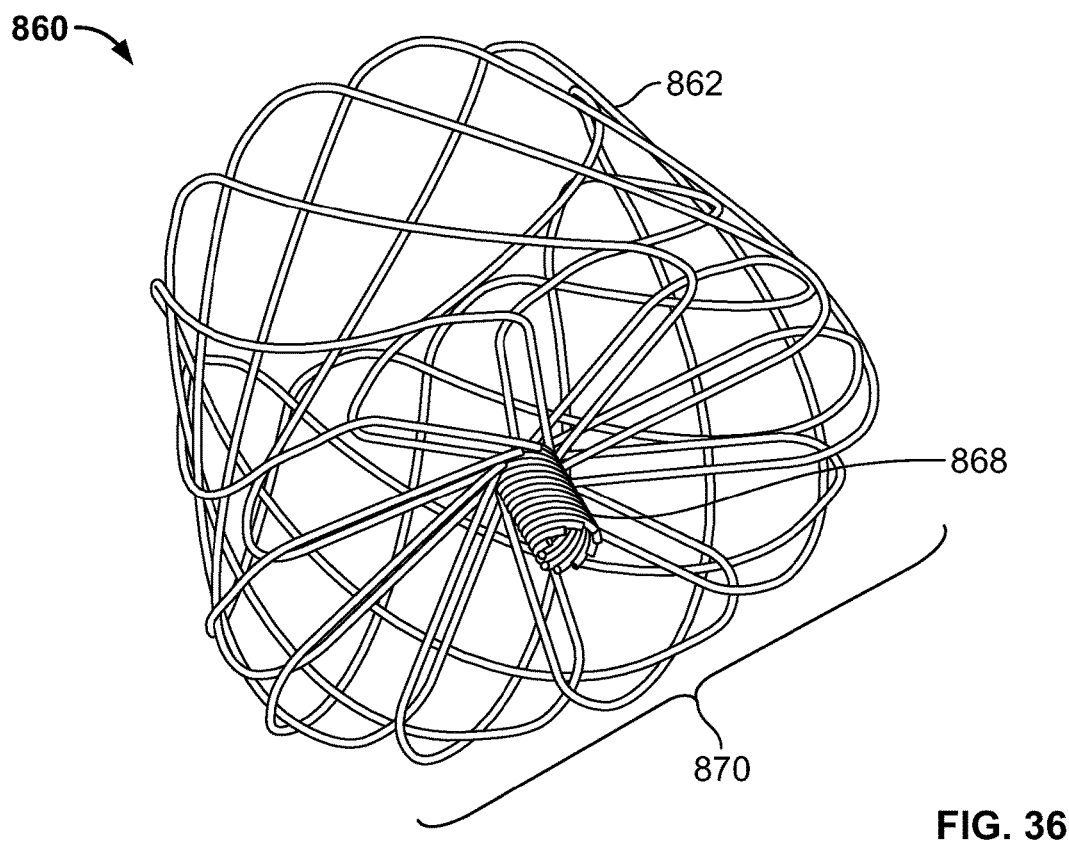
FIG. 36 is a perspective view of the example occlusive device frame of FIG. 35.

FIGS. 35 and 36 illustrate another example occlusive device frame 860 in a side view and proximal perspective view respectively. In the depicted embodiment, the occlusive device frame 860 comprises a plurality of elongate members 862 that are wound to form the occlusive device frame 860. The elongate members 862 can share any or all of the features, characteristics, properties, etc. as described above in reference to the elongate members 102 and/or any other exemplary elongate members described herein. In some embodiments, the elongate members 862 can be formed from a cut-tube process as described above.

In the depicted embodiment of occlusive device frame 860, the elongate members 862 form an occlusive face 870, a lateral skirt 872, an inverted section 876, and hub members 868 that are nested eyelets 868. It should be understood that, in some embodiments of occlusive device frame 860, the occlusive face 870, the lateral skirt 872, the inverted section 876, and the hub members 868 can share any or all of the features, characteristics, properties, etc. as described above in reference to all other occlusive devices provided herein.

The occlusive device frame 860 can be combined with a covering component in some embodiments. The covering component can share any or all of the features, characteristics, properties, etc. as described above in reference to the covering component 104 and/or any other exemplary covering components described herein.

While the depicted embodiment of occlusive device frame 860 includes the nested eyelets 868 as the hub members, in some embodiments of occlusive device frame 860 one or both of the hub members may be any of the other types of hub members described elsewhere herein (e.g., ring members, crimp joints, tube portions, and combinations thereof).

Figure 37:
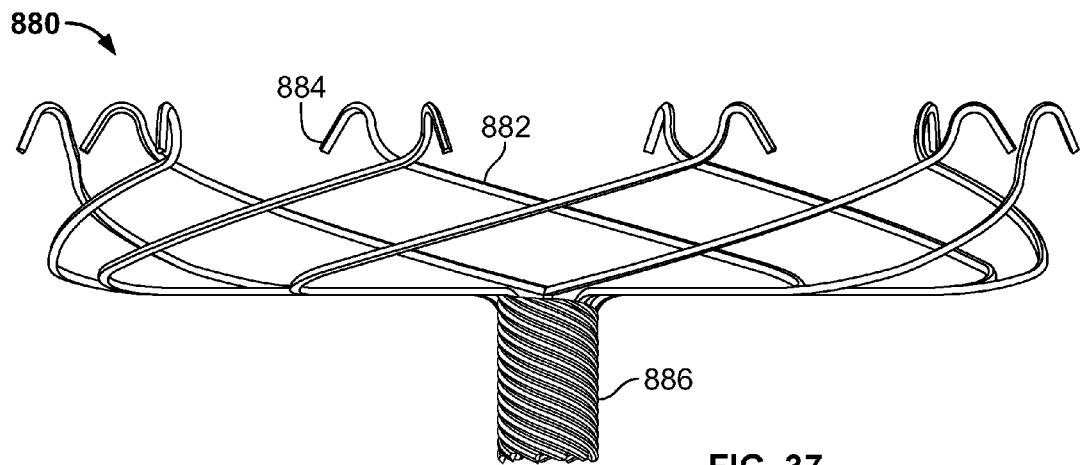
FIG. 37 is a side view of an example anchor frame embodiment.

FIG. 37 illustrates an example anchor frame 880 that can be included as part of the occlusive devices provided herein. In the depicted embodiment, the anchor frame 880 comprises a plurality of elongate members 882 that are wound to form the anchor frame 880. The elongate members 882 can share any or all of the features, characteristics, properties, etc. as described above in reference to the elongate members 102 and/or any other exemplary elongate members described herein. In some embodiments, the elongate members 882 can be formed from a cut-tube process as described above.

In the depicted embodiment of anchor frame 880, the elongate members 882 form anchor arms 884 and a hub member 886 that is an eyelet 886. It should be understood that, in some embodiments of the anchor frame 880, the anchor arms 884 and the hub member 886 can share any or all of the features, characteristics, properties, etc. as described above in reference to all other anchor frames provided herein. For example, the free ends of the anchor arms 884 can be configured to have sharp tips, atraumatic tips, barbs, ball-ends, or other types of tips, or combinations thereof, as described above in reference to anchor features 600. In the depicted embodiment of anchor frame 880, the anchor arms 884 extend along a generally helical path. In some embodiments, the anchor arms 884 can extend along other paths such as, but not limited to, parallel to the central axis of the eyelet 886, a helical path that is reversed in direction from what is shown, helical paths at various different pitch angles, wavy paths, wound around the elongate elements of the occlusive device frame, and the like, and combinations thereof.

Figure 38:
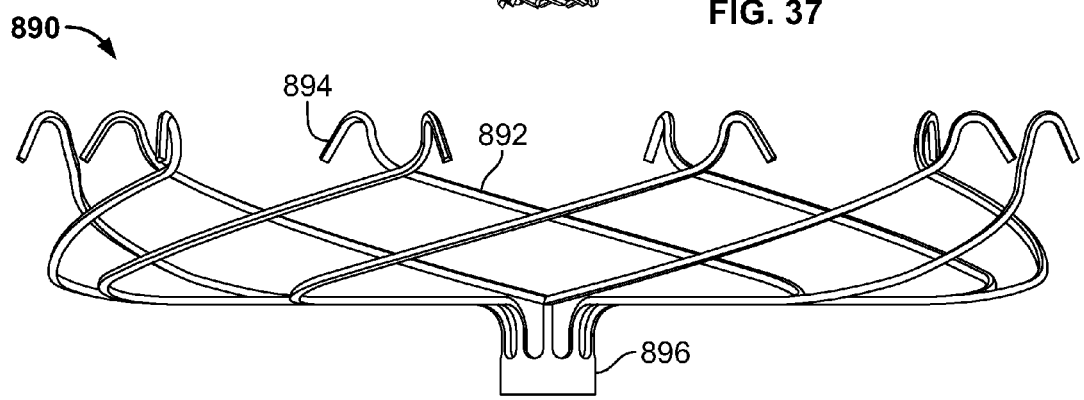
FIG. 38 is a side view of another example anchor frame embodiment.
Figure 39:
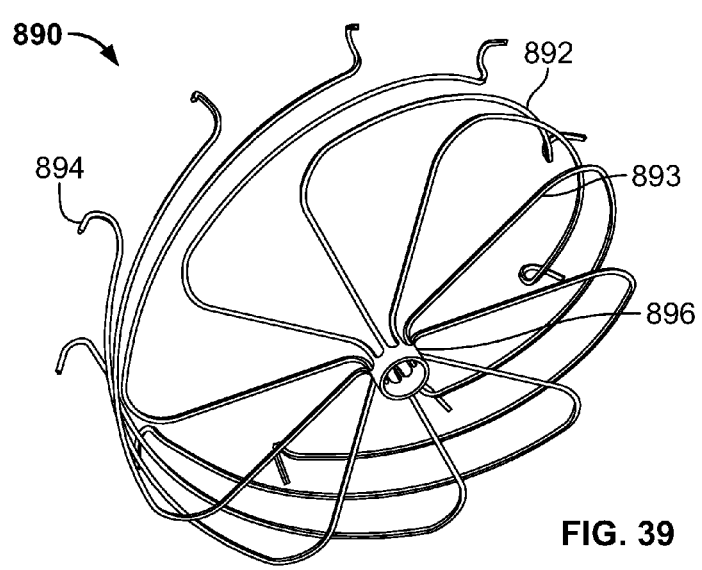
FIG. 39 is a perspective view of the example anchor frame of FIG. 38.

FIGS. 38 and 39 illustrate a side view and a proximal perspective view, respectively, of another example anchor frame 890 that can be included as part of the occlusive devices provided herein. In the depicted embodiment, the anchor frame 890 comprises a plurality of elongate members 892 that are formed from a cut-tube process as described above. The elongate members 892 can share any or all of the features, characteristics, properties, etc. as described above in reference to the elongate members 102 and/or any other exemplary elongate members described herein. In some embodiments, the elongate members 892 can be wound to form the anchor frame 890, as described above.

In the depicted embodiment of anchor frame 890, the elongate members 892 form one or more anchor arms 894 and a hub member 896 comprising a portion of a tube. Radial struts 893 extend radially outward from the hub member 896 and then transition into the anchor arms 894. It should be understood that, in some embodiments of the anchor frame 890, the anchor arms 894, the radial struts 893, and the hub member 896 can share any or all of the features, characteristics, properties, etc. as described above in reference to all other anchor frames provided herein. For example, the free ends of the anchor arms 894 can be configured to have sharp tips, atraumatic tips, barbs, ball-ends, or other types of tips, or combinations thereof, as described above in reference to anchor features 600. In the depicted embodiment of anchor frame 890, the anchor arms 894 extend along a generally helical path. In some embodiments, the anchor arms 894 can extend along other paths such as, but not limited to, parallel to the central axis of the eyelet 896, a helical path that is reversed in direction from what is shown, helical paths at various different pitch angles, wavy paths, and the like, and combinations thereof.

Figure 40:
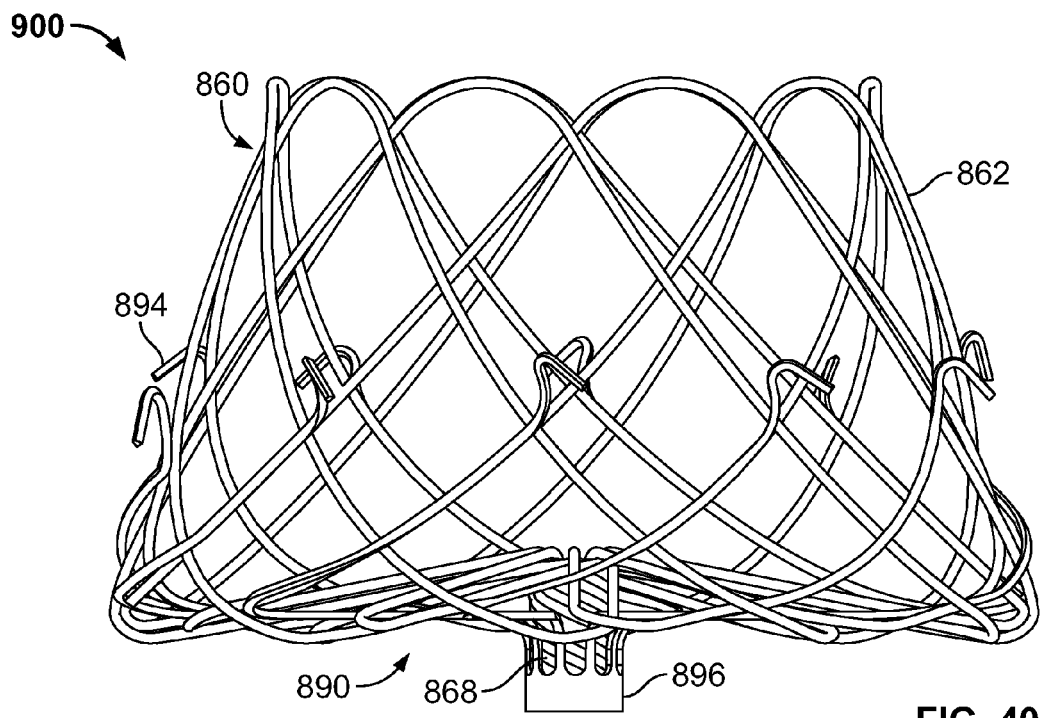
FIG. 40 is a side view of another example occlusive device frame embodiment.
Figure 41:
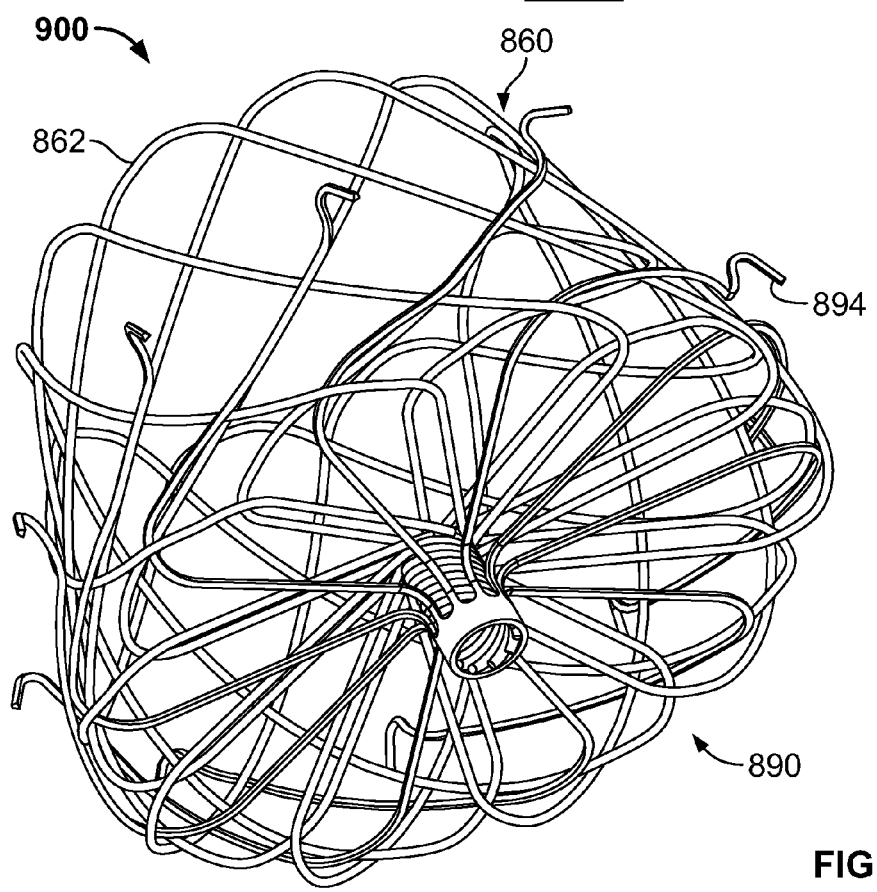
FIG. 41 is a perspective view of the example occlusive device frame of FIG. 40.

FIGS. 40 and 41 illustrate a side view and a proximal perspective view, respectively, of an example occlusive device 900. The occlusive device 900 includes the occlusive device frame 860 (as described above) coupled with the anchor frame 890 (as described above). In some embodiments, the occlusive device 900 includes the occlusive device frame 860 coupled with the anchor frame 880 (refer to FIG. 37), or another anchor frame provided herein. In some embodiments, the occlusive device 900 includes the anchor frame 890 (or anchor frame 880) coupled with another occlusive device frame provided herein.

It should be understood that the occlusive device 900 can be combined with a covering component in some embodiments. The covering component can share any or all of the features, characteristics, properties, etc. as described above in reference to the covering component 104 and/or any other exemplary covering components described herein.

In the depicted embodiment of occlusive device 900, the hub members 868 (i.e., the nested eyelets 868) of the occlusive device frame 860 are located within the hub member 896 of the anchor frame 890. In some embodiments, the hub members 868 and 896 are configured in other arrangements. For example, in some embodiments the hub member 896 is located within both of the hub members 868. Further, in some embodiments the hub member 896 is nested in between the inner and outer hub members of the hub members 868.

In some embodiments, the anchor arms 894 are interwoven with the elongate members 862 of the occlusive device frame 860. The interweaving of the anchor arms 894 with the elongate members 862 can be configured in all possible arrangements as long as the free ends of the anchor arms 894 protrude from the lateral skirt 872 of the occlusive device frame 860.

In the depicted embodiment of occlusive device 900, the anchor arms 894 protrude from the lateral skirt 872 in the area of the proximal end of the lateral skirt 872. In some embodiments of occlusive device 900, the anchor arms 894 protrude from the lateral skirt 872 in the area of the distal end of the lateral skirt 872. In some embodiments of occlusive device 900, the anchor arms 894 protrude from the lateral skirt 872 in the mid-body area between the proximal end of the lateral skirt 872 and the distal end of the lateral skirt 872. In some embodiments of occlusive device 900, the anchor arms 894 have dissimilar lengths and protrude from the lateral skirt 872 at different areas along the lateral skirt 872 (e.g., some protrude from the proximal end area while others protrude from the mid-body area, or some protrude from the distal end area while others protrude from the mid-body area, or some protrude from the proximal end area while others protrude from the distal end area).

Figure 42:
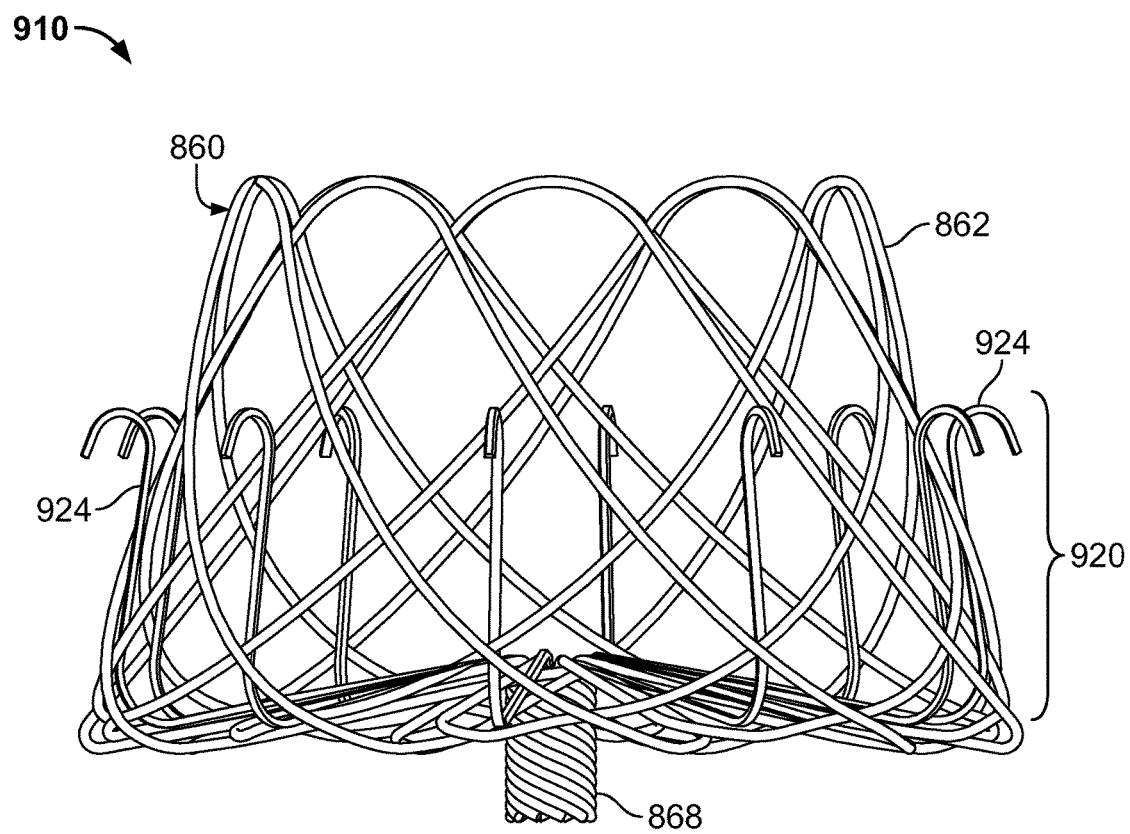
FIG. 42 is a side view of another example occlusive device frame embodiment.

FIG. 42 is a side view of another example occlusive device 910. The occlusive device 910 includes the occlusive device frame 860 (as described above) coupled with an anchor frame 920. In some embodiments, the occlusive device 910 includes the occlusive device frame 860 coupled with the anchor frame provided herein. In some embodiments, the occlusive device 910 includes the anchor frame 920 coupled with another occlusive device frame provided herein.

It should be understood that the occlusive device 910 can be combined with a covering component in some embodiments. The covering component can share any or all of the features, characteristics, properties, etc. as described above in reference to the covering component 104 and/or any other exemplary covering components described herein.

The anchor frame 920 includes a hub member (not visible) and anchor arms 924. In some embodiments, the anchor frame 920 is formed using a cut-tube process as described elsewhere herein. In some embodiments, the anchor frame 920 is formed by winding multiple wires as described elsewhere herein.

In the depicted embodiment of the occlusive device 910, the anchor arms 924 extend along the lateral skirt 872 of the occlusive device frame 860 in a direction generally parallel to the axis of the nested eyelets 868. In some embodiments of the occlusive device 910, the anchor arms 924 extend along the lateral skirt 872 in a helical pattern, or another pattern. In the depicted embodiment of the occlusive device 910, the anchor arms 924 are at least partially interwoven with the elongate element 924 of the occlusive device frame 860. In some embodiments of the occlusive device 910, the anchor arms 924 are more interwoven or less interwoven with the elongate element 924 of the occlusive device frame 860 in comparison to the depicted embodiment.

In the depicted embodiment of the occlusive device 910, the hub member of the anchor frame 920 is located between the inner and outer hub members 868 (i.e., the hub member of the anchor frame 920 is sandwiched between the nested eyelets 868) of the occlusive device frame 860. In some embodiments, the hub member of the anchor frame 920 and the hub members 868 are configured in other arrangements. For example, in some embodiments the hub member of the anchor frame 920 is located within the inner hub member of the nested eyelets 868. Further, in some embodiments the nested eyelets 868 are located within the hub member of the anchor frame 920.

In the depicted embodiment of occlusive device 910, the anchor arms 924 protrude from the lateral skirt 872 in the mid-body area between the proximal end of the lateral skirt 872 and the distal end of the lateral skirt 872. In some embodiments of the occlusive device 910, the anchor arms 924 protrude from the lateral skirt 872 the area of the proximal end of the lateral skirt 872. In some embodiments of occlusive device 910, the anchor arms 924 protrude from the lateral skirt 872 in the area of the distal end of the lateral skirt 872. In some embodiments of occlusive device 910, the anchor arms 924 have dissimilar lengths and protrude from the lateral skirt 872 at different areas along the lateral skirt 872 (e.g., some protrude from the proximal end area while others protrude from the mid-body area, or some protrude from the distal end area while others protrude from the mid-body area, or some protrude from the proximal end area while others protrude from the distal end area).

FIGS. 43-46 schematically represent additional embodiments of occlusive devices 920, 930, 940, and 950, respectively. In some embodiments, the occlusive devices 920, 930, 940, and 950 include frames with features as described above such as an occlusive face, a laterally facing skirt, and an inverted section. Additionally, in some embodiments the occlusive devices 920, 930, 940, and 950 include an anchor frame that is integrated with the occlusive device frame. In some such embodiments, the occlusive devices 920, 930, 940, and 950 are configured such that the hub member of the anchor frames are sandwiched in between the inner and outer hub members of the occlusive device frame. FIGS. 43-46 are drawn to highlight particular occlusive device frame features that can be incorporated into the designs of the occlusive devices provided herein. For example, in some of the figures the designs of the hub members, anchor frames, and/or occlusion frames are highlighted. It should be understood that one or more of the features that are highlighted in these figures can be included in any of the occlusive devices described elsewhere herein, and that such features (and other features described herein) can be mixed and matched to create hybrid designs that are entirely within the scope of this disclosure. In these figures, no covering component is shown and some portions of the frames are not shown so that the highlighted frame features are more readily visible. It should be understood that the occlusive devices of FIGS. 43-46 can be combined with a covering component in some embodiments. The covering component can share any or all of the features, characteristics, properties, etc. as described above in reference to the covering component 104 and/or any other exemplary covering components described herein.

It should be understood that the hub members of the anchor frames and/or the occlusive device frame may be any of the types of hub members described herein (e.g., eyelets, ring members, crimp joints, tube portions, etc.). In some embodiments, the hub members of the anchor frames and the hub members of the occlusive device frame are configured in other arrangements in relation to each other. For example, in some embodiments the hub member of the anchor frame is located within both of the hub members of the occlusive device frame. Further, in some embodiments the hub members of the occlusive device frame are located within the hub member of the anchor frame. That is, in some embodiments the hub member of the anchor frame is the outermost hub member of the arrangement.

It should be understood that the occlusive devices 920, 930, 940, and 950 can be combined with a covering component in some embodiments. The covering component can share any or all of the features, characteristics, properties, etc. as described above in reference to the covering component 104 and/or any other exemplary covering components described herein.

Figure 43:
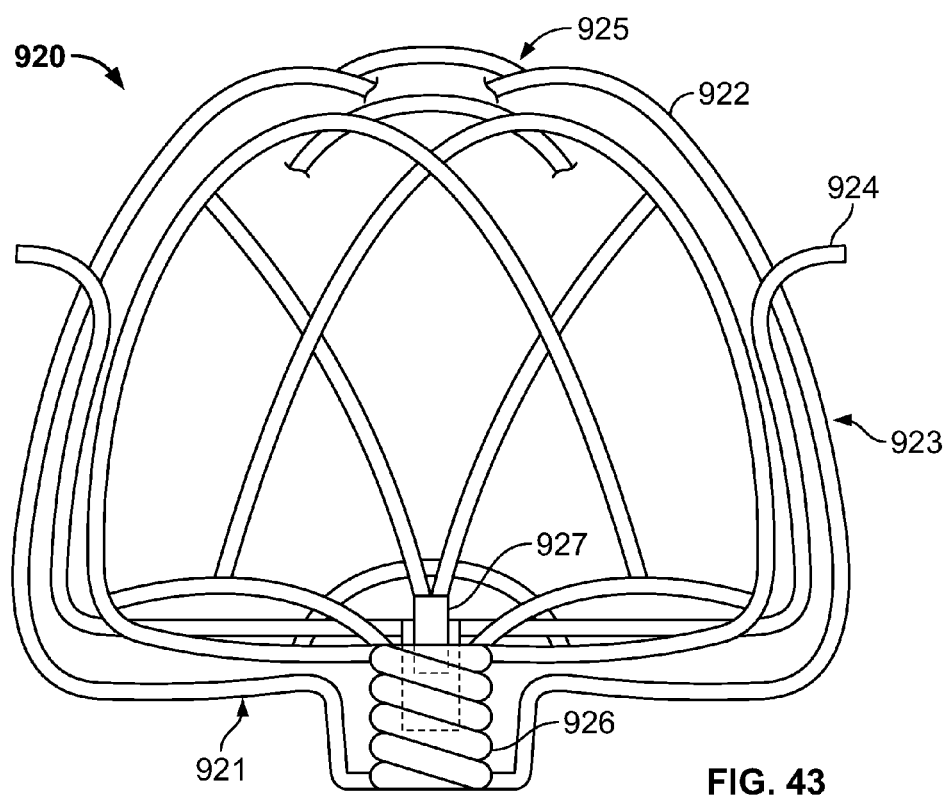
FIG. 43 is a conceptual diagram of a portion of yet another example occlusive device frame.

FIG. 43 is a conceptual diagram of a portion of an example occlusive device frame 922 that is coupled with an anchor frame 924. As with some occlusive device embodiments described elsewhere herein, the occlusive device frame 922 includes an occlusive face 921, a laterally facing skirt 923, and an inverted section 925. In the depicted embodiment, the occlusive device frame 922 has a wound wire construct, while the anchor frame 924 was formed using a cut-tube process. The inner hub member of the occlusive device frame 922 is a ring member 927 and the outer hub member of the occlusive device frame 922 is an eyelet 926. The hub member of the anchor frame 924 is a tube portion (not shown) that is sandwiched between the inner hub member 927 and outer hub member 926 of the occlusive device frame 922. The free ends of the anchor frame 924 protrude from the mid-body area of laterally facing skirt 923 of the occlusive device frame 922 to provide additional migration resistance for occlusive device 920.

Figure 44:
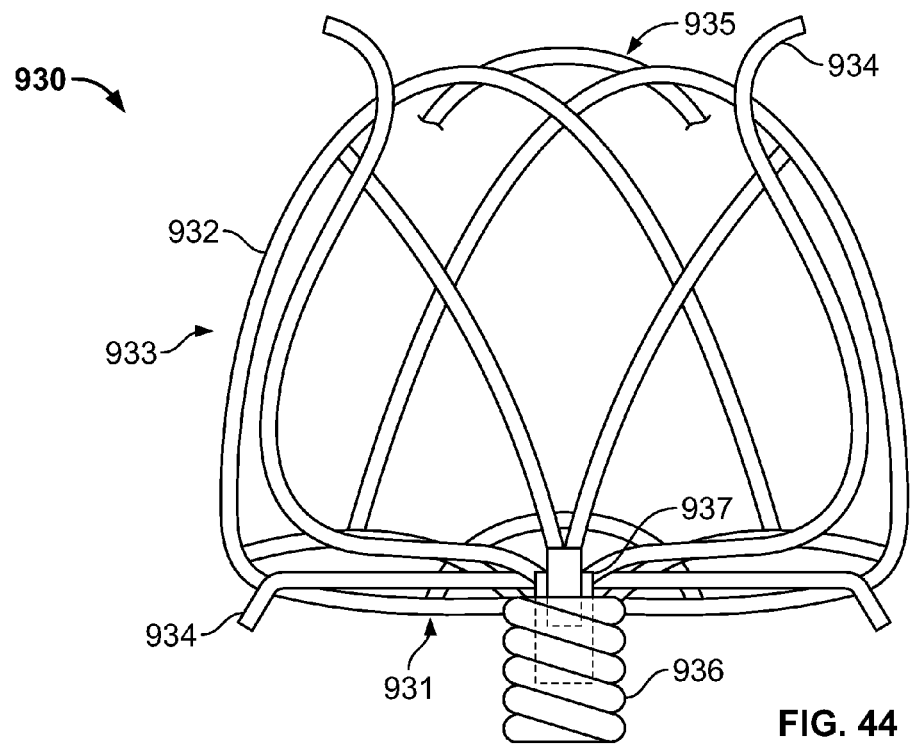
FIG. 44 is a conceptual diagram of a portion of yet another example occlusive device frame.

FIG. 44 is a conceptual diagram of a portion of an example occlusive device frame 932 that is coupled with an anchor frame 934. As with some occlusive device embodiments described elsewhere herein, the occlusive device frame 932 includes an occlusive face 931, a laterally facing skirt 933, and an inverted section 935. In the depicted embodiment, the occlusive device frame 932 has a wound wire construct, while the anchor frame 934 was formed using a cut-tube process. The inner hub member of the occlusive device frame 932 is a ring member 937 and the outer hub member of the occlusive device frame 932 is an eyelet 936. The hub member of the anchor frame 934 is a tube portion (not shown) that is sandwiched between the inner hub member 937 and the outer hub member 936 of the occlusive device frame 932. The free ends of the anchor frame 934 protrude from both the distal area of the occlusive device frame 932 and the proximal area of the occlusive device frame 932 to provide additional migration resistance for occlusive device 930.

Figure 45:
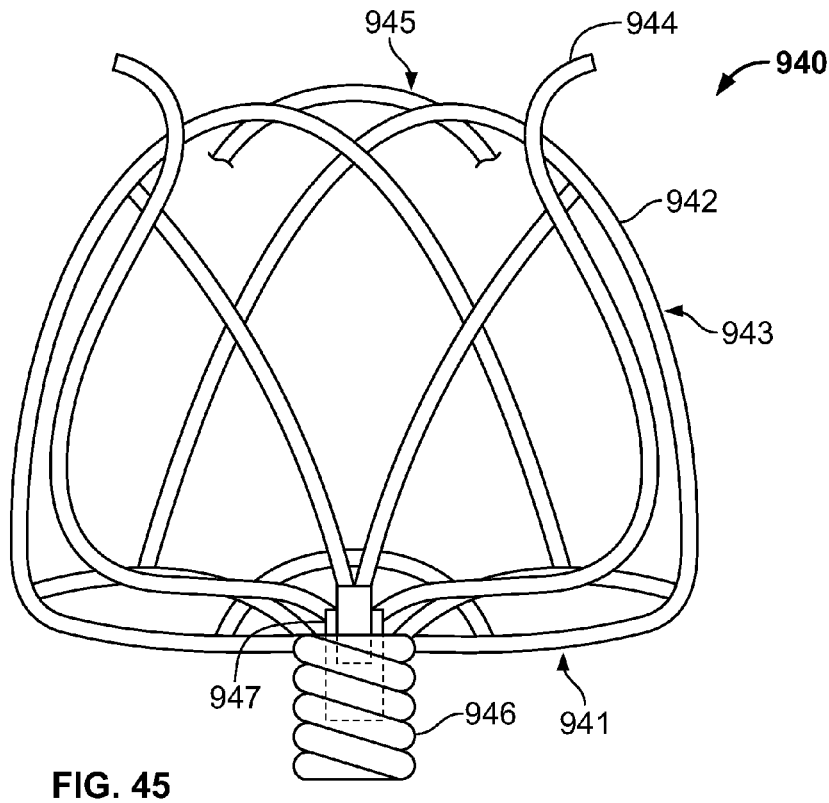
FIG. 45 is a conceptual diagram of a portion of yet another example occlusive device frame.

FIG. 45 is a conceptual diagram of a portion of an example occlusive device frame 942 that is coupled with an anchor frame 944. As with some occlusive device embodiments described elsewhere herein, the occlusive device frame 942 includes an occlusive face 941, a laterally facing skirt 943, and an inverted section 945. In the depicted embodiment, the occlusive device frame 942 has a wound wire construct, while the anchor frame 944 was formed using a cut-tube process. The inner hub member of the occlusive device frame 942 is a ring member 947 and the outer hub member of the occlusive device frame 942 is an eyelet 946. The hub member of the anchor frame 944 is a tube portion (not shown) that is sandwiched between the inner hub member 947 and the outer hub member 946 of the occlusive device frame 942. The free ends of the anchor frame 944 protrude from the distal area of the occlusive device frame 942 to provide additional migration resistance for occlusive device 940.

Figure 46:
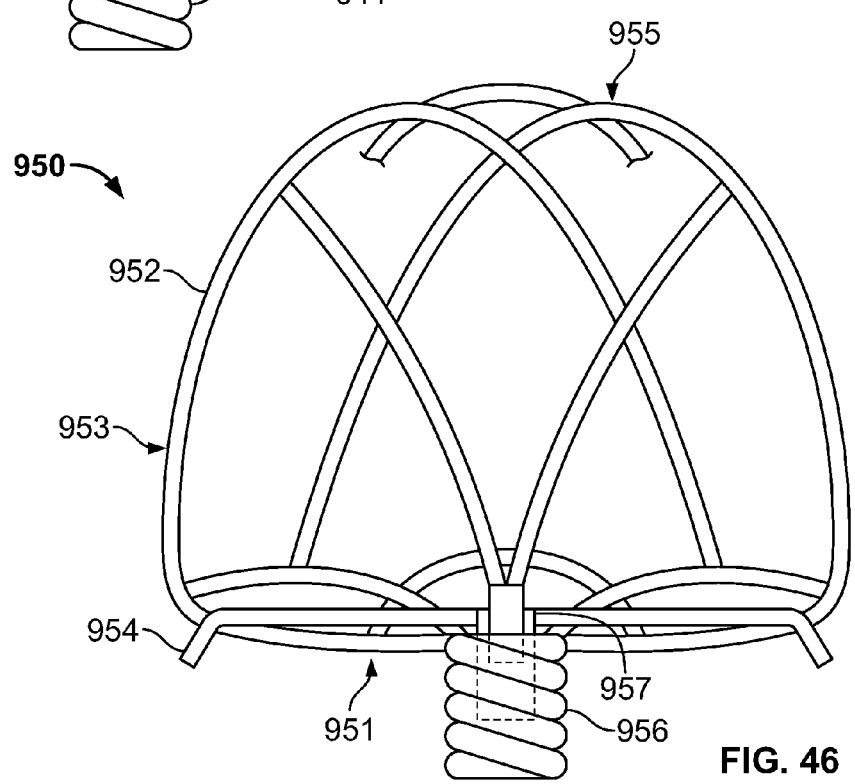
FIG. 46 is a conceptual diagram of a portion of yet another example occlusive device frame.

FIG. 46 is a conceptual diagram of a portion of an example occlusive device frame 952 that is coupled with an anchor frame 954. As with some occlusive device embodiments described elsewhere herein, the occlusive device frame 952 includes an occlusive face 951, a laterally facing skirt 953, and an inverted section 955. In the depicted embodiment, the occlusive device frame 952 has a wound wire construct, while the anchor frame 954 was formed using a cut-tube process. The inner hub member of the occlusive device frame 952 is a ring member 957 and the outer hub member of the occlusive device frame 952 is an eyelet 956. The hub member of the anchor frame 954 is a tube portion (not shown) that is sandwiched between the inner hub member 957 and the outer hub member 956 of the occlusive device frame 952. The free ends of the anchor frame 954 protrude from the proximal area of the occlusive device frame 952, to provide additional migration resistance for occlusive device 950.

Figure 47:
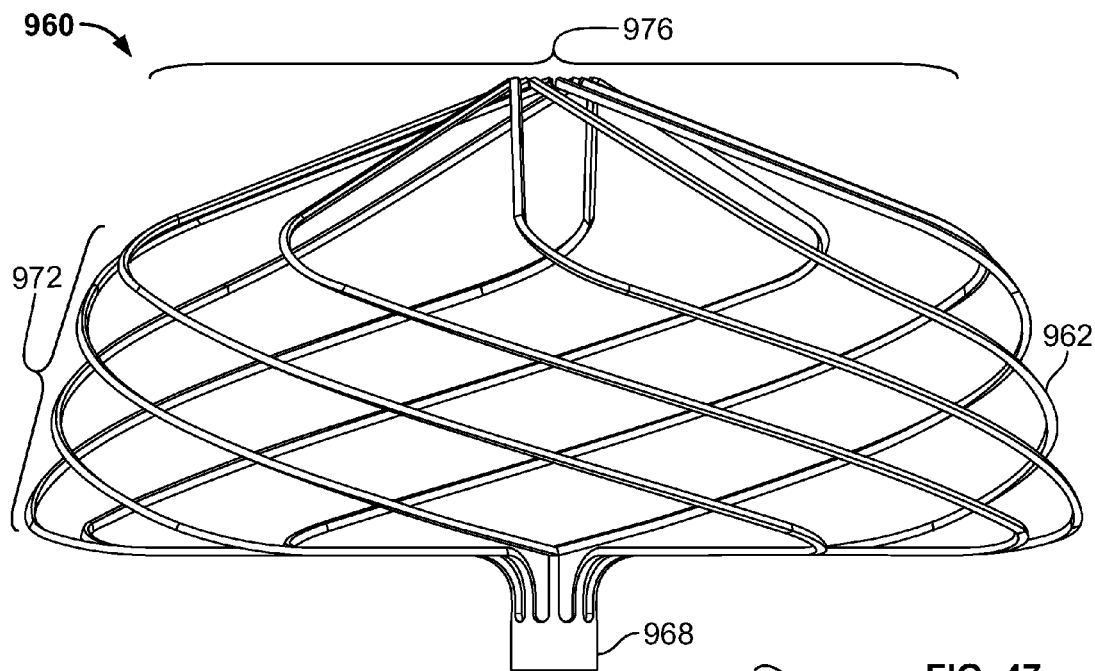
FIG. 47 is a side view of another example occlusive device frame embodiment.
Figure 48:
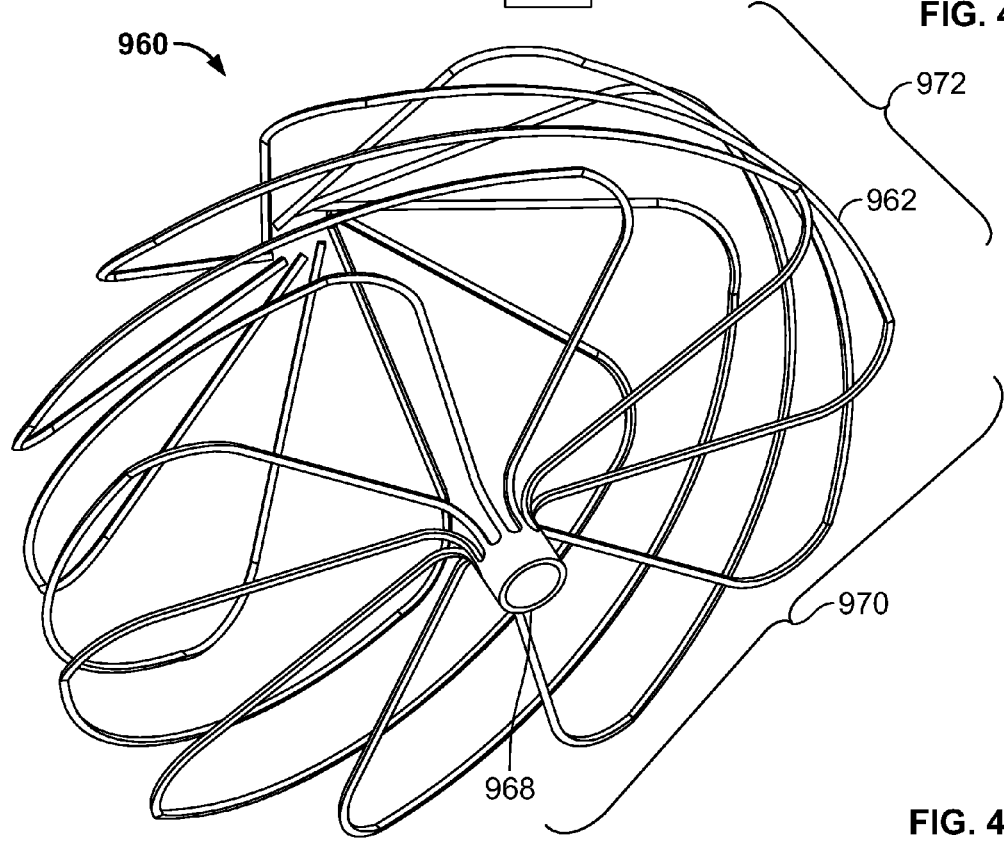
FIG. 48 is a perspective view of the example occlusive device frame of FIG. 47.

FIGS. 47 and 48 illustrate another example occlusive device frame 960 in a side view and proximal perspective view respectively. In the depicted embodiment, the occlusive device frame 960 comprises a plurality of elongate members 962 that are formed from a cut-tube process to form the occlusive device frame 960. The elongate members 962 can share any or all of the features, characteristics, properties, etc. as described above in reference to the elongate members 102 and/or any other exemplary elongate members described herein. In some embodiments, the elongate members 962 can be formed from a wound wire process as described above.

In the depicted embodiment of occlusive device frame 960, the elongate members 962 form an occlusive face 970, a lateral skirt 972, a convex section 976, and a hub member 968 that is a tube portion. It should be understood that, in some embodiments of occlusive device frame 960, the occlusive face 970, the lateral skirt 972, the convex section 976, and the hub member 968 can share any or all of the features, characteristics, properties, etc. as described above in reference to all other occlusive devices provided herein.

The convex section 976 includes the free ends of the elongate elements 962. In some embodiments, some or all of the free ends of the elongate elements 962 are conjoined together. In some embodiments, the free ends of the elongate elements 962 are not conjoined together and are allowed to move independently of each other. In some embodiments the convex section 976 is a concaved or inverted section.

The occlusive device frame 960 can be combined with a covering component in some embodiments. The covering component can share any or all of the features, characteristics, properties, etc. as described above in reference to the covering component 104 and/or any other exemplary covering components described herein.

While the depicted embodiment of occlusive device frame 960 includes the tube portion 868 as the hub member, in some embodiments of occlusive device frame 960 the hub member 868 may be any of the other types of hub members described elsewhere herein (e.g., a ring member, a crimp joints, an eyelet, etc.).

Figure 49:
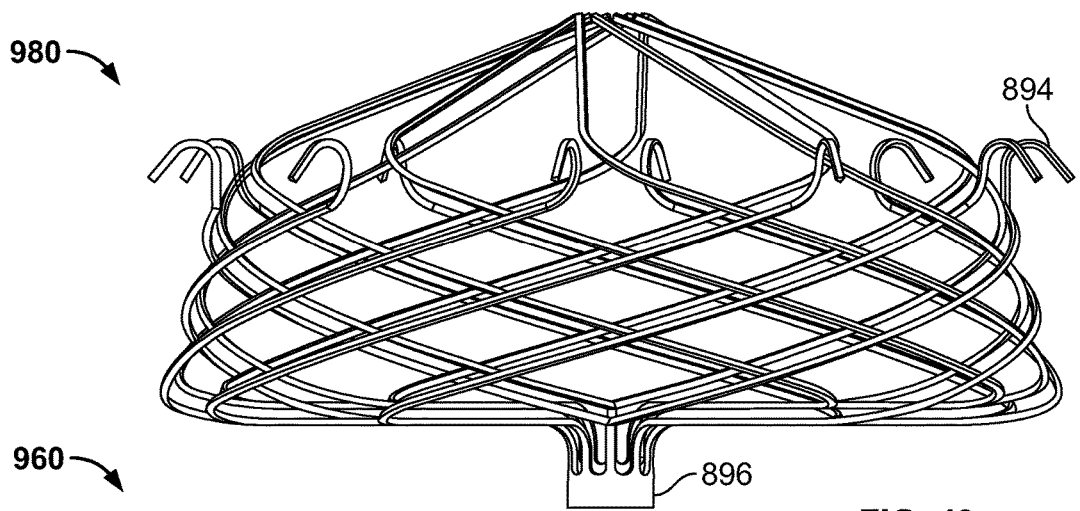
FIG. 49 is a side view of another example occlusive device frame embodiment.
Figure 50:
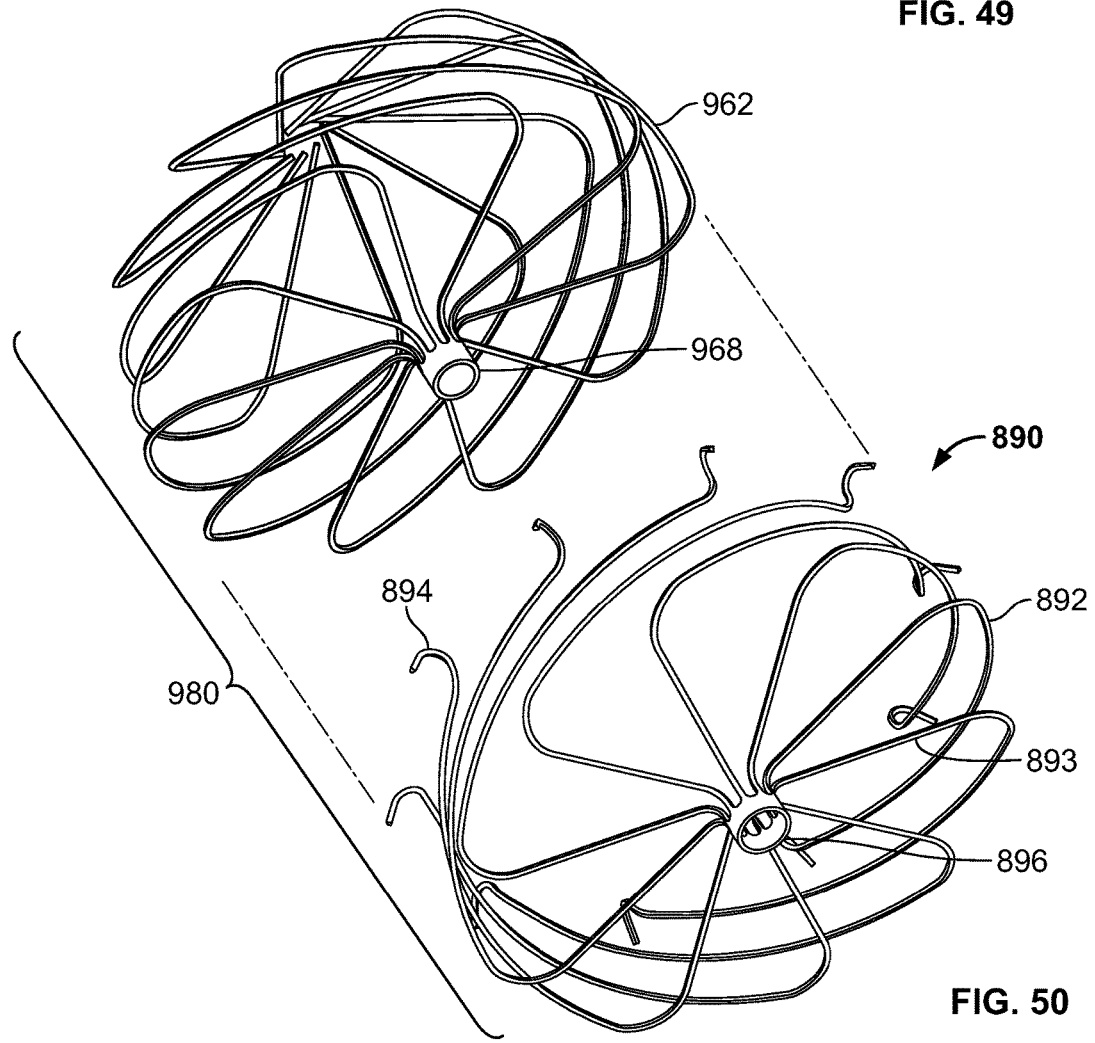
FIG. 50 is an exploded view of the example occlusive device frame of FIG. 49.

FIGS. 49 and 50 illustrate a side view and a proximal exploded perspective view, respectively, of an example occlusive device 980. The occlusive device 980 includes the occlusive device frame 960 (as described above) coupled with the anchor frame 890 (as described above in reference to FIGS. 38 and 39). In some embodiments, the occlusive device 980 includes the occlusive device frame 960 coupled with the anchor frame 880 (refer to FIG. 37), or another anchor frame provided herein. In some embodiments, the occlusive device 980 includes the anchor frame 890 (or anchor frame 880) coupled with another occlusive device frame provided herein.

It should be understood that the occlusive device 980 can be combined with a covering component in some embodiments. The covering component can share any or all of the features, characteristics, properties, etc. as described above in reference to the covering component 104 and/or any other exemplary covering components described herein.

In the depicted embodiment of occlusive device 980, the hub member 968 (i.e., the tube portion 868) of the occlusive device frame 960 is located within the hub member 896 of the anchor frame 890. In some embodiments, the hub members 968 and 896 are configured in other arrangements. For example, in some embodiments the hub member 896 is located within the hub member 968.

In some embodiments, the anchor arms 894 are interwoven with the elongate members 962 of the occlusive device frame 960. The interweaving of the anchor arms 894 with the elongate members 962 can be configured in all possible arrangements as long as the free ends of the anchor arms 894 protrude from the lateral skirt 972 of the occlusive device frame 960.

In the depicted embodiment of occlusive device 980, the anchor arms 894 protrude from the lateral skirt 972 in the area of the distal end of the lateral skirt 972. In some embodiments of occlusive device 980, the anchor arms 894 protrude from the lateral skirt 972 in the area of the proximal end of the lateral skirt 972. In some embodiments of occlusive device 980, the anchor arms 894 protrude from the lateral skirt 972 in the mid-body area between the proximal end of the lateral skirt 972 and the distal end of the lateral skirt 972. In some embodiments of occlusive device 980, the anchor arms 894 have dissimilar lengths and protrude from the lateral skirt 972 at different areas along the lateral skirt 972 (e.g., some protrude from the proximal end area while others protrude from the mid-body area, or some protrude from the distal end area while others protrude from the mid-body area, or some protrude from the proximal end area while others protrude from the distal end area).

Figure 51:
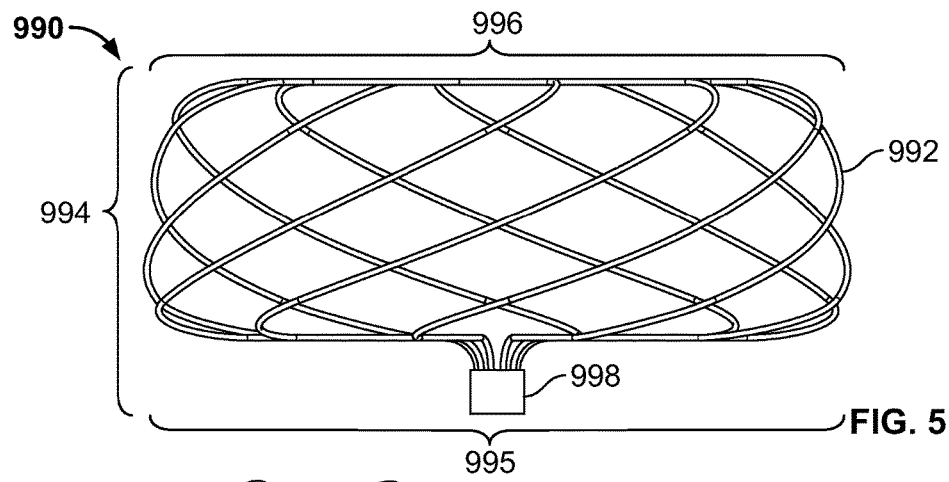
FIG. 51 is a side view of another example occlusive device frame embodiment.

FIG. 51 illustrates another example occlusive device frame 990 in a side view. In the depicted embodiment, the occlusive device frame 990 comprises a plurality of elongate members 992 that are wound to form the occlusive device frame 990. The elongate members 992 can share any or all of the features, properties, etc. as described above in reference to the elongate members 102 and/or any other exemplary elongate members described herein. In some embodiments, the elongate members 992 can be formed from a cut-tube process as described above.

In the depicted embodiment of occlusive device frame 990, the elongate members 992 define an occlusive face 995, a lateral skirt 994, and a distal face 996. It should be understood that, in some embodiments of occlusive device frame 990, the occlusive face 995, the lateral skirt 994, and the distal face 996 can share any or all of the features, characteristics, properties, etc. as described above in reference to all other occlusive devices provided herein.

The distal face 996 includes the free ends of the elongate elements 992. In some embodiments, some or all of the free ends of the elongate elements 992 are conjoined together. In some embodiments, the free ends of the elongate elements 992 are not conjoined together and are allowed to move independently of each other. In some embodiments the distal section 996 is a concaved, convexed, or inverted section.

The occlusive device frame 990 can be combined with a covering component in some embodiments. The covering component can share any or all of the features, characteristics, properties, etc. as described above in reference to the covering component 104 and/or any other exemplary covering components described herein.

While the depicted embodiment of occlusive device frame 990 includes a ring member 998 as the hub member 998. In some embodiments of the occlusive device frame 990, the hub member 998 may be any of the other types of hub members described elsewhere herein (e.g., an eyelet, a crimp joint, a tube portion, and combinations thereof).

Figure 52:
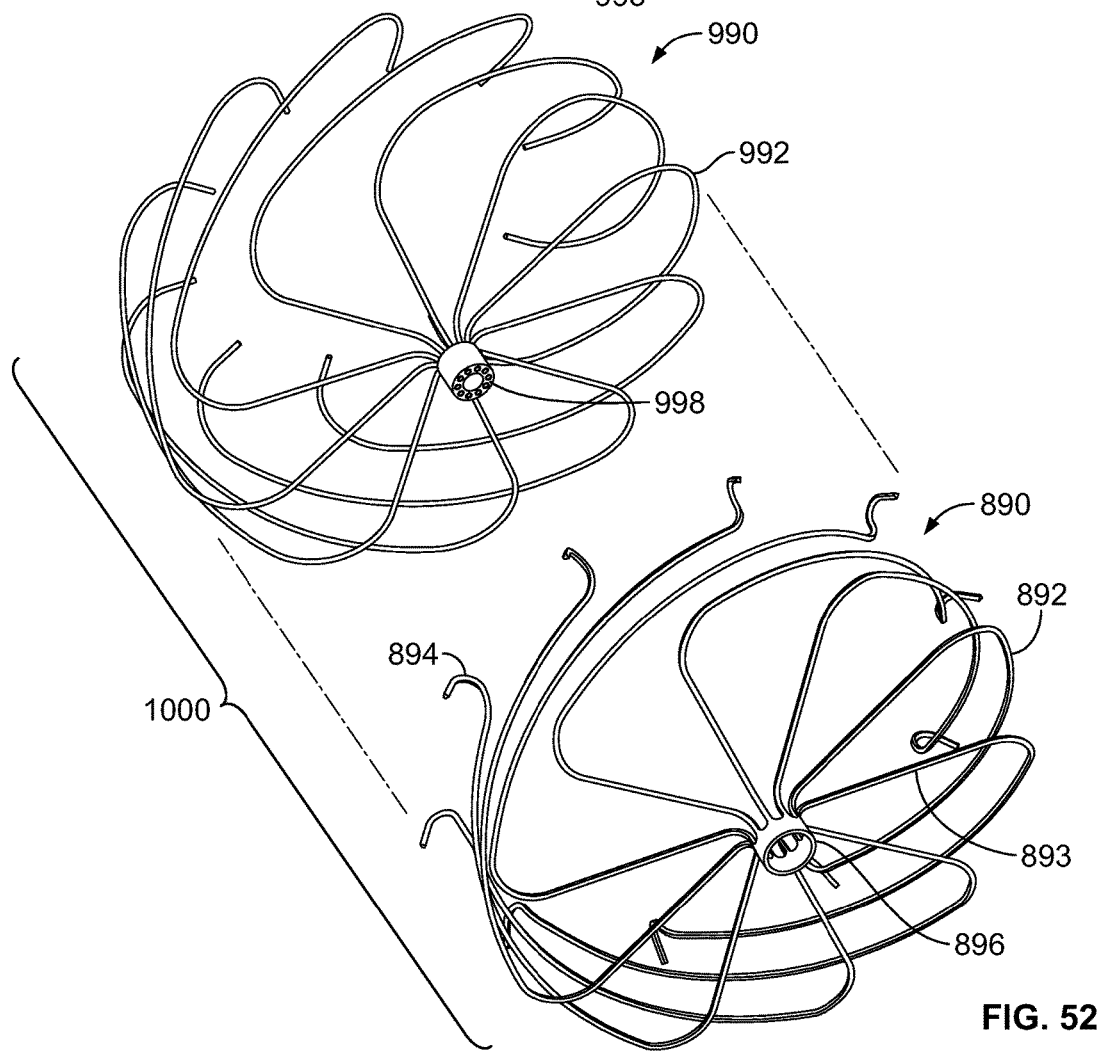
FIG. 52 is an exploded view of the example occlusive device frame of FIG. 51.

FIG. 52 illustrates a proximal exploded perspective view of an example occlusive device 1000. The occlusive device 1000 includes the occlusive device frame 990 (as described above) coupled with the anchor frame 890 (as described above in reference to FIGS. 38 and 39). In some embodiments, the occlusive device 1000 includes the occlusive device frame 990 coupled with the anchor frame 880 (refer to FIG. 37), or another anchor frame provided herein. In some embodiments, the occlusive device 1000 includes the anchor frame 890 (or anchor frame 880) coupled with another occlusive device frame provided herein.

It should be understood that the occlusive device 1000 can be combined with a covering component in some embodiments. The covering component can share any or all of the features, characteristics, properties, etc. as described above in reference to the covering component 104 and/or any other exemplary covering components described herein.

In the depicted embodiment of occlusive device 1000, the hub member 998 (i.e., the ring member 998) of the occlusive device frame 990 is located within the hub member 896 of the anchor frame 890. In some embodiments, the hub members 998 and 896 are configured in other arrangements. For example, in some embodiments the hub member 896 is located within the hub member 998.

In some embodiments, the anchor arms 894 are interwoven with the elongate members 992 of the occlusive device frame 990. The interweaving of the anchor arms 894 with the elongate members 992 can be configured in all possible arrangements as long as the free ends of the anchor arms 894 protrude from the lateral skirt 994 of the occlusive device frame 990.

In some embodiments of occlusive device 1000, the anchor arms 894 protrude from the lateral skirt 994 in the area of the distal end of the lateral skirt 994. In some embodiments of occlusive device 1000, the anchor arms 894 protrude from the lateral skirt 994 in the area of the proximal end of the lateral skirt 994. In some embodiments of occlusive device 1000, the anchor arms 894 protrude from the lateral skirt 994 in the mid-body area between the proximal end of the lateral skirt 994 and the distal end of the lateral skirt 994. In some embodiments of occlusive device 1000, the anchor arms 894 have dissimilar lengths and protrude from the lateral skirt 994 at different areas along the lateral skirt 994 (e.g., some protrude from the proximal end area while others protrude from the mid-body area, or some protrude from the distal end area while others protrude from the mid-body area, or some protrude from the proximal end area while others protrude from the distal end area).

Figure 53:
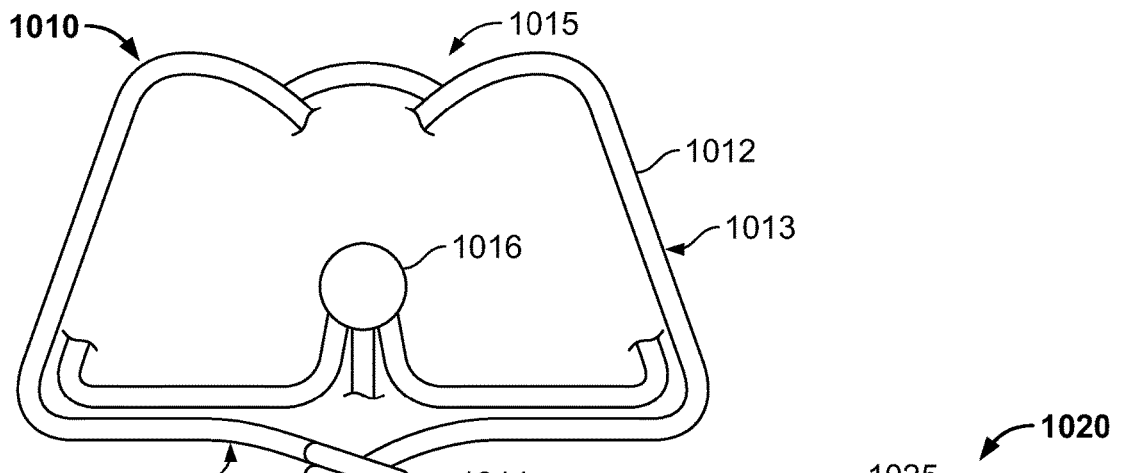
FIG. 53 is a conceptual diagram of a portion of yet another example occlusive device frame.
Figure 54:
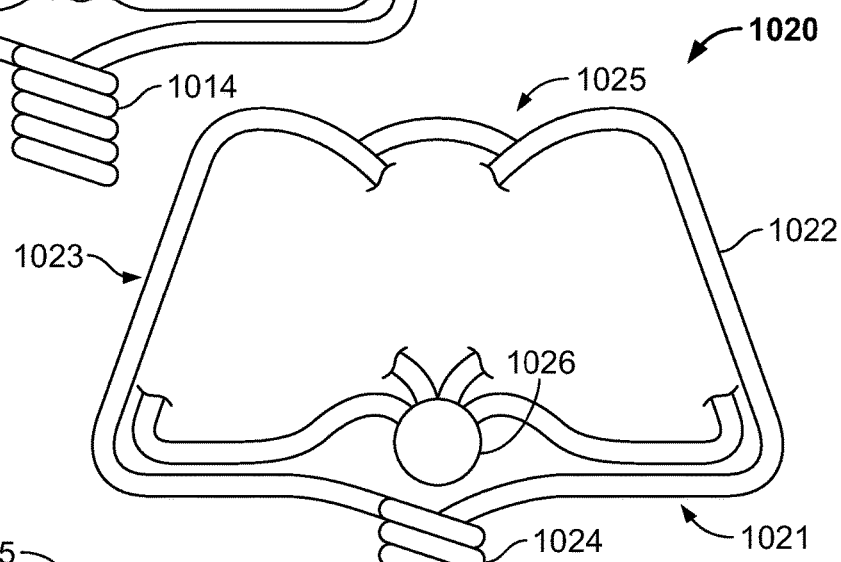
FIG. 54 is a conceptual diagram of a portion of yet another example occlusive device frame.
Figure 55:
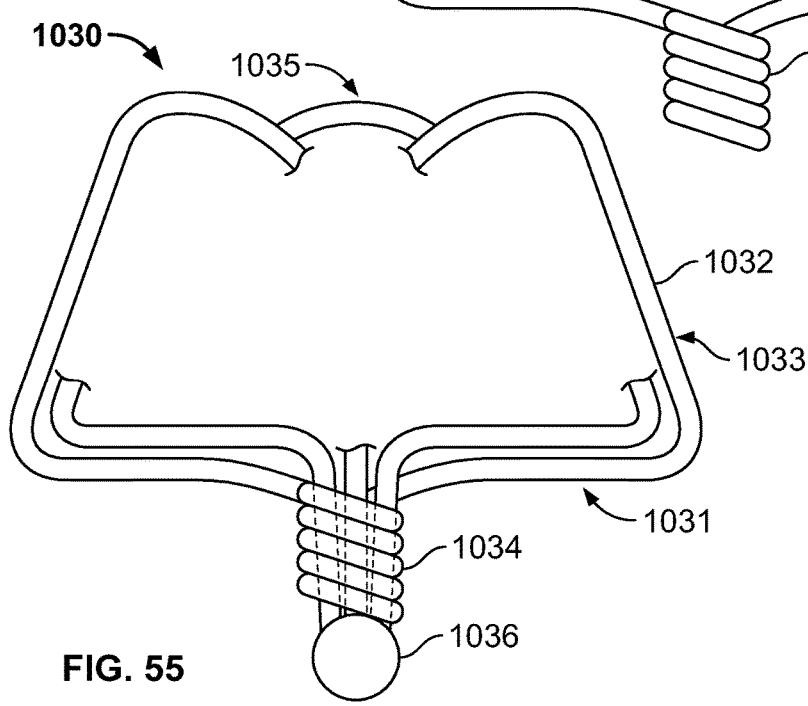
FIG. 55 is a conceptual diagram of a portion of yet another example occlusive device frame.

FIGS. 53-55 schematically represent additional embodiments of occlusive devices 1010, 1020, and 1030, respectively. The occlusive devices 1010, 1020, and 1030 are configured such that a first end of the elongate members terminate at an eyelet, and a second end of the elongate members terminate at a laser ball. The laser ball can be formed by melting the ends of the elongate members together using a laser. As such, in some embodiments the laser ball may not be as spherical as shown. It should be understood that the eyelet of the occlusive devices 1010, 1020, and 1030 may be any of the types of hub members described herein (e.g., a ring member, a crimp joint, a tube portion, etc.). FIGS. 53-55 are drawn to highlight particular occlusive device frame features that can be incorporated into the designs of the occlusive devices provided herein. For example, in some of the figures the designs of the hub members and/or occlusion frame features are highlighted. It should be understood that one or more of the features that are highlighted in these figures can be included in any of the occlusive devices described elsewhere herein, and that such features (and other features described herein) can be mixed and matched to create hybrid designs that are entirely within the scope of this disclosure. In these figures, no covering component is shown and some portions of the frames are not shown so that the highlighted frame features are more readily visible. It should be understood that the occlusive devices of FIGS. 53-55 can be combined with a covering component in some embodiments. The covering component can share any or all of the features, characteristics, properties, etc. as described above in reference to the covering component 104 and/or any other exemplary covering components described herein.

It should be understood that the occlusive devices 1010, 1020, and 1030 can be combined with a covering component in some embodiments. The covering component can share any or all of the features, characteristics, properties, etc. as described above in reference to the covering component 104 and/or any other exemplary covering components described herein. Further, it should be understood that the occlusive devices 1010, 1020, and 1030 can be combined with the anchor frames provided herein (e.g., anchor frame 880, 890, 920, 924, 934, 942, 954, etc.).

FIG. 53 is a conceptual diagram of a portion of an example occlusive device 1010 that has a wound wire construct of elongate members 1012. As with some occlusive device embodiments described elsewhere herein, the occlusive device 1010 includes an occlusive face 1011, a laterally facing skirt 1013, and an inverted section 1015. In some embodiments, the elongate members 1012 of the occlusive device 1010 are formed using a cut-tube process. In some such embodiments, the hub member 1014 is a tube portion. In the depicted embodiment, the first ends of the elongate members 1012 are terminated at the hub member 1014, which is an eyelet 1014. The other ends of the elongate elements 1012 are terminated at a laser ball 1016 (i.e., the ends of the elongate elements 1012 are conjoined together). In the depicted embodiment of occlusive device 1010, the ends of the elongate elements 1012 that are terminated at the laser ball 1016 are inverted. That is, the ends of the elongate elements 1012 that are terminated at the laser ball 1016 are directed away from the eyelet 1014.

FIG. 54 is a conceptual diagram of a portion of an example occlusive device 1020 that has a wound wire construct of elongate members 1022. As with some occlusive device embodiments described elsewhere herein, the occlusive device 1020 includes an occlusive face 1021, a laterally facing skirt 1023, and an inverted section 1025. In some embodiments, the elongate members 1022 of the occlusive device 1020 are formed using a cut-tube process. In some such embodiments, the hub member 1024 is a tube portion. In the depicted embodiment, the first ends of the elongate members 1022 are terminated at the hub member 1024, which is an eyelet 1024. The other ends of the elongate elements 1022 are terminated at a laser ball 1026. In the depicted embodiment of occlusive device 1020, the ends of the elongate elements 1022 that are terminated at the laser ball 1026 are floating. That is, the laser ball 1026 is not in engagement with the eyelet 1014.

FIG. 55 is a conceptual diagram of a portion of an example occlusive device 1030 that has a wound wire construct of elongate members 1032. As with some occlusive device embodiments described elsewhere herein, the occlusive device 1030 includes an occlusive face 1031, a laterally facing skirt 1033, and an inverted section 1035. In some embodiments, the elongate members 1032 of the occlusive device 1030 are formed using a cut-tube process. In some such embodiments, the hub member 1034 is a tube portion. In the depicted embodiment, the first ends of the elongate members 1032 are terminated at the hub member 1034, which is an eyelet 1034. The other ends of the elongate elements 1032 are terminated at a laser ball 1036. In the depicted embodiment of occlusive device 1030, the ends of the elongate elements 1032 that are terminated at the laser ball 1036 are nested within the eyelet 1034.

Figure 56:
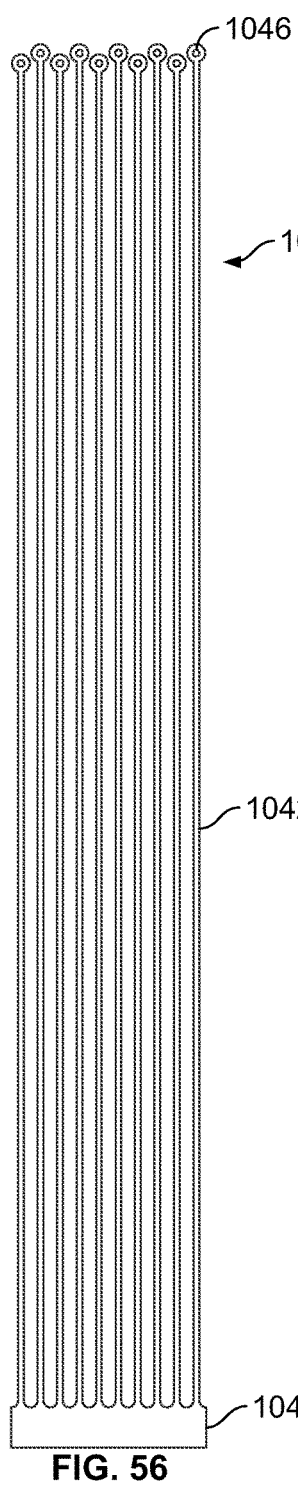
FIG. 56 illustrates a material cutting pattern for an occlusive device frame in accordance with some embodiments.
Figure 57:
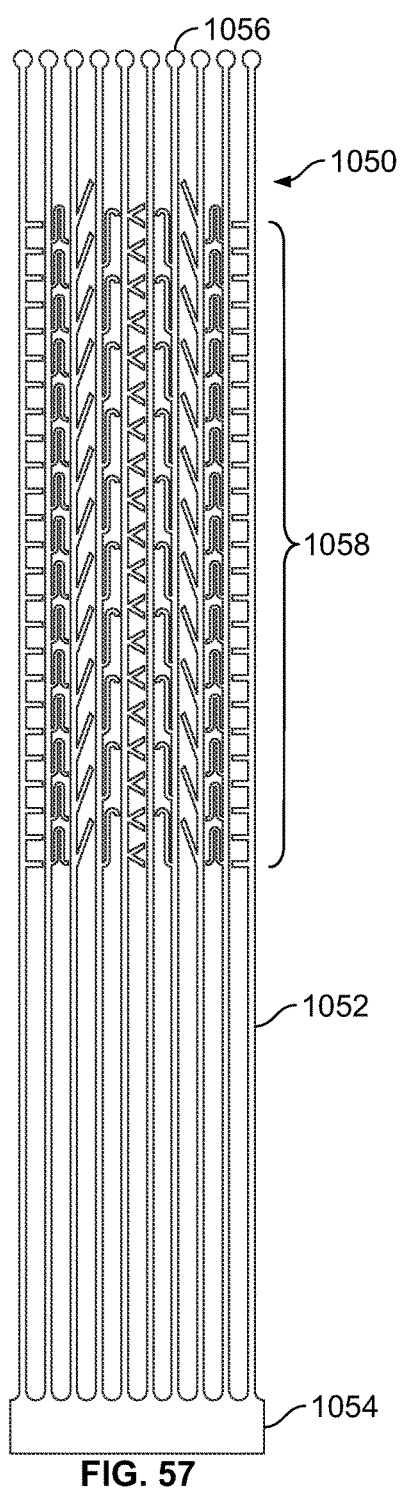
FIG. 57 illustrates another material cutting pattern for an occlusive device frame in accordance with some embodiments.
Figure 58:
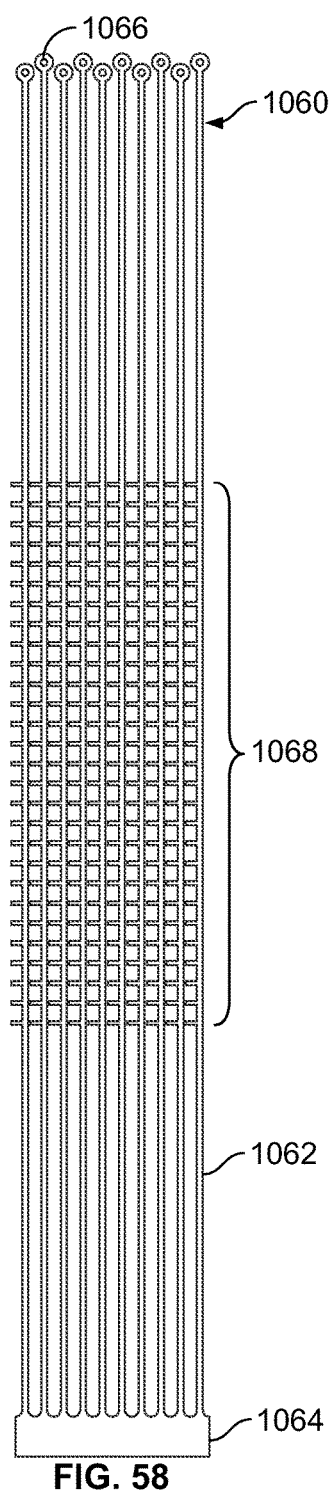
FIG. 58 illustrates another material cutting pattern for an occlusive device frame in accordance with some embodiments.

FIGS. 56-58 illustrate example material cutting patterns 1040, 1050, and 1060, respectively, that can be used to form some embodiments of the occlusion device frames provided herein. Using material cutting patterns 1040, 1050, and 1060, occlusion device frames can be formed as unitary members. In some cases, the material cutting patterns 1040, 1050, and 1060 can be utilized for laser-cutting a tube of material (e.g., a tube of NiTi or other materials). In some such cases, the resulting occlusion device frames are a unitary and seamless construct. Or, in some cases a planar sheet of material can be cut as shown and the sheet can thereafter be formed into a tube. In some embodiments, chemical etching, machining, water jet cutting, or other techniques can be used to create the occluder device frames in accordance with the material cutting patterns 1040, 1050, and 1060. In some embodiments, the example material cutting patterns 1040, 1050, and 1060 facilitate the formation of occlusion device frames that are cut from a material to form wire-like elongate members that can be wound to form the frame. In some embodiments, anchor features are integrally formed with the elongate members. The anchor features can have a wide variety of configurations and can be located anywhere on the occlusion device frames.

FIG. 56 illustrates a material cutting pattern 1040 that includes a plurality of elongate members 1042. The first ends of the elongate members 1042 terminate at a hub member 1044 and the second ends of the elongate members 1042 at free ends 1046. The hub member 1044 comprises, or can be formed into, a tube portion 1044. When formed into an occlusion frame, the free ends 1046 can be terminated into various types of hub members (e.g., a ring member, an eyelet, a crimp joint, a laser ball, etc.). In this embodiment, the free ends 1046 include tabs with holes to facilitate ease of attachment, handling, and manipulation (e.g., by inserting a wire through the hole, etc.).

FIG. 57 illustrates a material cutting pattern 1050 that includes a plurality of elongate members 1052. The first ends of the elongate members 1052 terminate at a hub member 1054 and the second ends of the elongate members 1052 terminate at free ends 1056. The hub member 1054 comprises, or can be formed into, a tube portion 1044. When formed into an occlusion frame, the free ends 1056 can be terminated into various types of hub members (e.g., a ring member, an eyelet, a crimp joint, a laser ball, etc.). In this embodiment, the elongate members 1052 include various types of anchor features 1058 (e.g., barbs, hooks, atraumatic protrusions, angled protrusions, radial protrusions, bifurcated protrusions, spring members, etc., and combinations thereof). Such anchor features 1058 are integral with the elongate members 1052, and can be configured to protrude from the occlusion device into contact with tissue at an implant site to resist migration of the occlusion device. The anchor features 1058 may also be referred to as micro-hooks or in-frame anchor features. The anchor features 1058 can be located at any locations on the elongate members 1052 as desired. In result, when formed into an occlusion frame, the anchor features can be located at any region of the frame, and at multiple regions on the frame as desired. It should be understood that such anchor features 1058 can be included on the elongate members that form any of the anchor frames, occlusive device frames, and occlusion devices provided herein.

In some embodiments, the anchor features 1058 can serve to stabilize the occlusive devices in one or more directions (e.g., in the proximal and distal directions, laterally, rotationally, etc.) when the device has been implanted. The inclusion of the anchor features 1058 that are integrally formed with the elongate members 1052 provides various design advantages. For example, in some embodiments no additional anchor frame needs to be included in the occlusive device. However, in some embodiments an additional anchor frame can be included in occlusive devices that have anchor features 1058. Further, the anchor features 1058 can be formed to have a wide variety of different shapes. In some embodiments, the elongate members 1052 are configured with a width to thickness ratio that can help facilitate the desired orientation of the anchor features 1058 when the elongate members 1052 have been wound into the shape of the occlusive device frame. For example, in some embodiments, an elongate member 1052 having a thickness greater than the width of the elongate member 1052 helps the anchor features 1058 to be properly oriented when the elongate members 1052 have been wound into the shape of the occlusive device frame.

FIG. 58 illustrates a material cutting pattern 1060 that includes a plurality of elongate members 1062. The first ends of the elongate members 1062 terminate at a hub member 1064 and the second ends of the elongate members 1062 terminate at free ends 1066. The hub member 1064 comprises, or can be formed into, a tube portion 1064. When formed into an occlusion frame, the free ends 1066 can be terminated into various types of hub members (e.g., a ring member, an eyelet, a crimp joint, a laser ball, etc.). In this embodiment, the elongate members 1062 include anchor features 1068. In this embodiment, the anchor features 1068 are protrusions. The anchor features 1068 are integral with the elongate members 1062, and can be configured to protrude from the occlusion device into contact with tissue at an implant site to resist migration of the occlusion device. It should be understood that such anchor features 1068 can be included on the elongate members that form any of the anchor frames, occlusive device frames, and occlusion devices provided herein.

Figure 59:
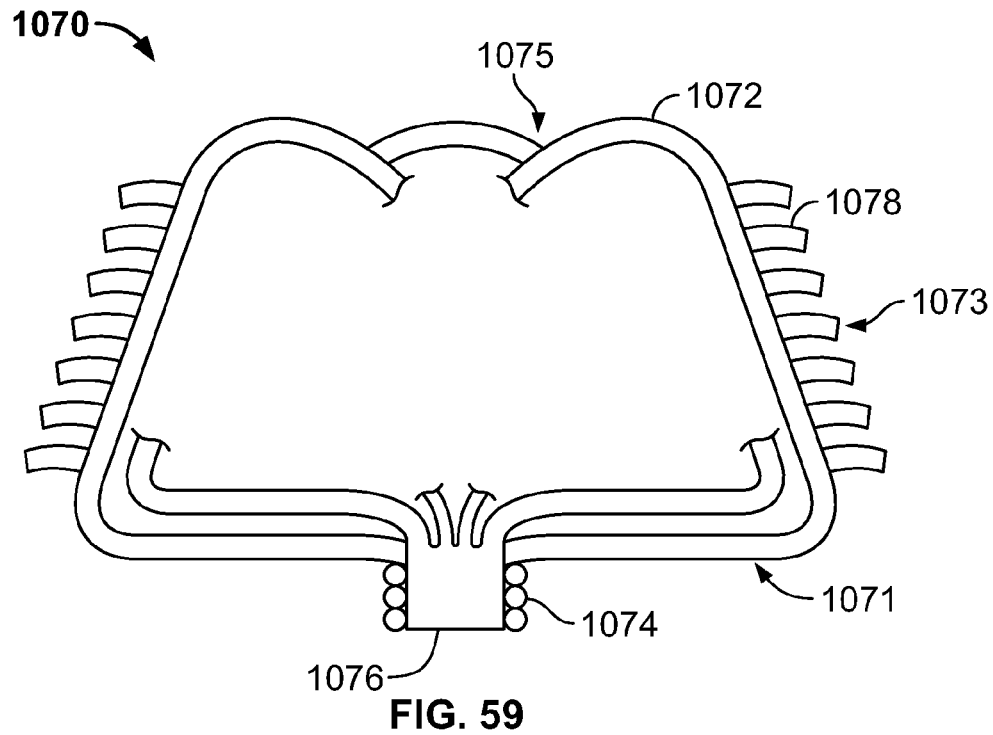
FIG. 59 is a conceptual diagram of a portion of yet another example occlusive device frame.
Figure 60:
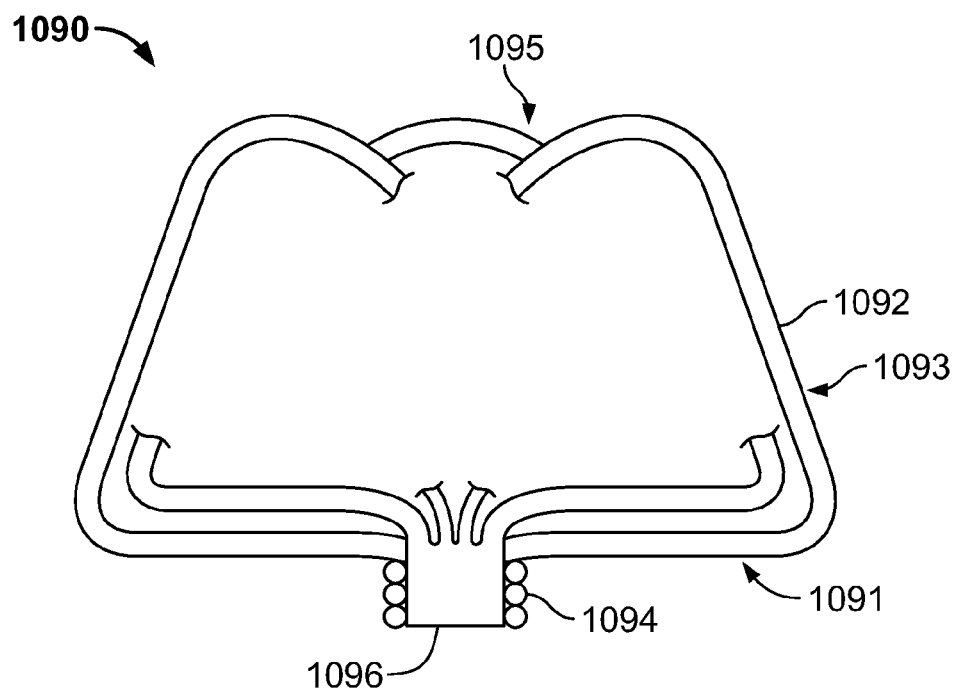
FIG. 60 is a conceptual diagram of a portion of yet another example occlusive device frame.

FIGS. 59 and 60 schematically represent additional embodiments of occlusive devices 1070 and 1090, respectively. In some embodiments, the occlusive devices 1070 and 1090 are formed using the material cutting patterns 1040, 1050, or 1060 as described above, or variants thereof. The occlusive devices 1070 and 1090 are configured such that the first ends of the elongate members terminate at an eyelet, and the second ends of the elongate members terminate at a tube portion. It should be understood that the eyelet of the occlusive devices 1070 and 1090 may be any of the types of hub members described herein (e.g., a ring member, a crimp joint, a tube portion, etc.). FIGS. 59 and 60 are drawn to highlight particular occlusive device frame features that can be incorporated into the designs of the occlusive devices provided herein. For example, in some of the figures the designs of the hub members and/or occlusion frame features are highlighted. It should be understood that one or more of the features that are highlighted in these figures can be included in any of the occlusive devices described elsewhere herein, and that such features (and other features described herein) can be mixed and matched to create hybrid designs that are entirely within the scope of this disclosure. In these figures, no covering component is shown and some portions of the frames are not shown so that the highlighted frame features are more readily visible. It should be understood that the occlusive devices of FIGS. 59 and 60 can be combined with a covering component in some embodiments. The covering component can share any or all of the features, characteristics, properties, etc. as described above in reference to the covering component 104 and/or any other exemplary covering components described herein.

FIG. 59 illustrates occlusive device 1070 that includes elongate elements 1072 that form the frame and terminate at an eyelet 1074 and a tube portion 1076. As with some occlusive device embodiments described elsewhere herein, the occlusive device 1070 includes an occlusive face 1071, a laterally facing skirt 1073, and an inverted section 1075. In the depicted embodiment, the tube portion 1076 is nested within the eyelet 1074. In some embodiments the eyelet 1074 may be nested within the tube portion 1076. The occlusive device 1070 also includes integral anchor features 1078 (e.g., refer to FIGS. 57 and 58). The anchor features 1078 can be various types of anchor features (e.g., barbs, hooks, atraumatic protrusions, angled protrusions, radial protrusions, bifurcated protrusions, spring members, etc., and combinations thereof). Such anchor features 1078 are integral with the elongate members 1072, and can be configured to protrude from the occlusion device into contact with tissue at an implant site to resist migration of the occlusion device. It should be understood that such anchor features 1078 can be included on the elongate members that form any of the anchor frames, occlusive device frames, and occlusion devices provided herein.

FIG. 60 illustrates occlusive device 1090 that includes elongate elements 1092 that form the frame and terminate at an eyelet 1094 and a tube portion 1096. As with some occlusive device embodiments described elsewhere herein, the occlusive device 1090 includes an occlusive face 1091, a laterally facing skirt 1093, and an inverted section 1095. In the depicted embodiment, the tube portion 1096 is nested within the eyelet 1094. In some embodiments the eyelet 1094 may be nested within the tube portion 1096.

Figure 61:
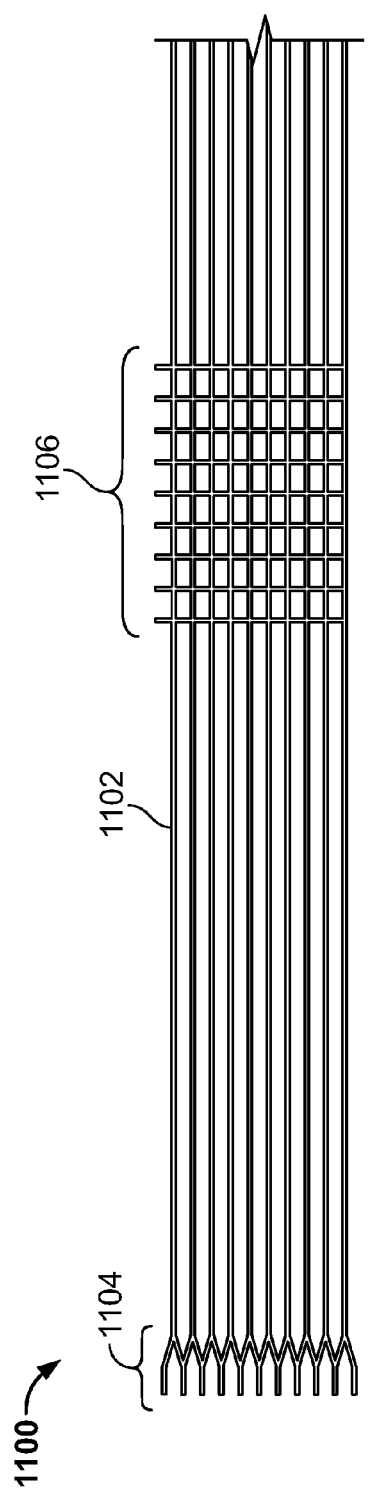
FIG. 61 illustrates another material cutting pattern for an occlusive device frame in accordance with some embodiments.
Figure 62:
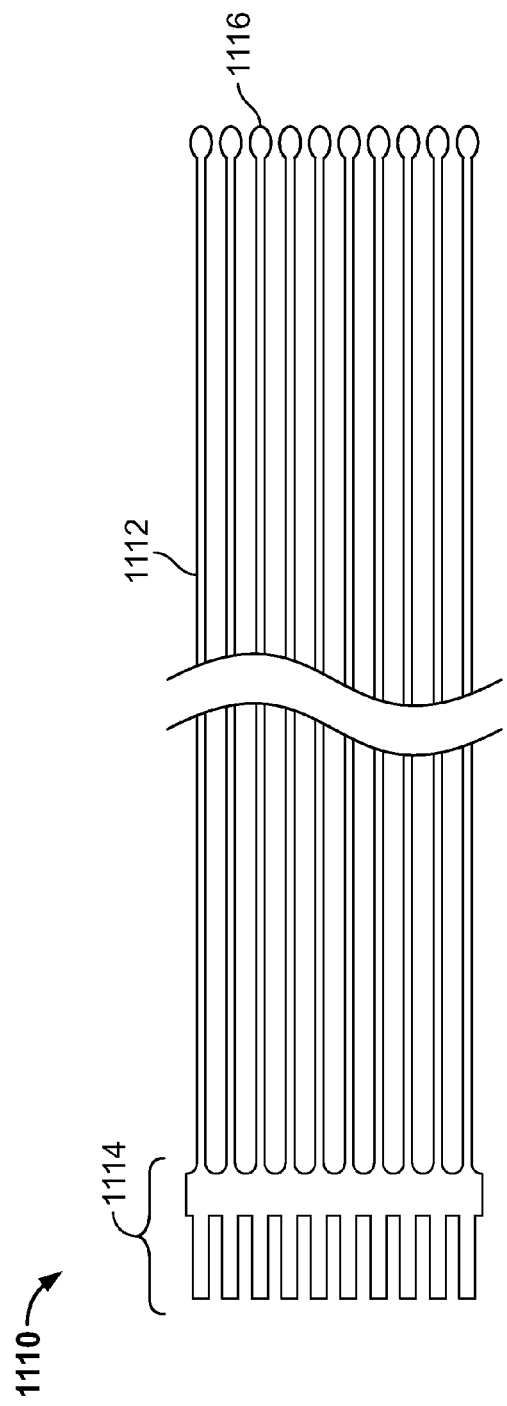
FIG. 62 illustrates another material cutting pattern for an occlusive device frame in accordance with some embodiments.

FIGS. 61 and 62 illustrate material cutting patterns 1100 and 1110, respectively, that can be used to form some embodiments of the occlusion device frames provided herein. Using material cutting patterns 1100 and 1110, occlusion device frames can be formed as unitary members. In some cases, the material cutting patterns 1100 and 1110 can be utilized for laser-cutting a tube of material (e.g., a tube of NiTi or other materials). In some such cases, the resulting occlusion device frames are a unitary and seamless construct. Or, in some cases a planar sheet of material can be cut as shown and the sheet can thereafter be formed into a tube. In some embodiments, chemical etching, machining, water jet cutting, or other techniques can be used to create the occluder device frames in accordance with the material cutting patterns 1100 and 1110.

FIG. 61 illustrates a material cutting pattern 1100 that includes a plurality of elongate members 1102. The first ends of the elongate members 1102 terminate at a hub member 1104, and the second ends of the elongate members 1042 terminate at free ends (not shown). The hub member 1104 comprises, or can be formed into, a tube portion 1104. The tube portion 1104 is configured to allow the tube portion 1104 to be more compressible than a solid tube portion (e.g., tube portions 1044, 1054, and 1064 of FIGS. 56-58). Such compressibility of the tube portion 1104 can facilitate a reduced profile delivery configuration in some embodiments. When formed into an occlusion frame, the free ends can be terminated into various types of hub members (e.g., a ring member, an eyelet, a crimp joint, a laser ball, etc.). The material cutting pattern 1100 also includes anchor features 1106.

FIG. 62 illustrates a material cutting pattern 1110 that includes a plurality of elongate members 1112. The first ends of the elongate members 1112 terminate at a hub member 1114, and the second ends of the elongate members 1142 terminate at free ends 1114. As will be described further in reference to FIGS. 63A-63C, the hub member 1114 comprises, or can be formed into, a tube portion 1114 that includes receptacles for the elongate members 1142. When formed into an occlusion frame, the free ends 1116 can be contained within the hub member 1114.

Figure 63A:
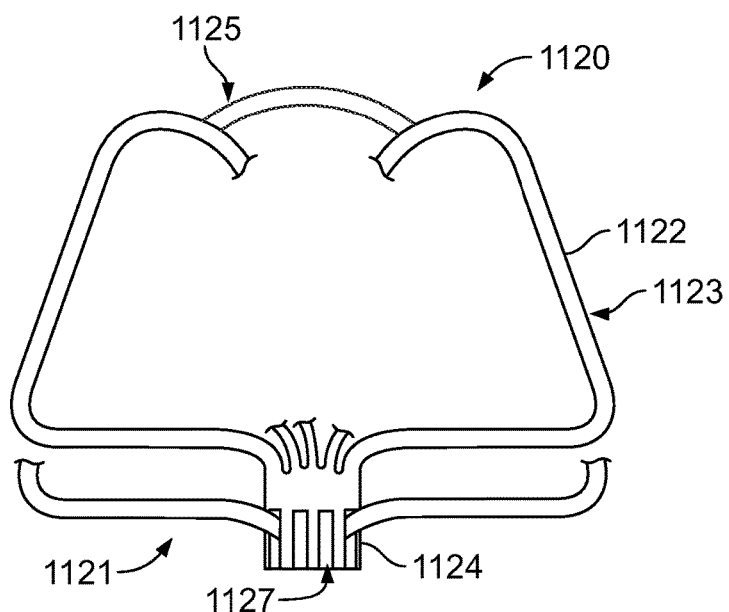
FIG. 63A is a conceptual diagram of a portion of yet another example occlusive device frame.
Figure 63B:
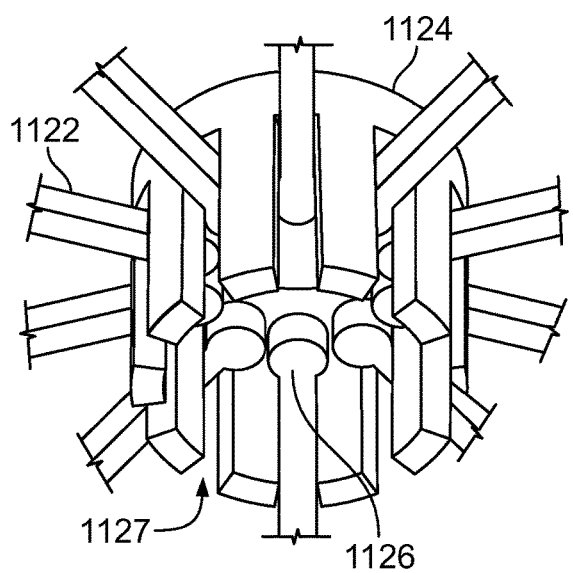
FIGS. 63B and 63C illustrate a hub member portion of the occlusive device frame of FIG. 63A.
Figure 63C:
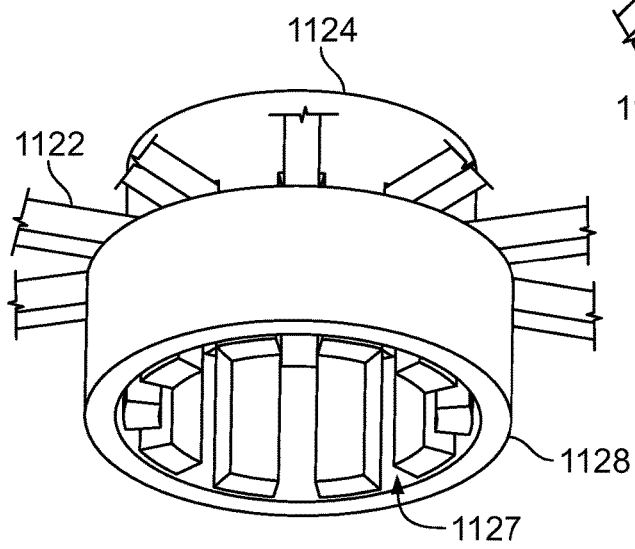

FIGS. 63A-63C illustrate another example occlusive device 1120. FIG. 63A is a side view of the occlusive device 1120, and FIGS. 63B and 63C are partial views of the occlusive device 1120 that show the terminations of the elongate members 1122. As with some occlusive device embodiments described elsewhere herein, the occlusive device 1120 includes an occlusive face 1121, a laterally facing skirt 1123, and an inverted section 1125. It should be understood that the occlusive device of FIGS. 63A-63C can be combined with a covering component in some embodiments. The covering component can share any or all of the features, characteristics, properties, etc. as described above in reference to the covering component 104 and/or any other exemplary covering components described herein.

In some embodiments, the occlusive device 1120 is formed using the material cutting pattern 1110 as described above in reference to FIG. 62, or a variant thereof. The occlusive device 1120 is configured such that the first ends of the elongate members 1122 terminate at a tube portion 1124, and the second ends of the elongate members 1122 terminate at free ends 1126 that are located within the tube portion 1124. The tube portion 1124 includes receptacles 1127 (e.g., slots, holes, etc.) through which the elongate members 1122 may extend. The free ends 1126 include bulbous ends that are larger than the receptacles 1127 to provide resistance against removal of the free ends 1126 from within the tube portion 1124. In some embodiments, a retainer ring 1128 is installed onto the outer diameter of the tube portion 1124 to provide further retention of the free ends 1126 within the tube portion 1124.

While the occlusion devices have been described with respect to an LAA, in some embodiments, the occlusion devices can be used to occlude or seal other apertures within a body of a patient, such as a right atrial appendage, a fistula, a patent ductus arteriousus, an atrial septal defect, a ventricular septal defect, a paravalvular leak, an arteriovenous malformation, or a body vessel.

The examples discussed herein have focused on occlusion devices, but it is contemplated that the features described herein may also be used with other types of medical devices or accessories. Examples of implantable devices and accessories include, without limitation, occlusion and closure devices, filters (e.g. inferior vena cava filter or an embolic protection filter), catheter based grabbers or retrieval devices, temporary filtration devices, stents, stent-grafts, and vessel sizers. In some examples, the devices discussed herein can provide a vessel or appendage liner. For example, the device may be deployed into the appendage by initially placing the occlusive face within the appendage so that the inverted section 116 (e.g., the cupped portion of the device) faces the left atrial chamber. For embodiments where the device is designed to filter, the covering component may be porous, where the pores are sized to generally permit blood to pass through the pores, but are sized to prevent emboli from passing through the pores of the covering component.

In some embodiments, an occlusion or filtering device can include a first frame that is similar to any of the frames discussed above herein, and a sub-frame that is disposed within the first frame. The device may not include a covering component in some implementations. The sub-frame may comprise elongate members that follow a rotational direction opposite the rotational direction followed by elongate members of the first frame, in some examples. The sub-frame may be configured to clot or occlude in some examples. The sub-frame may be configured to filter in some examples.

For additional examples of hub features that can be used with the devices discussed herein, see the provisional application titled "Joint Assembly for Medical Devices," having inventors Coby C. Larsen, Steven J. Masters, and Thomas R. McDaniel, filed on 16 Nov. 2012, which is herein incorporated by reference in its entirety for all purposes, and see also the provisional application titled "Space Filling Devices," having inventors Coby C. Larsen, Brandon A. Lurie, Steven J. Masters, Thomas R. McDaniel, and Stanislaw L. Zukowski, filed on 15 Mar. 2013, and which is herein incorporated by reference in its entirety for all purposes. For additional examples of delivery system devices, systems, and techniques that can be used to deliver, deploy, reposition, and retrieve the devices discussed herein, see the provisional application titled "Implantable Medical Device Deployment System," having inventors Steven J. Masters and Thomas R. McDaniel, filed on 16 Nov. 2012, and which is herein incorporated by reference in its entirety for all purposes.

Several characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shapes, sizes, and arrangements of parts including combinations within the principles described herein, to the full extent indicated by the broad, general meaning of the terms in which the appended claims are expressed. To the extent that these various modifications depart from the spirit and scope of the appended claims, they are intended to be encompassed therein. All references, publications, and patents referred to herein, including the figures and drawings included therewith, are incorporated by reference in their entirety.

What is claimed is:

1. A medical device comprising:
    an occlusive device frame comprising a plurality of elongate occlusive device frame members, each of the elongate frame members including a first end and a second end;
    a first hub member that aggregates the first ends of the plurality of occlusive device elongate members and the first hub member is a tube portion of the occlusive device frame, the first hub member and the plurality of elongate occlusive device frame members being portions of a first cut-tube;
    wherein the occlusive device frame includes an occlusive face portion, a laterally facing skirt portion, and a distal portion, and wherein first portions of the occlusive device elongate members define the occlusive face portion and extend radially from the first hub member, second portions of the occlusive device elongate members define the laterally facing skirt portion and extend in a distal and helical direction along a first rotational direction from the occlusive face portion, and wherein the plurality of occlusive device elongate frame members terminate in free ends at the distal portion; and wherein the plurality of occlusive device elongate frame members in the distal portion form a convex shape by extending toward a longitudinal axis of the medical device; and
    an anchor frame comprising a plurality of anchor device elongate members that extend from a second hub member such that free ends of the anchor device elongate members protrude from the laterally facing skirt portion and the second hub member is a tube portion of the anchor frame, the second hub member and the plurality of anchor device elongate members being portions of a second cut-tube,
    wherein the first hub member is directly nested within the second hub member.

2. The medical device of claim 1, wherein the occlusive face portion of the occlusive device frame is substantially flat.

3. The medical device of claim 1, wherein second hub member is disposed concentrically within the first hub member.

4. The medical device of claim 1, wherein portions of the anchor device elongate members extend along the laterally facing skirt portion substantially parallel to the occlusive device elongate members that define the laterally facing skirt portion.

5. The medical device of claim 1, wherein the plurality of elongate occlusive device frame members include curved portions within an area of the occlusive face portion.

6. The medical device of claim 1, wherein the first hub member is cylindrical, and wherein the second hub member is cylindrical.

7. The medical device of claim 6, wherein the first hub member is coupled within the second hub member.

8. The medical device of claim 1, further comprising a covering component attached to at least a portion of the occlusive device frame and configured to inhibit passage of blood through the covering component.

9. The medical device of claim 8, wherein the covering component comprises ePTFE.

* * * * *